United States Patent
Gono et al.

(10) Patent No.: US 8,531,512 B2
(45) Date of Patent: Sep. 10, 2013

(54) ENDOSCOPE APPARATUS

(75) Inventors: Kazuhiro Gono, Sagamihara (JP);
Mutsumi Ohshima, Hachioji (JP);
Shoichi Amano, Hachioji (JP); Kenji Yamazaki, Hino (JP)

(73) Assignee: Olympus Corporation, Tokyo (JP)

( * ) Notice: Subject to any disclaimer, the term of this patent is extended or adjusted under 35 U.S.C. 154(b) by 1800 days.

(21) Appl. No.: 11/711,846

(22) Filed: Feb. 27, 2007

(65) Prior Publication Data

US 2007/0153542 A1    Jul. 5, 2007

Related U.S. Application Data

(63) Continuation of application No. PCT/JP2005/015671, filed on Aug. 29, 2005.

(30) Foreign Application Priority Data

| Aug. 30, 2004 | (JP) | 2004-250978 |
| Aug. 30, 2004 | (JP) | 2004-250979 |
| Aug. 31, 2004 | (JP) | 2004-252862 |
| Sep. 2, 2004 | (JP) | 2004-256140 |
| Sep. 2, 2004 | (JP) | 2004-256141 |
| Jan. 17, 2005 | (JP) | 2005-009477 |
| Aug. 25, 2005 | (JP) | 2005-244083 |

(51) Int. Cl.
*A61B 1/04* (2006.01)

(52) U.S. Cl.
USPC ............... 348/68; 348/46; 348/70; 348/131

(58) Field of Classification Search
USPC .............................. 348/68, 46, 70
See application file for complete search history.

(56) References Cited

U.S. PATENT DOCUMENTS

| 4,337,437 | A | * | 6/1982 | Hunter et al. ............ 359/349 |
| 5,420,876 | A | * | 5/1995 | Lussier et al. ............ 372/22 |
| 5,590,660 | A | | 1/1997 | MacAulay et al. |
| 6,573,513 | B2 | * | 6/2003 | Hayashi .................. 250/458.1 |
| 2001/0043321 | A1 | * | 11/2001 | Nishi et al. ............ 355/67 |
| 2003/0176768 | A1 | | 9/2003 | Gono et al. |
| 2003/0218137 | A1 | * | 11/2003 | Sendai .................. 250/461.1 |
| 2004/0148141 | A1 | * | 7/2004 | Tsujita et al. ............ 702/190 |

FOREIGN PATENT DOCUMENTS

| EP | 1 302 152 A1 | 4/2003 |
| JP | 61-061587 | 3/1986 |
| JP | 05-084218 | 4/1993 |
| JP | 08-186810 | 7/1996 |
| JP | 10-500588 | 1/1998 |
| JP | 10-216082 | 8/1998 |

(Continued)

*Primary Examiner* — Lan-Dai T Truong
(74) *Attorney, Agent, or Firm* — Scully, Scott, Murphy & Presser, P.C.

(57) ABSTRACT

In an endoscope apparatus of the present invention, while observing a body cavity tissue under narrowband light via a second filter group of a rotating filter, a G2 filter section, B2 filter section, and shading filter section change illumination light to narrowband surface-sequential light of two bands of discrete spectral characteristics, and an image-capturing signal captured by a CCD via the B filter section constitutes a band image having superficial layer tissue information, and an image-capturing signal captured by a CCD via the G filter section constitutes a band image having intermediate layer tissue information. This produces tissue information of a desired depth in the vicinity of a superficial portion of a mucous membrane using an inexpensive and simple configuration.

55 Claims, 44 Drawing Sheets

(56) References Cited

FOREIGN PATENT DOCUMENTS

| | | |
|---|---|---|
| JP | 10-248808 | 9/1998 |
| JP | 2000-047119 | 2/2000 |
| JP | 2001478673 | 7/2001 |
| JP | 2002-034893 | 2/2002 |
| JP | 2002-034908 | 2/2002 |
| JP | 2002-095635 | 4/2002 |
| JP | 2004-202217 | 7/2004 |
| WO | WO 95/26673 | 10/1995 |
| WO | WO 02/07588 A1 | 1/2002 |
| WO | WO 2004/052187 A1 | 6/2004 |

* cited by examiner

FIG.37
(A)
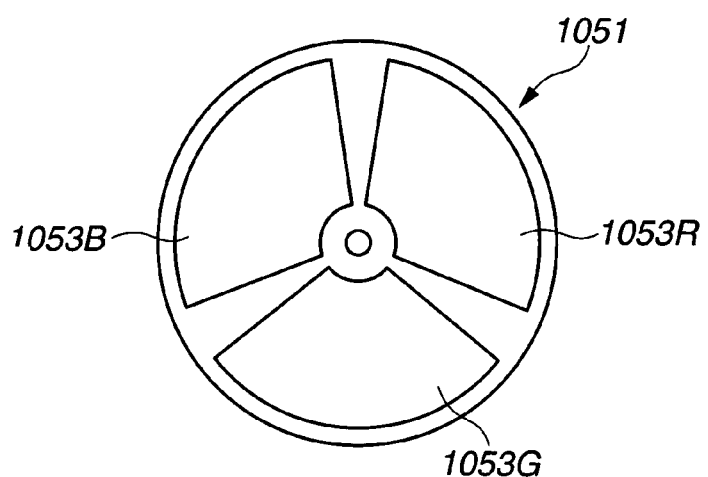
(B)
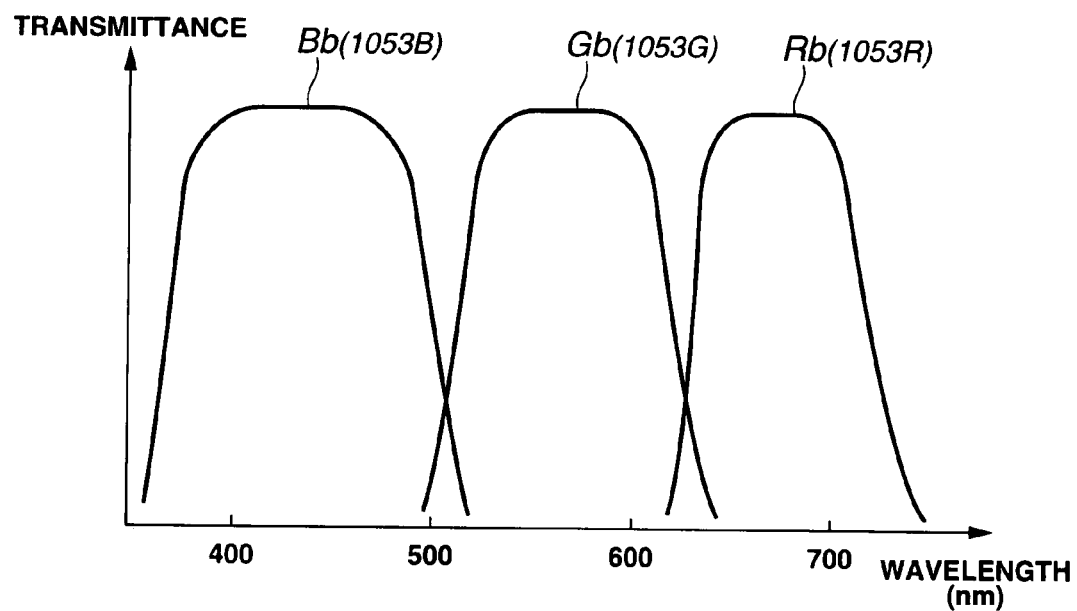

(A)

| m11 | m12 | 0   |
|-----|-----|-----|
| m21 | 0   | m23 |
| m31 | 0   | m33 |

(B)

| m11 | m12 | 0   |
|-----|-----|-----|
| m21 | m22 | m23 |
| m31 | 0   | m33 |

(C)

| m11 | m12 | 0   |
|-----|-----|-----|
| m21 | 0   | 0   |
| m31 | 0   | m33 |

(D)

| m11 | m12 | 0   |
|-----|-----|-----|
| m21 | m22 | 0   |
| m31 | 0   | m33 |

| m21 | 0 | m23 |
|-----|---|-----|
| m31 | 0 | m33 |

(B)

| m21 | m22 | m23 |
|-----|-----|-----|
| m31 | 0 | m33 |

(C)

| m21 | 0 | 0 |
|-----|---|---|
| m31 | 0 | m33 |

ENDOSCOPE APPARATUS

CROSS REFERENCE TO RELATED APPLICATION

This application is a continuation application of PCT/JP2005/015671 filed on Aug. 29, 2005 and claims the benefit of Japanese Applications No. 2004-250978 filed in Japan on Aug. 30, 2004, No. 2004-250979 filed in Japan on Aug. 30, 2004, No. 2004-252862 filed in Japan on Aug. 31, 2004, No. 2004-256140 filed in Japan on Sep. 2, 2004, No. 2004-256141 filed in Japan on Sep. 2, 2004, No. 2005-009477 filed in Japan on Jan. 17, 2005, and No. 2005-244083 filed in Japan on Aug. 25, 2005, the entire contents of each of which are incorporated herein by their reference.

BACKGROUND OF THE INVENTION

1. Field of the Invention

The present invention relates to an endoscope apparatus for capturing an image of living tissue and performing signal processing.

2. Description of the Related Art

An endoscope apparatus, which irradiates an illumination light and obtains an endoscopic image of the inside of a body cavity, has been widely utilized for some time now. This type of endoscope apparatus utilizes an electronic endoscope, which includes image-capturing means for introducing illumination light from a light-source apparatus using a light guide or the like inside a body cavity, and capturing an image of an object by the return light thereof, and by performing signal processing on the image-capturing signal from the image-capturing means using a video processor, displays an endoscopic image on an observation monitor for observation of a diseased part or other such observation site.

When performing ordinary observation of living tissue via an endoscope apparatus, a light-source apparatus emits white light in the visible light region, and, for example, irradiates surface-sequential light on an object via an RGB or other such rotating filter, and can produce a color image either by using a video processor to synchronize and perform image processing of the return light from the surface-sequential light, or by arranging a color chip on the front face of the image-capturing surface of the image-capturing means of the endoscope, capturing an image by separating the return light from the white light into its respective color components via the color chip, and using a video processor to perform image processing.

By contrast, since the absorption characteristics and scattering characteristics of light differ in accordance with the wavelength of irradiated light, for example, in Japanese Patent Laid-open No. 2002-95635, there is proposed a narrowband-light endoscope apparatus, which irradiates narrowband RGB surface-sequential light of discrete spectral characteristics of illumination light in the visible light region onto living tissue, and obtains tissue information of a desired depth of the living tissue.

SUMMARY OF THE INVENTION

An endoscope apparatus of the present invention includes an illumination light supplying unit for supplying illumination light; an endoscope having an image-capturing unit for irradiating the illumination light on an object, and capturing an image of the object by the return light; a two-band restricting unit for restricting the illumination light to a narrowband light of two band regions, and irradiating the narrowband light onto the object; and a signal processing unit for generating a first band region image data and a second band region image data in accordance with the narrowband light of the two band regions restricted and irradiated by the two-band restricting unit, and generating, from the first band region image data and the second band region image data, three-channel color image data for display on a displaying unit.

BRIEF DESCRIPTION OF THE DRAWINGS

FIG. 37 is a diagram showing a configuration and transmission characteristics of a rotating filter;

FIG. 47 is a diagram showing coefficients of a second matrix circuit set in the second variation of FIG. 46;

DETAILED DESCRIPTION OF THE PREFERRED EMBODIMENT(S)

The embodiments of the present invention will be explained below by referring to the figures.

First Embodiment

Figure 1:
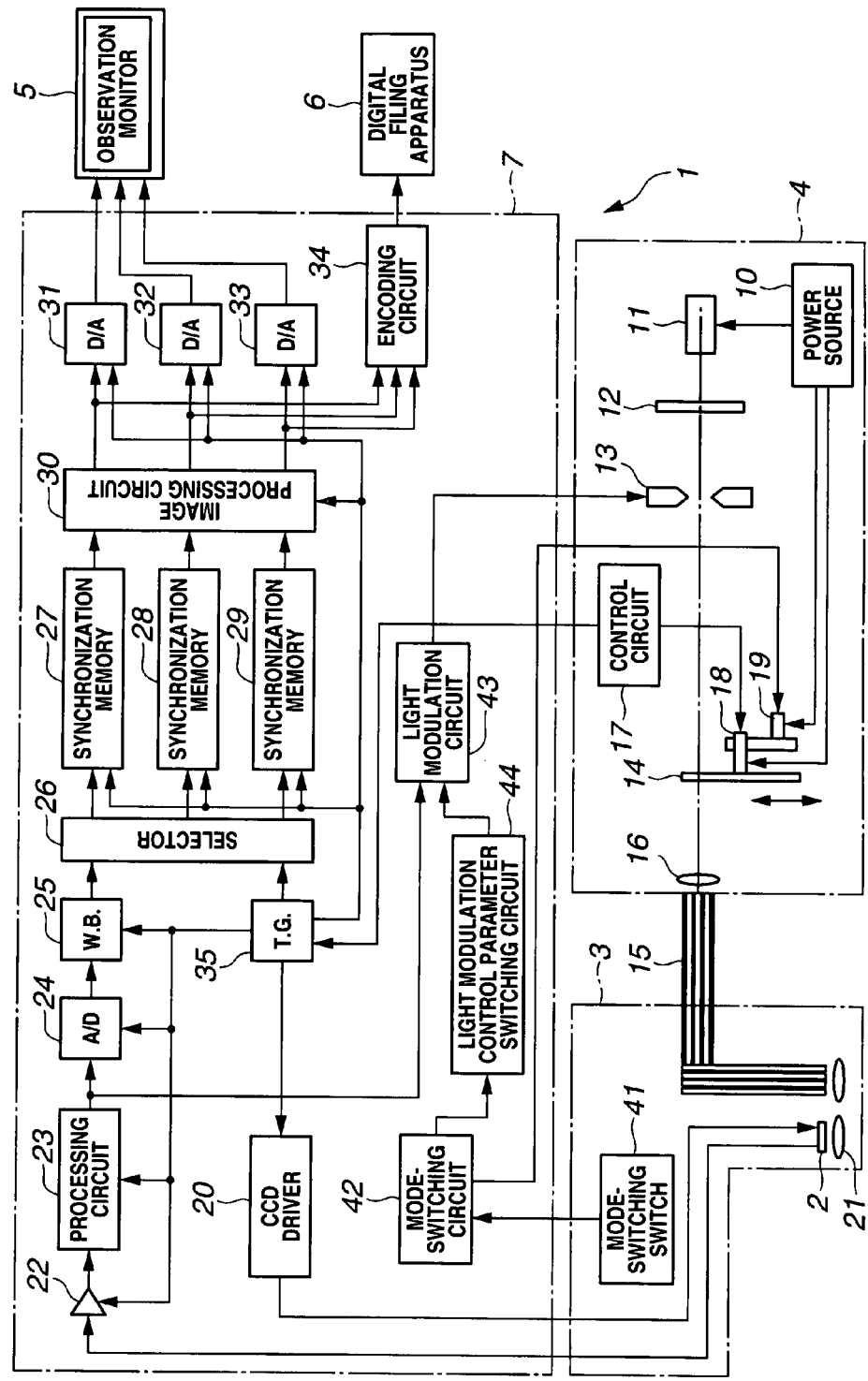
FIG. 1 is a block diagram showing a configuration of an endoscope apparatus related to a first embodiment of the present invention.
Figure 2:
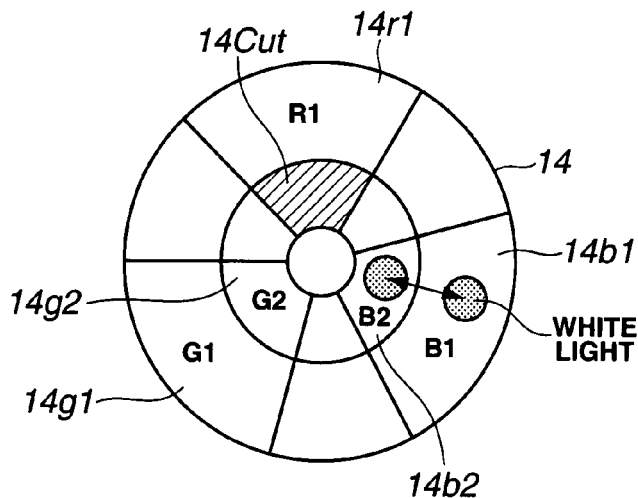
FIG. 2 is a configuration diagram showing a configuration of the rotating filter of FIG. 1.
Figure 3:
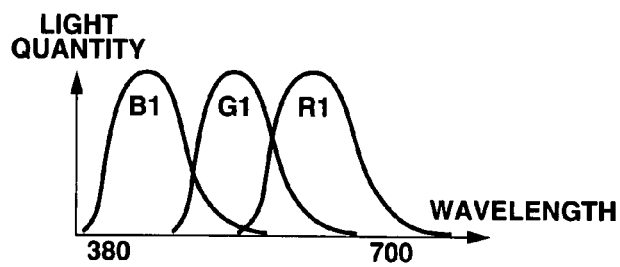
FIG. 3 is a diagram showing spectral characteristics of a first filter group of the rotating filter of FIG. 2.
Figure 4:
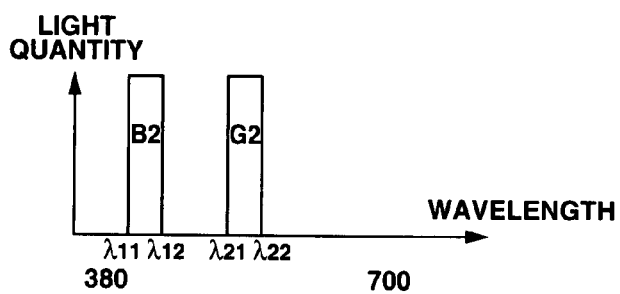
FIG. 4 is a diagram showing spectral characteristics of a second filter group of the rotating filter of FIG. 2.
Figure 5:
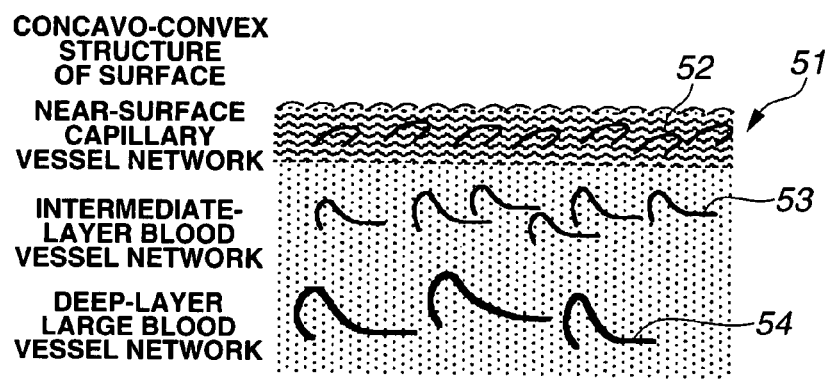
FIG. 5 is a diagram showing the layered structure of a living tissue observed via the endoscope apparatus of FIG. 1.
Figure 6:
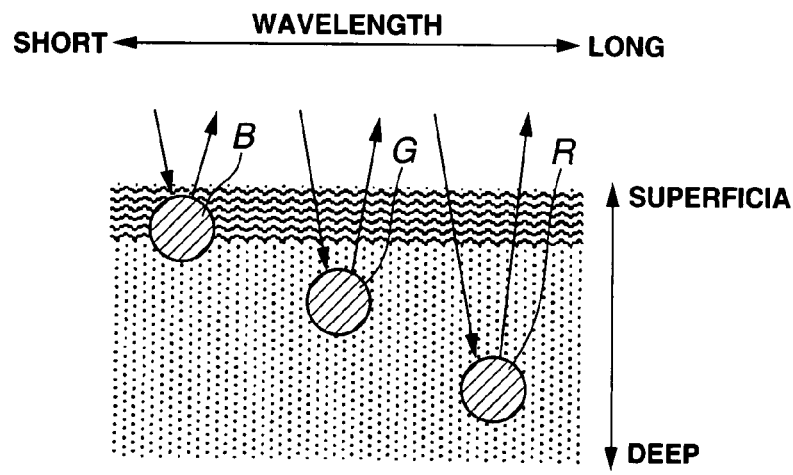
FIG. 6 is a diagram illustrating the access state in the direction of the layers of a living tissue of illumination light from the endoscope apparatus of FIG. 1.
Figure 7:
FIG. 7 is a first diagram showing the respective band images resulting from surface-sequential light permeating the first filter group of FIG. 3.
Figure 8:
FIG. 8 is a second diagram showing the respective band images resulting from surface-sequential light permeating the first filter group of FIG. 3.
Figure 9:
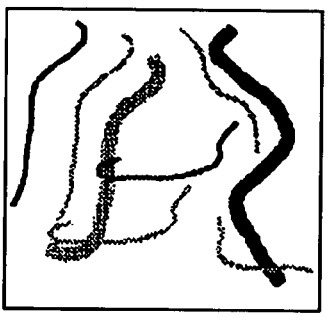
FIG. 9 is a third diagram showing the respective band images resulting from surface-sequential light permeating the first filter group of FIG. 3.
Figure 10:
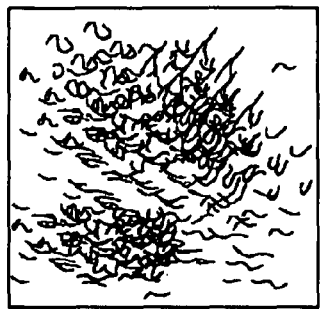
FIG. 10 is a first diagram showing the respective band images resulting from surface-sequential light permeating the second filter group of FIG. 4.
Figure 11:
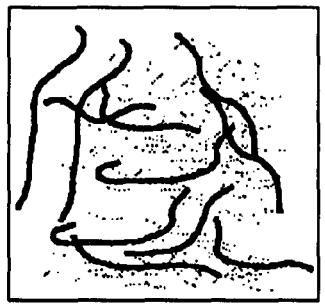
FIG. 11 is a second diagram showing the respective band images resulting from surface-sequential light permeating the second filter group of FIG. 4.
Figure 12:
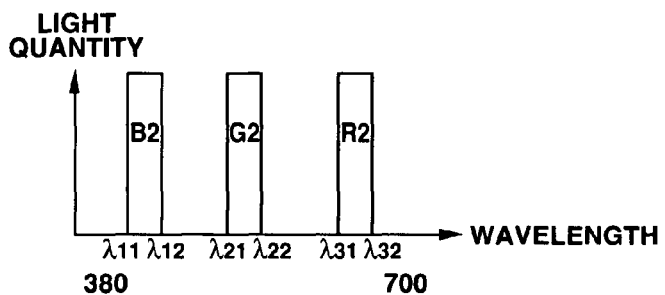
FIG. 12 is a first diagram illustrating a manufacturing method of the second filter group of FIG. 4.
Figure 13:
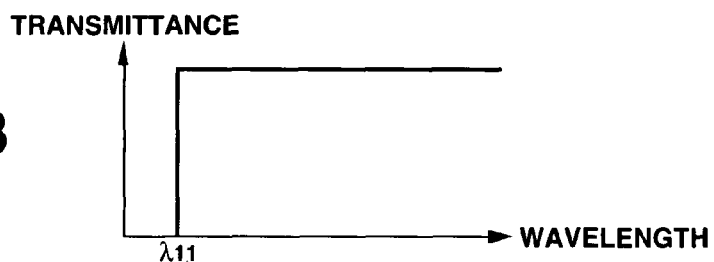
FIG. 13 is a second diagram illustrating a manufacturing method of the second filter group of FIG. 4.
Figure 14:
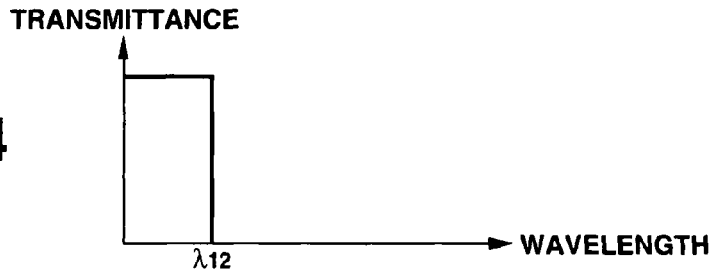
FIG. 14 is a third diagram illustrating a manufacturing method of the second filter group of FIG. 4.
Figure 15:
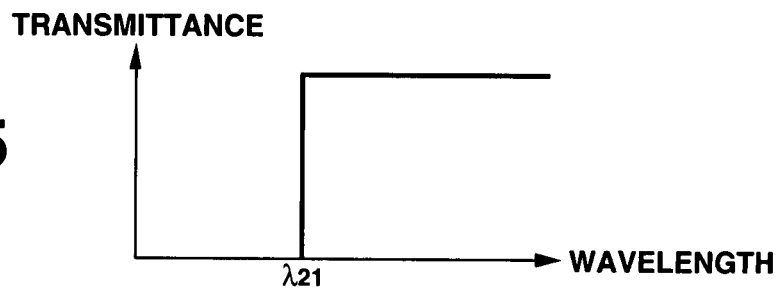
FIG. 15 is a fourth diagram illustrating a manufacturing method of the second filter group of FIG. 4.
Figure 16:
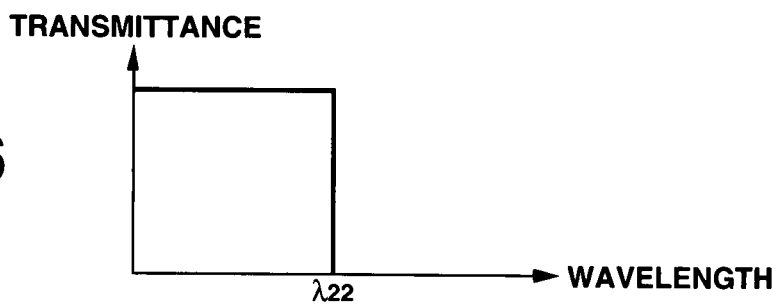
FIG. 16 is a fifth diagram illustrating a manufacturing method of the second filter group of FIG. 4.
Figure 17:
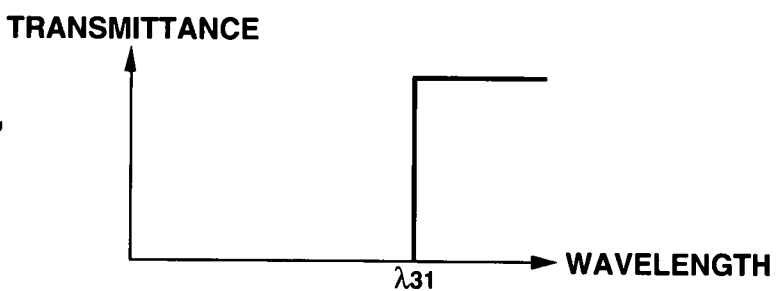
FIG. 17 is a sixth diagram illustrating a manufacturing method of the second filter group of FIG. 4.
Figure 18:
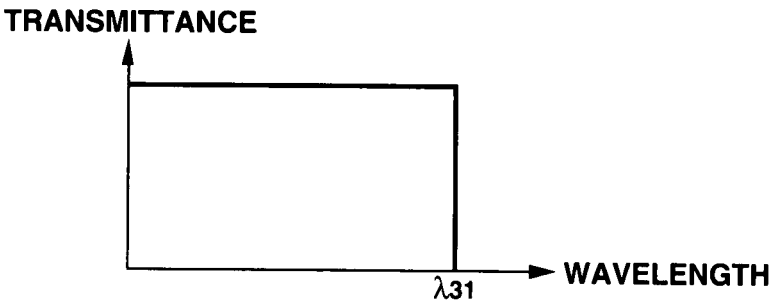
FIG. 18 is a seventh diagram illustrating a manufacturing method of the second filter group of FIG. 4.
Figure 19:
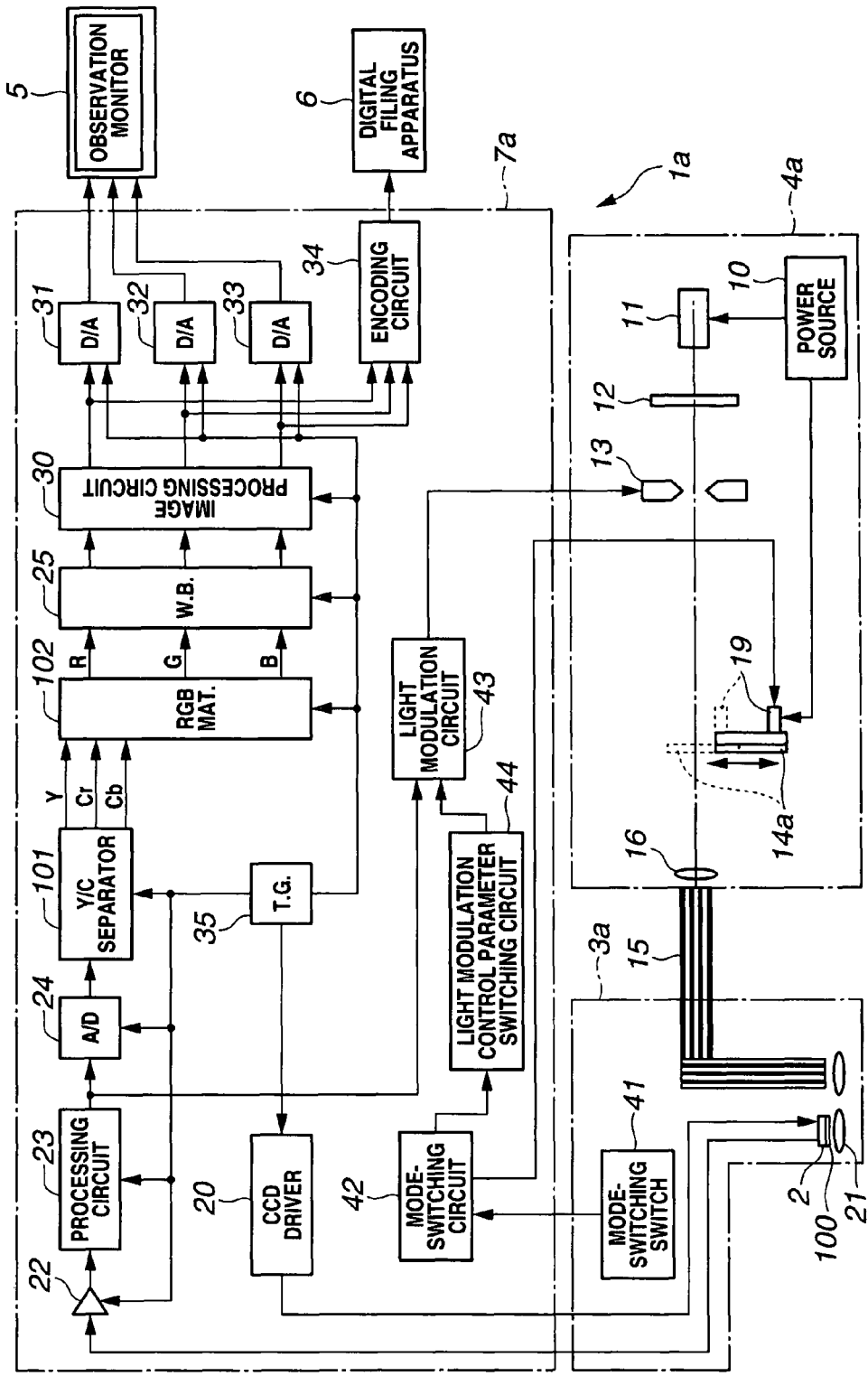
FIG. 19 is a block diagram showing a configuration of a variation of the endoscope apparatus of FIG. 1.
Figure 20:
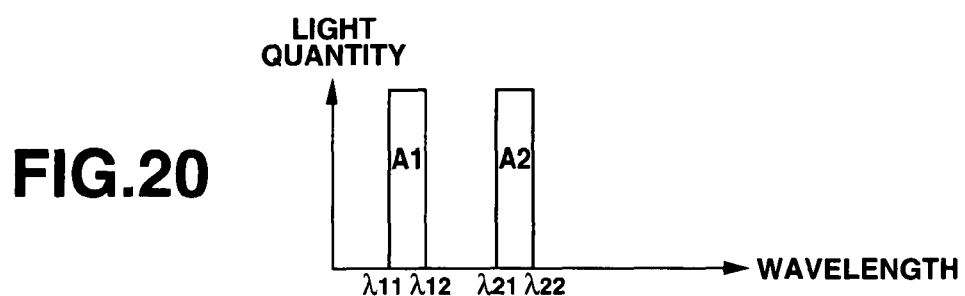
FIG. 20 is a diagram showing the spectral transmission characteristics of the narrowband interference filter of FIG. 19.
Figure 21:
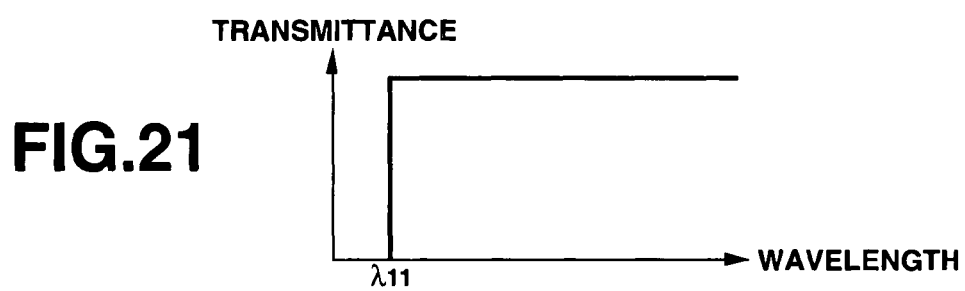
FIG. 21 is a diagram showing the spectral transmission characteristics of a first interference membrane filter for realizing the narrowband interference filter of FIG. 19.
Figure 22:
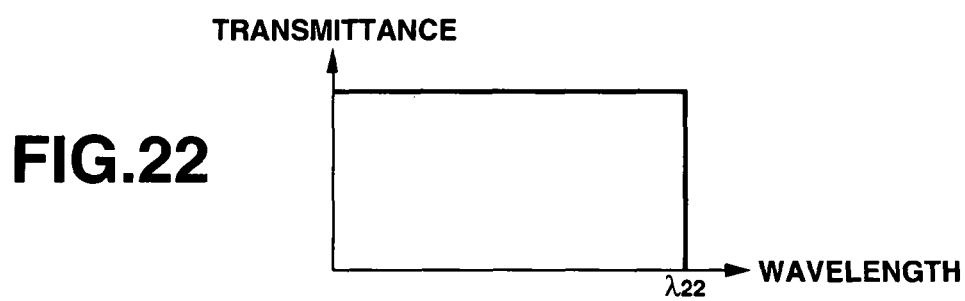
FIG. 22 is a diagram showing the spectral transmission characteristics of a second interference membrane filter for realizing the narrowband interference filter of FIG. 19.
Figure 23:
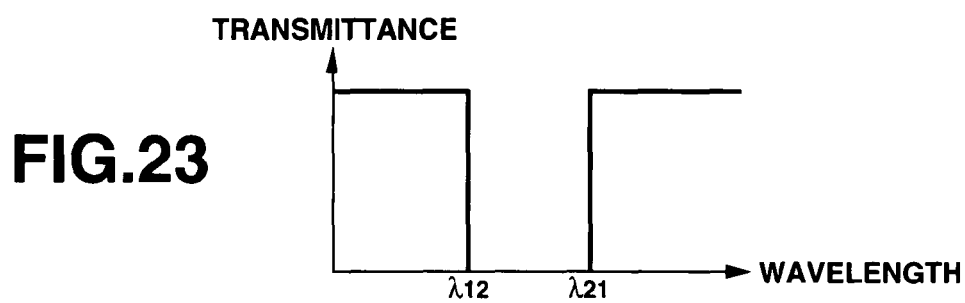
FIG. 23 is a diagram showing the spectral transmission characteristics of a third interference membrane filter for realizing the narrowband interference filter of FIG. 19.
Figure 24:
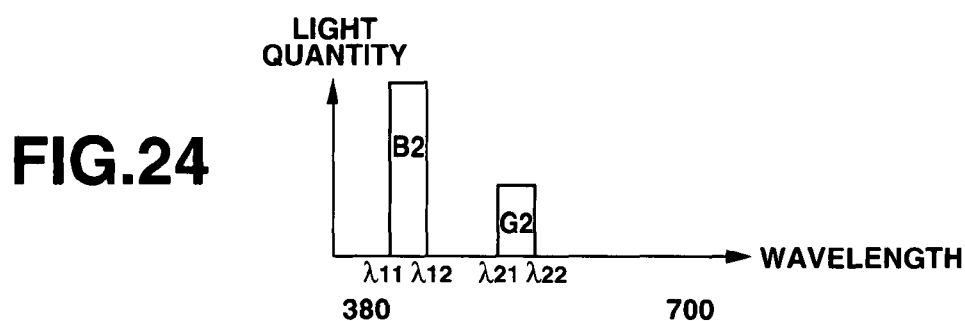
FIG. 24 is a diagram showing the spectral transmission characteristics of a variation of the narrowband interference filter of FIG. 20.
Figure 25:
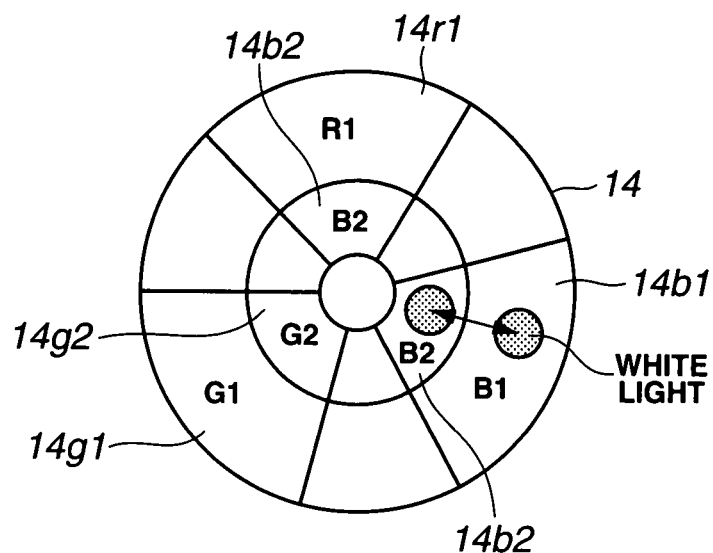
FIG. 25 is a configuration diagram showing a configuration of a first variation of the rotating filter of FIG. 1.
Figure 26:
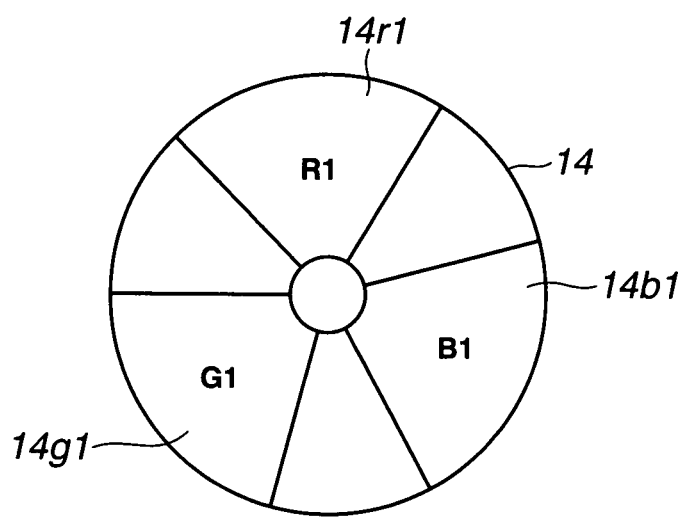
FIG. 26 is a configuration diagram showing a configuration of a second variation of the rotating filter of FIG. 1.
Figure 27:
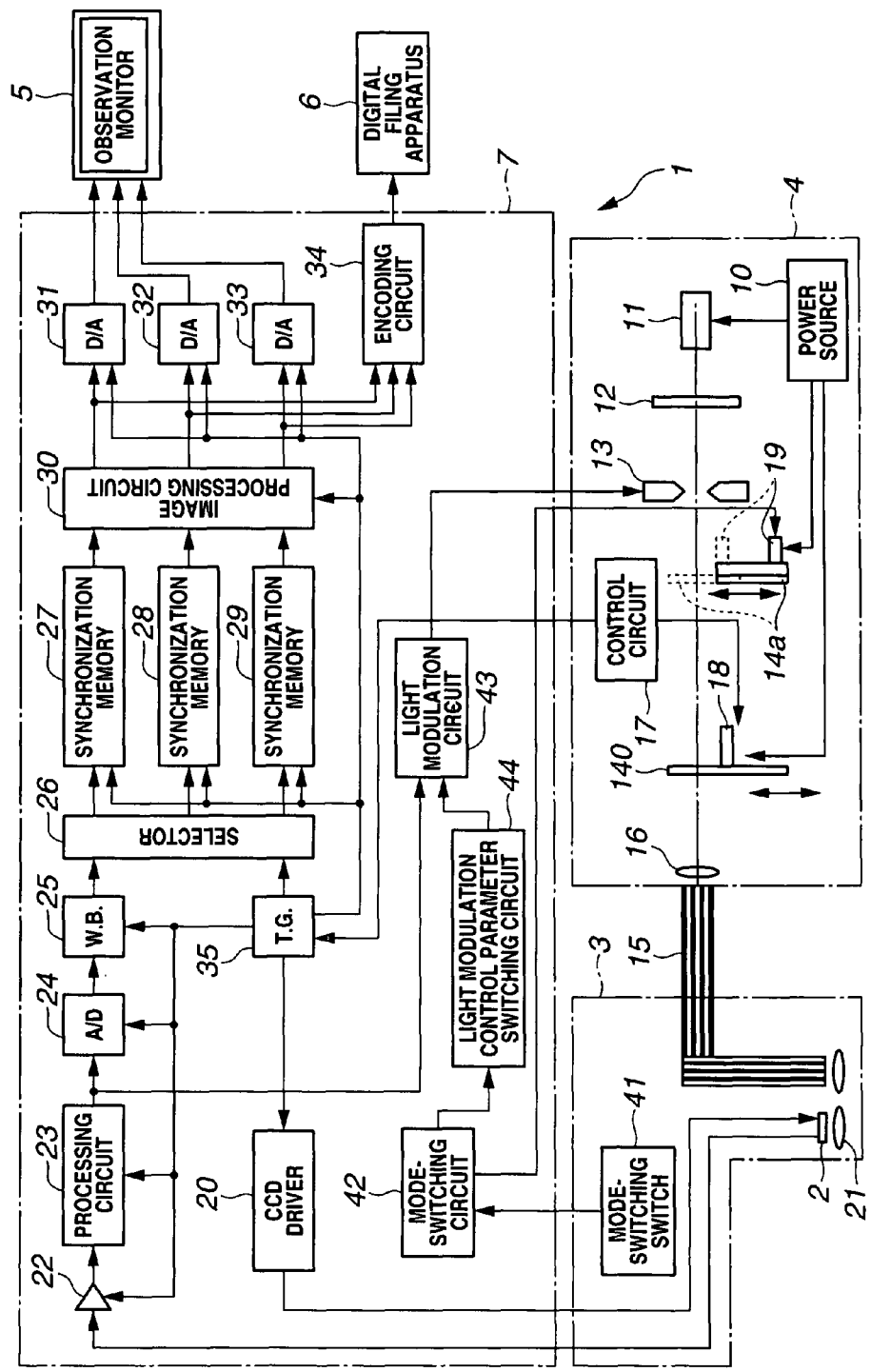
FIG. 27 is a diagram showing a configuration of an endoscope apparatus when the rotating filter of FIG. 26 is used.

FIGS. 1 through 27 are related to a first embodiment of the present invention. FIG. 1 is a block diagram showing a configuration of an endoscope apparatus; FIG. 2 is a configuration diagram showing a configuration of the rotating filter of FIG. 1; FIG. 3 is a diagram showing the spectral characteristics of a first filter group of the rotating filter of FIG. 2; FIG. 4 is a diagram showing the spectral characteristics of a second filter group of the rotating filter of FIG. 2; FIG. 5 is a diagram showing the layered structure of a living tissue observed via the endoscope apparatus of FIG. 1; FIG. 6 is a diagram illustrating the access state in the direction of the layers of a living tissue of illumination light from the endoscope apparatus of FIG. 1; FIG. 7 is a first diagram showing the respective band images resulting from surface-sequential light permeating the first filter group of FIG. 3; FIG. 8 is a second diagram showing the respective band images resulting from surface-sequential light permeating the first filter group of FIG. 3; FIG. 9 is a third diagram showing the respective band images resulting from surface-sequential light permeating the first filter group of FIG. 3; FIG. 10 is a first diagram showing the respective band images resulting from surface-sequential light permeating the second filter group of FIG. 4; FIG. 11 is a second diagram showing the respective band images resulting from surface-sequential light permeating the second filter group of FIG. 4; FIG. 12 is a first diagram illustrating a manufacturing method of the second filter group of FIG. 4; FIG. 13 is a second diagram illustrating a manufacturing method of the second filter group of FIG. 4; FIG. 14 is a third diagram illustrating a manufacturing method of the second filter group of FIG. 4; FIG. 15 is a fourth diagram illustrating a manufacturing method of the second filter group of FIG. 4; FIG. 16 is a fifth diagram illustrating a manufacturing method of the second filter group of FIG. 4; FIG. 17 is a sixth diagram illustrating a manufacturing method of the second filter group of FIG. 4; FIG. 18 is a seventh diagram illustrating a manufacturing method of the second filter group of FIG. 4; FIG. 19 is a block diagram showing a configuration of a variation of the endoscope apparatus of FIG. 1; FIG. 20 is a diagram showing the spectral transmission characteristics of the narrowband interference filter of FIG. 19; FIG. 21 is a diagram showing the spectral transmission characteristics of a first interference membrane filter for realizing the narrowband interference filter of FIG. 19; FIG. 22 is a diagram showing the spectral transmission characteristics of a second interference membrane filter for realizing the narrowband interference filter of FIG. 19; FIG. 23 is a diagram showing the spectral transmission characteristics of a third interference membrane filter for realizing the narrowband interference filter of FIG. 19; FIG. 24 is a diagram showing the spectral transmission characteristics of a variation of the narrowband interference filter of FIG. 20; FIG. 25 is a configuration diagram showing a configuration of a first variation of the rotating filter of FIG. 1; FIG. 26 is a configuration diagram showing a configuration of a second variation of the rotating filter of FIG. 1; and FIG. 27 is a diagram showing a configuration of an endoscope apparatus when the rotating filter of FIG. 26 is used.

As shown in FIG. 1, an endoscope apparatus 1 of the present embodiment includes an electronic endoscope 3, which is inserted into a body cavity, and has a CCD 2 as image-capturing means for capturing an image of a tissue inside the body cavity; a light-source apparatus 4 for supplying an illumination light to the electronic endoscope 3; and a video processor 7, which performs signal processing of an image-capturing signal from the CCD 2 of the electronic endoscope 3, and displays the endoscopic image on an observation monitor 5, and encodes the endoscopic image and outputs the same to an image filing apparatus 6 as a compressed image.

The light-source apparatus 4 includes a xenon lamp 11 for emitting an illumination light; a heat cutting filter 12 for blocking the heat of a white light; a diaphragm device 13 for controlling the quantity of light of a white light via the heat cutting filter 12; a rotating filter 14 for making the illumination light a surface-sequential light; a condensing lens 16 for condensing the surface-sequential light via the rotating filter 14 on the incident surface of a light guide 15 arranged inside the electronic endoscope 3; and a control circuit 17 for controlling the rotation of the rotating filter 14.

The rotating filter 14, as shown in FIG. 2, is constituted in a disk shape, and has a dual structure centered around an axis of rotation, an R1 filter section 14r1, a G1 filter section 14g1, and a B1 filter section 14b1, which constitute a first filter group for outputting surface-sequential light of overlapping spectral characteristics, which, as shown in FIG. 3, is well suited to color reproduction, are arranged in the outer radial part, and a G2 filter section 14g2, a B2 filter section 14b2, and a shading filter section 14Cut, which constitute a second filter group for outputting narrowband surface-sequential light of two bands of discrete spectral characteristics, capable, as shown in FIG. 4, of extracting the desired layer tissue information, are arranged in the inner radial part.

Furthermore, it is supposed, for example, that the wavelength region $\lambda 11$ through $\lambda 12$ of the B2 filter section 14b2 is between 405 and 425 nm, and the wavelength region $\lambda 21$ through $\lambda 22$ of the G2 filter section 14g2 is between 530 and 550 nm.

Furthermore, the wavelength region λ11 through λ12 may be between 400 and 440 nm, and the wavelength region λ21 through λ22 may be between 530 and 550 nm.

Then, as shown in FIG. 1, a control circuit 17 drives and controls a rotating filter motor 18, thereby rotating the rotating filter 14, and a mode switching motor 19 moves the rotating filter 14 radially (moves the rotating filter 14 perpendicular to the optical path, and selectively moves the first filter group and second filter group of the rotating filter 14 into the optical path) in accordance with a control signal from a mode switching circuit 42 inside the video processor 7, which will be explained hereinbelow.

Furthermore, power is supplied to the xenon lamp 11, diaphragm device 13, rotating filter motor 18, and mode switching motor 19 from a power unit 10.

The video processor 7 includes a CCD drive circuit 20 for driving the CCD 2; an amplifier 22 for amplifying an image-capturing signal, which is an image of a body cavity tissue captured by the CCD 2 through an objective optical system 21; a processing circuit 23, which performs correlated double sampling (CDS) and noise removal for an image-capturing signal through the amplifier 22; an A/D converter 24 for converting an image-capturing signal that has passed through the processing circuit 23 to digital signal image data; a white balance circuit (W.B.) 25 for performing white balance processing on the image data from the A/D converter 24; a selector 26 and synchronization memories 27, 28, 29 for synchronizing surface-sequential light using the rotating filter 14; an image processing circuit 30 for reading out the respective image data of the surface-sequential light stored in the synchronization memories 27, 28, 29, and performing gamma correction processing, contour highlight processing, and color processing; D/A circuits 31, 32, 33 for converting image data from the image processing circuit 30 to analog signals; an encoding circuit 34 for encoding image data from the image processing circuit 30; and a timing generator (T.G.) 35 for inputting from the control circuit 17 of the light-source apparatus 4 a synchronization signal synchronized to the rotation of the rotating filter 14, and outputting various timing signals to the above-described respective circuits.

Further, a mode-switching switch 41 is provided in the electronic endoscope 2, and the output of the mode-switching switch 41 is outputted to the mode switching circuit 42 inside the video processor 7. The mode switching circuit 42 of the video processor 7 outputs a control signal to light modulation circuit 43, a light modulation control parameter switching circuit 44, and the mode switching motor 19 of the light-source apparatus 4. The light modulation control parameter switching circuit 44 outputs a light modulation control parameter corresponding to the first filter group and the second filter group of the rotating filter 14 to the light modulation circuit 43, and the light modulation circuit 43 controls the diaphragm device 13 of the light-source apparatus 4 based on a control signal from the mode switching circuit 42 and a light modulation control parameter from the light modulation control parameter switching circuit 44 so as to control optimum brightness.

Next, the operation of the endoscope apparatus of the present embodiment, which is constituted, will be explained.

As shown in FIG. 5, in most cases, for example, body cavity tissue 51 has an absorbent distributed structure of blood vessels and the like that differ in the depth direction. In the vicinity of the superficial portion of the mucous membrane mainly capillary vessels 52 are distributed in large numbers, and in the intermediate layer, which is deeper than this layer, blood vessels 53 that are larger than capillary vessels are distributed in addition to capillary vessels, and in a yet deeper layer, even larger blood vessels 54 are distributed.

Meanwhile, the invasion depth in the depth direction of light relative to a body cavity tissue 51 is dependent on the wavelength of the light, and when illumination light including the visible region is a short wavelength like that of blue (B), as shown in FIG. 6, the light only penetrates as far as the superficial layer as a result of the absorption characteristics and scattering characteristics of the living tissue, is subjected to absorption and scattering in that depth range, and the light that exits from the surface is observed. Further, in the case of green (G) light, which has a longer wavelength than blue (B) light, the light penetrates deeper than the range to which the blue (B) light penetrated, is subjected to absorption and scattering in that range, and the light that exists from the surface is observed. And red (R) light, which has a longer wavelength than green (G) light, reaches an even deeper range.

In ordinary observation, the mode switching circuit inside the video processor 7 controls the mode switching motor 19 via a control signal such that the R1 filter section 14r1, G1 filter section 14g1, and B1 filter section 14b1, which are the first filter group of the rotating filter 14, are located in the optical path of the illumination light.

Since the respective wavelength regions of the R1 filter section 14r1, G1 filter section 14g1, and B1 filter section 14b1 overlap one another as shown in FIG. 3 during ordinary observation of the body cavity tissue 51, (1) a band image including shallow layer and intermediate layer tissue information, which includes plenty of tissue information of the shallow layer as shown in FIG. 7, is captured in an image-capturing signal, which is an image captured by the CCD 2 via the B1 filter section 14b1; (2) also, a band image including shallow layer and intermediate layer tissue information, which includes plenty of tissue information of the intermediate layer as shown in FIG. 8, is captured in an image-capturing signal, which is an image captured by the CCD 2 via the G1 filter section 14g1; and (3) in addition, a band image including intermediate layer and deep layer tissue information, which includes plenty of tissue information of the deep layer as shown in FIG. 9, is captured in an image-capturing signal, which is an image captured by the CCD 2 via the R1 filter section 14r1.

Then, an endoscopic image of a desired or natural color reproduction can be obtained as the endoscopic image by the video processor 7 synchronizing the RGB image-capturing signals and performing signal processing.

By contrast, if the mode-switching switch 41 of the electronic endoscope 3 is pressed, the signal is inputted to the mode switching circuit 42 of the video processor 7. By outputting a control signal to the mode switching motor 19 of the light-source apparatus 4, the mode switching circuit 42 drives the rotating filter 14 relative to the optical path so as to move the first filter group of the rotating filter 14, which was in the optical path at ordinary observation, and position the second filter group in the optical path.

Because the G2 filter section 14g2, B2 filter section 14b2, and shading filter section 14Cut change the illumination light to two-band narrowband surface-sequential light of discrete spectral characteristics, and their respective wavelength regions do not overlap as shown in FIG. 4 when body cavity tissue 51 is being observed under narrowband light using the second filter group, (4) a band image including tissue information of the shallow layer as shown in FIG. 10 is captured in the image-capturing signal, which is an image captured by the CCD 2 via the B2 filter section 14b2; and (5) a band image including tissue information of the intermediate layer as shown in FIG. 11 is also captured in the image-capturing signal, which is an image captured by the CCD 2 via the G2 filter section 14g2.

As is clear from FIGS. 3 and 4, since the quantity of light transmitted by the second filter group decreases relative to the quantity of light transmitted by the first filter group due to the narrowing of the band thereof, the light modulation control parameter switching circuit 44 outputs to the light modulation circuit 43 a light modulation control parameter corresponding to the first filter group and second filter group of the rotating filter 14, and the light modulation circuit 43 controls the diaphragm device 13, thereby obtaining sufficiently bright image data even when observation is being carried out under narrowband light.

Further, the image processing circuit 30, when colorizing an image at narrowband-light observation, generates an RGB three-channel color image as R-channel←G-narrowband image data, G-channel←B-narrowband image data, and B-channel←B-narrowband image data.

That is, the image processing circuit 30 generates RGB three-channel color images (R', G', B') relative to G-narrowband image data (G) and B-narrowband image data (B).

$$\begin{pmatrix} R' \\ G' \\ B' \end{pmatrix} = \begin{pmatrix} h11 & h12 \\ h21 & h22 \\ h31 & h32 \end{pmatrix} \begin{pmatrix} G \\ B \end{pmatrix} \quad (1)$$

For example, it is supposed that h11=1, h12=0, h21=0, h22=1.2, h31=0, and h32=0.8.

Since a conventional three-band narrowband surface-sequential light like that shown in FIG. 12 is obtained, the vapor deposition of an interference membrane filter having spectral transmittance characteristics like those shown in FIGS. 13 and 14 for B narrowband light, the vapor deposition of an interference membrane filter having spectral transmittance characteristics like those shown in FIGS. 15 and 16 for G narrowband light, and the vapor deposition of an interference membrane filter having spectral transmittance characteristics like those shown in FIGS. 17 and 18 for R narrowband light become necessary, but in the present embodiment, the B2 filter section 14b2 is manufactured by the vapor deposition of an interference membrane filter having spectral transmittance characteristics like those shown in FIGS. 13 and 14, and the G2 filter section 14g2 is manufactured by the vapor deposition of an interference membrane filter having spectral transmittance characteristics like those shown in FIGS. 15 and 16.

When an optical filter is manufactured like this, ordinarily the problem is that in most cases this is done by vapor deposition of a multi-layered interference membrane filter, and, in the manufacturing method, to make the spectral transmittance characteristics narrowband, a number of membranes must be deposited, thus raising costs and increasing the thickness of the filter. However, in the present embodiment, tissue information of a desired depth in the vicinity of the superficial portion of the mucous membrane can be obtained by vapor depositioning the smallest multi-layered interference membrane filter possible, and, for example, can be used in the identification and diagnosis of early-stage cancer and other such diseases that disturb the cellular arrangement in the vicinity of the superficial portion of the mucous membrane.

Furthermore, for the endoscope apparatus 1 of the above-described embodiment, an example of a surface-sequential-type endoscope apparatus, in which a light-source apparatus 4 supplies surface-sequential light, and a video processor 7 synchronizes surface-sequential image data to create an image was used in the explanation, but the first embodiment is not limited to this, and a synchronous-type endoscope apparatus is also applicable.

That is, as shown in FIG. 19, a synchronous-type endoscope apparatus 1a, including a light-source apparatus 4a for supplying white light; an electronic endoscope 3a, which comprises a color chip 100 on the front face of the image-capturing surface of the CCD 2; and a video processor 7a for carrying out signal processing of an image-capturing signal from the electronic endoscope 3a, can also apply the present embodiment.

In the light-source apparatus 4a, the quantity of light of the white light from the xenon lamp 11 by way of the heat cutting filter 12 is controlled by the diaphragm device 13, and outputted to the incident surface of the light guide 15 disposed inside the electronic endoscope 3a. A narrowband interference filter 14a, which converts the white light to two bands of narrowband light A1, A2 of discrete spectral characteristics as shown in FIG. 20 is removably provided in the optical path of the white light.

Furthermore, the narrowband light A1 and narrowband light A2 of the narrowband interference filter 14a can be realized by the vapor depositioning of a plurality of interference membrane filters having spectral transmittance characteristics like those shown in FIGS. 21 through 23. Here, it is supposed that the wavelength region of narrowband light A1 and the wavelength region of narrowband light A2 include the following respective combinations:

Narrowband light A1=405 through 425 nm, narrowband light A2=530 through 550 nm
Narrowband light A1=405 through 425 nm, narrowband light A2=490 through 510 nm
Narrowband light A1=405 through 425 nm, narrowband light A2=440 through 460 nm
Narrowband light A1=440 through 460 nm, narrowband light A2=530 through 550 nm However, the near ultraviolet region and near infrared region can also be included.

In the electronic endoscope 3a, an image of a body cavity tissue 51 is captured by the CCD 2 through a color chip 100.

In the video processor 7a, image data from the A/D converter 24 is separated into a luminance signal Y and color difference signals Cr, Cb by a Y/C separation circuit 101, converted to RGB signals by the RGB matrix circuit 102, and outputted to the white balance circuit 25. The rest of the configuration and operations are the same as the endoscope apparatus of FIG. 1.

Further, since the light of the R narrowband component is not irradiated onto the body cavity tissue 51, tissue information resulting from R narrowband light is not included in the data obtained at narrowband-light observation, having the effect of enabling the acquisition of tissue information of a desired depth in the vicinity of a superficial portion of the mucous membrane without separating the image information using the light of the R narrowband component, and facilitating data processing.

Furthermore, as in the spectral transmittance characteristics of the B2 filter section 14b2 and G2 filter section 14g2 in the second filter group of the rotating filter 14 shown in FIG. 24, the spectral product of the G narrowband light can be smaller than the spectral product of the B narrowband light. The same holds true for narrowband light A1 (equivalent to B narrowband light) and narrowband light A2 (equivalent to G narrowband light) of the narrowband interference filter 14a.

Alternatively, the spectral product SG of the G narrowband light is made smaller than the spectral product SB of the B narrowband light in the incident light to the CCD 2. For example, it can be 1.10≦SG/SB≦0.35.

SG=∫$^G$S(λ)dλ
SB=∫$^B$S(λ)dλ
S(λ)=Lamp(λ)×LIRCut(λ)×NBIFilter(λ)×LG(λ)×IRCut(λ)×YagCut(λ)

Lamp(λ): spectral characteristics of the lamp

LIRCut(λ): spectral characteristics of the heat cutting filter inside the light-source apparatus NBIFilter(λ): spectral characteristics of the narrowband interference filter (NBI filter)

LG(λ): spectral characteristics of the light guide

IRCut(λ): spectral characteristics of the infrared light cutting filter inside the endoscope apparatus YagCut(λ): spectral characteristics of the laser light cutting filter inside the endoscope apparatus Here ∫$^G$, ∫$^B$ indicate integration operations in the wavelength regions of the respective G narrowband light and B narrowband light.

In the past, the design of the transmittance of the narrowband interference filter (NBI filter) was done such that the white balance correction value became practically equivalent in RGB in order to suppress the noise in the R and B signals when photographing a white cap (standard white plate).

However, since absorbance by the Hb (hemoglobin) when observing a living mucous membrane is higher with B narrowband light than with G narrowband light, the B signal becomes relatively dark. In order to enhance the visibility of the mucous membrane data of the NBI using color conversion processing, it is necessary to make the brightness of the G and B signals practically equal, but the problem is that the noise of the B signal becomes conspicuous due to the need to increase the gain of the B signal. Furthermore, if transmittance adjustment is not proper in the complementary color filter CCD, the saturation points of Y/Cr/Cb differ for each signal, and color reproducibility deteriorates in RGB signals converted from YCrCb signals via a linear operation.

Accordingly, making the spectral product of G narrowband light smaller than the spectral product of B narrowband light enables the realization of good image quality by NBI.

That is, lowering the transmittance of the G narrowband than that of the B narrowband makes it possible to reduce the difference in the G and B signal outputs when observing a living mucous membrane, and since the gain of the B signal can be reduced as a result of this, noise can be suppressed.

Further, since the saturation point differences of Y/Cr/Cb can be lessened when observing a living mucous membrane, it becomes possible to widen the range within which brightness-related signal output linearly changes in the post-conversion signals, with the result that the range of color reproducibility also broadens.

Furthermore, the second filter group of the rotating filter 14 in FIG. 1 includes a G2 filter section 14g2, a B2 filter section 14b2, and a shading filter section 14Cut (refer to FIG. 2), but as shown in FIG. 25, a B2 filter section 14b2 can also be arranged in the shading filter section 14Cut part, such that the second filter group constitutes a B2 filter section 14b2, a G2 filter section 14g2, and a B2 filter section 14b2. By constituting the second filter group like this, image-capturing by the CCD 2 via the B2 filter section 14b2 is implemented twice in a single filter period and the image-capturing signal is processed, making it possible to improve the brightness of the narrowband B image, for example, by performing B addition processing, and to enhance the signal-to-noise ratio (SN) by averaging.

Further, the light-source apparatus 4 may be constituted by constituting the dual-structure rotating filter 14 in FIG. 1 as a rotating filter 140 with only a first filter group, which comprises an R1 filter section 14r1, G1 filter section 14g1, and B1 filter section 14b1 of the single structure shown in FIG. 26, and, as shown in FIG. 27, removably arranging the narrowband interference filter 14a shown in FIG. 19 in the optical axis at the first stage of the incidence optical axis of the rotating filter 140. In this case, ordinary surface-sequential light observation and narrowband surface-sequential light observation become possible using the video processor 7 of the configuration shown in FIG. 1 without having to provide a color chip 100 on the front face of the CCD 2.

Second Embodiment

Figure 28:
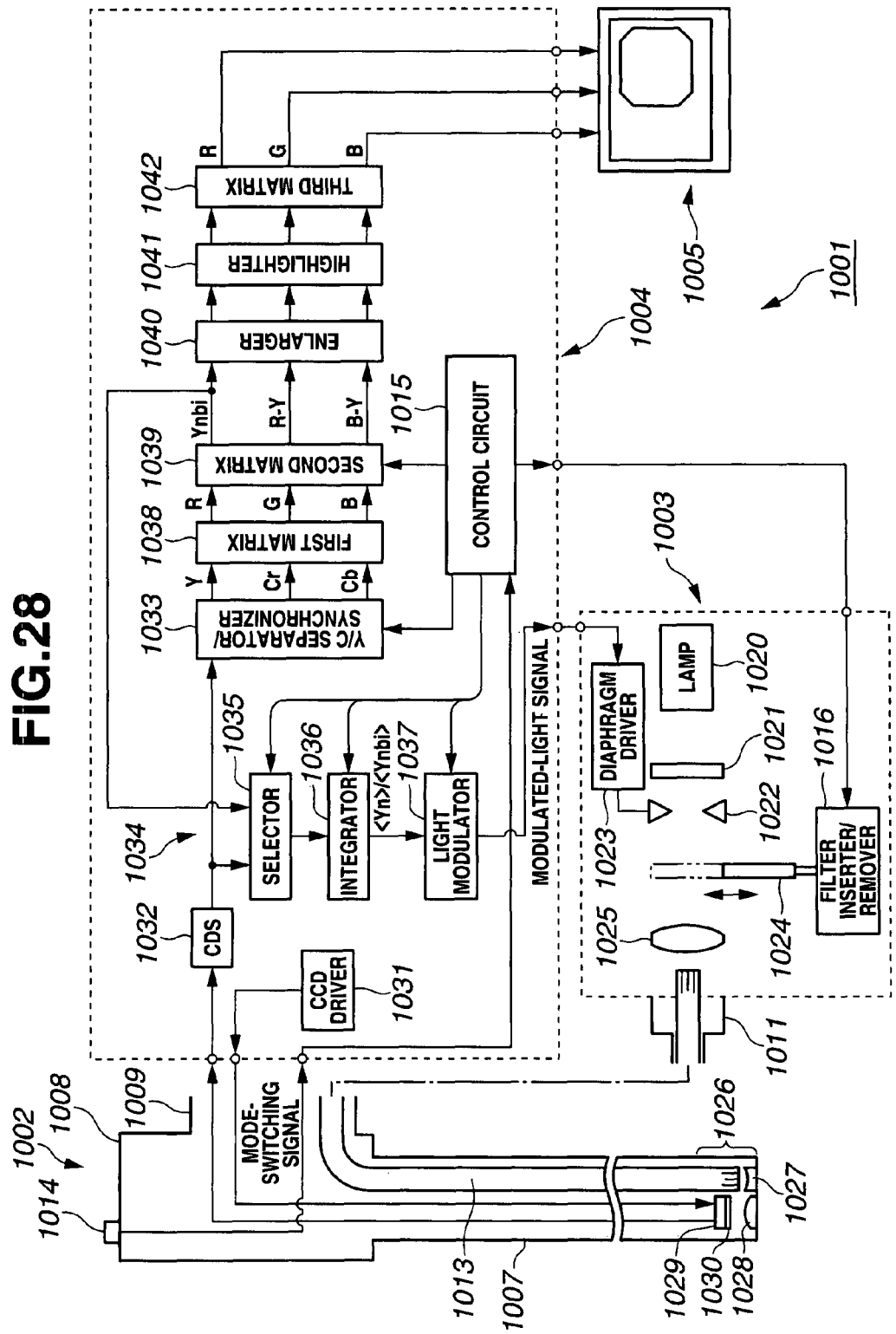
FIG. 28 is a block diagram showing a configuration of an endoscope apparatus according to a second embodiment of the present invention.
Figure 29:
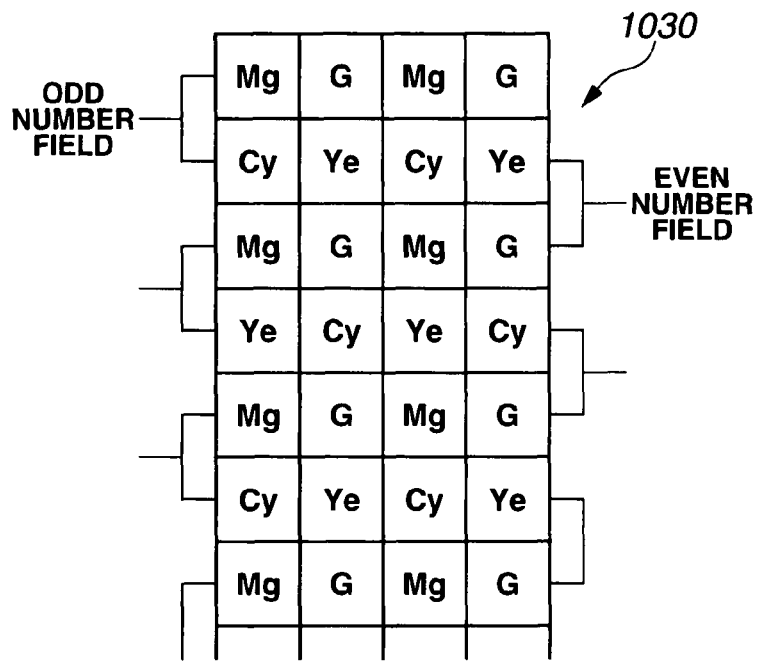
FIG. 29 is a diagram showing a configuration of a filter array of color separating filters provided in a solid-state image-capturing device.
Figure 30:
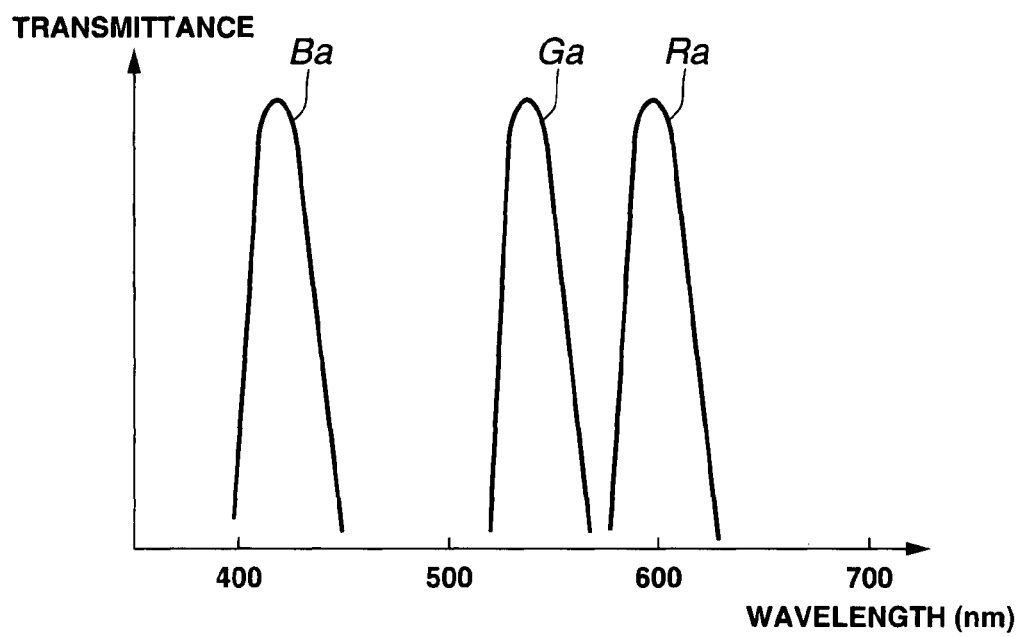
FIG. 30 is a characteristic diagram showing the spectral characteristics of a narrowband filter.
Figure 31:
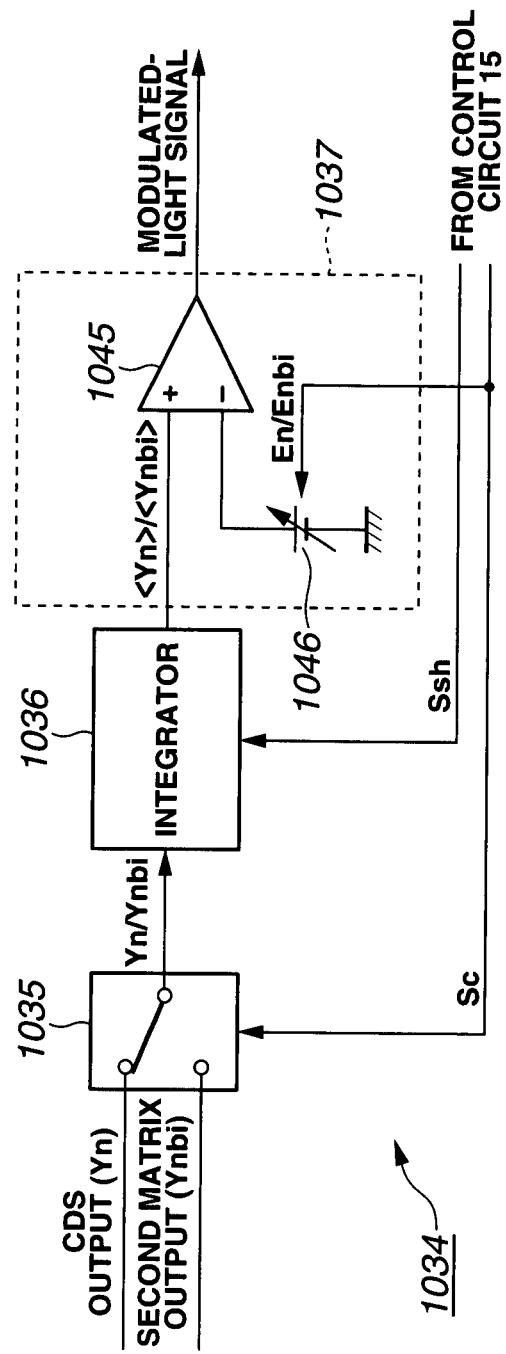
FIG. 31 is a diagram showing an example of a configuration of a modulated-light signal generation circuit.
Figure 32:
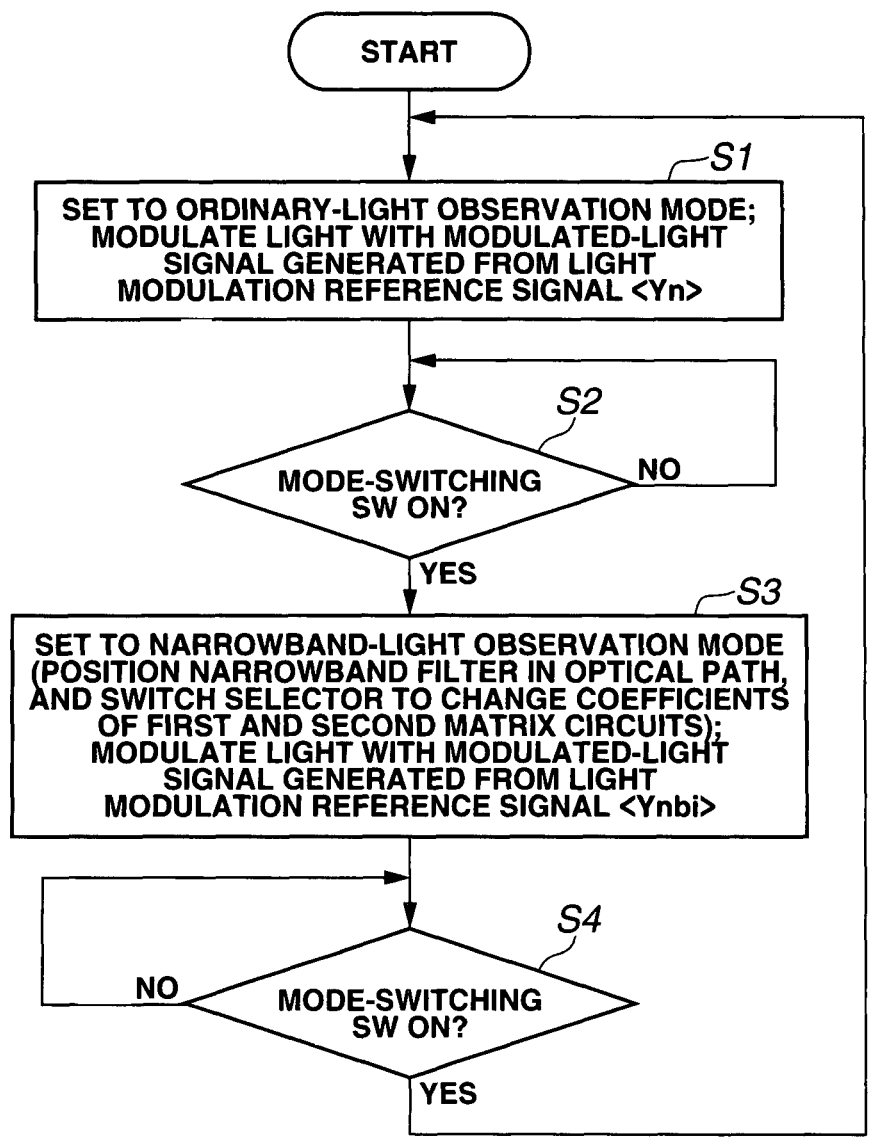
FIG. 32 is a flowchart for explaining the operation of the second embodiment.
Figure 33:
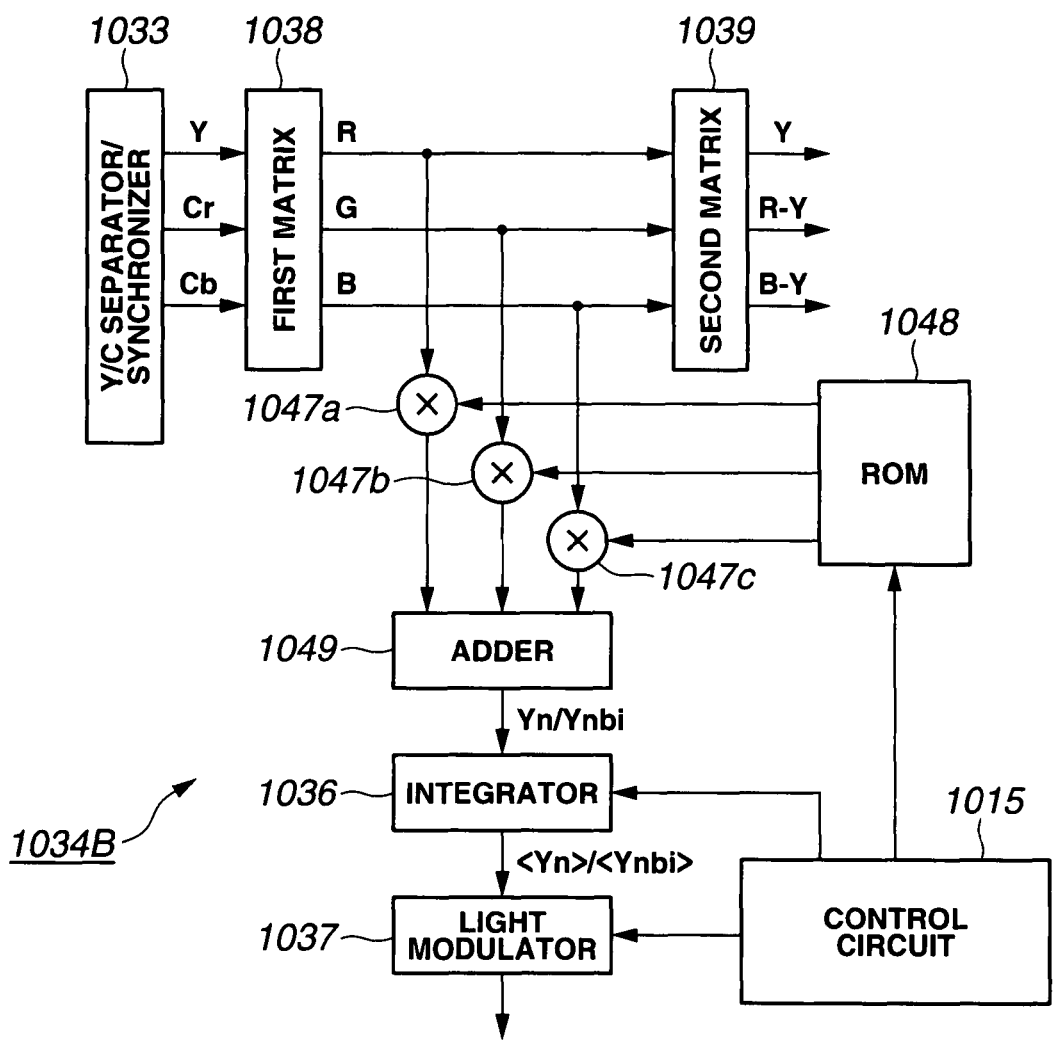
FIG. 33 is a diagram showing a configuration of peripheral portions of the modulated-light signal generation circuit of a variation of the second embodiment.
Figure 34:
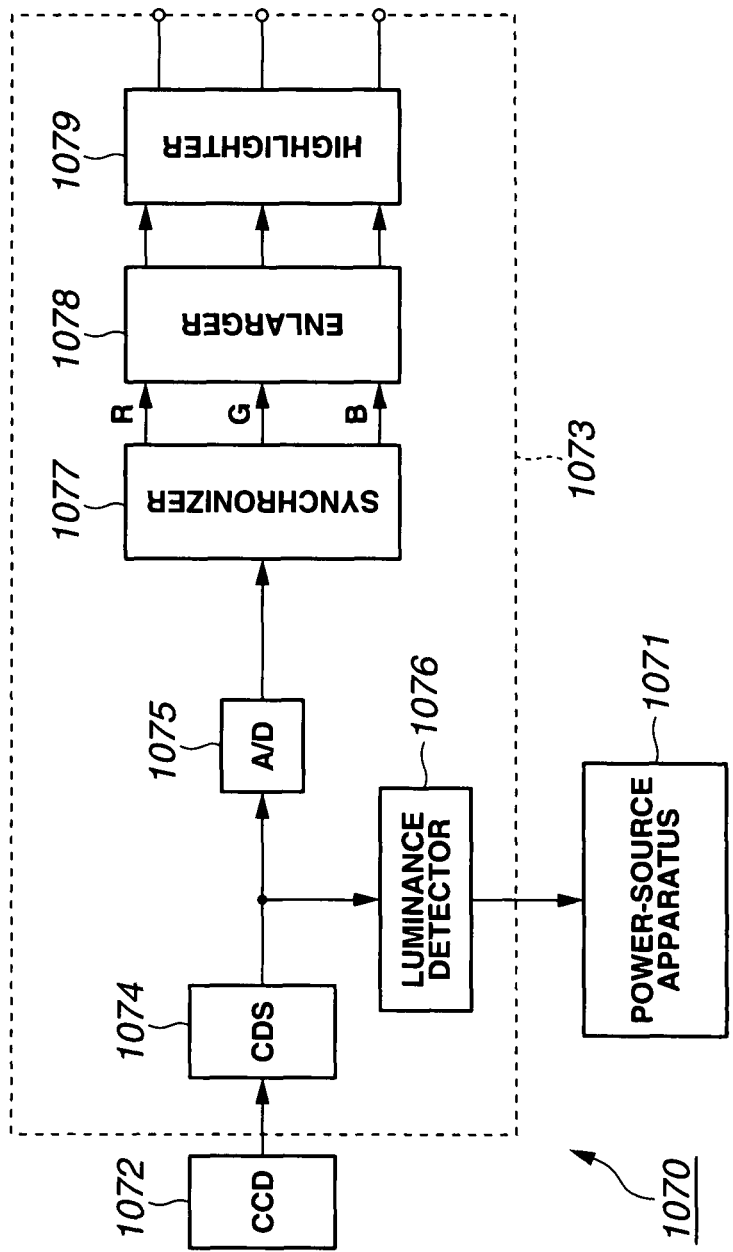
FIG. 34 is a simplified block diagram of a conventional surface-sequential-type endoscope apparatus.
Figure 35:
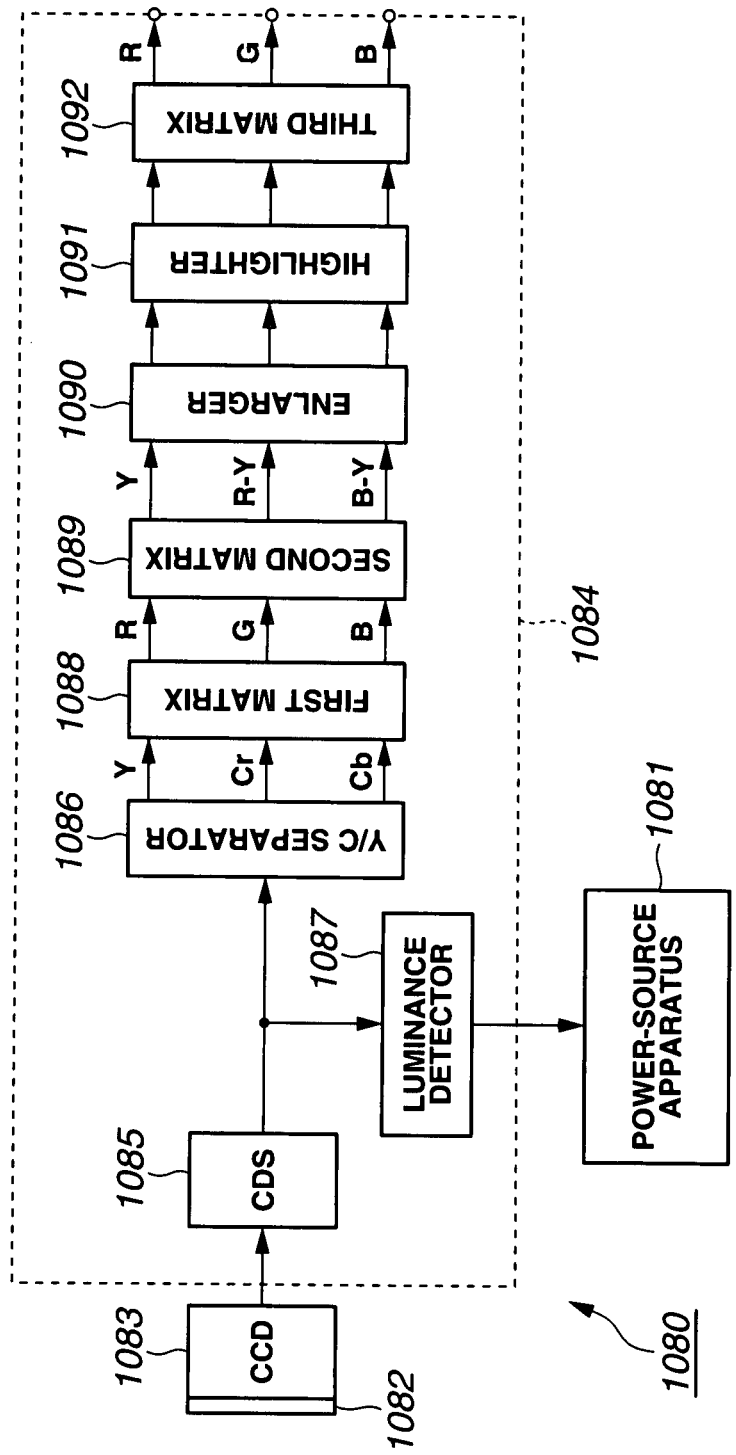
FIG. 35 is a simplified block diagram of a conventional synchronous-type endoscope apparatus.

FIGS. 28 through 35 are related to a second embodiment of the present invention. FIG. 28 shows a configuration of an endoscope apparatus according to a second embodiment of the present invention; FIG. 29 shows a configuration of a filter array of color separating filters provided in a solid-state image-capturing device; FIG. 30 shows the spectral characteristics of a narrowband filter; FIG. 31 shows a configuration of modulated-light signal generation circuit; FIG. 32 shows a flowchart for explaining the operation of the present embodiment; FIG. 33 shows a configuration of peripheral portions of the modulated-light signal generation circuit in a variation of the second embodiment; FIG. 34 shows a configuration of a simplified block diagram of a conventional surface-sequential-type endoscope apparatus; and FIG. 35 shows a simplified block diagram of a conventional synchronous-type endoscope apparatus.

The electronic endoscope including image-capturing means has come into widespread use in recent years in a variety of endoscopic examinations.

Further, an endoscope apparatus, which obtains a narrowband-light observation image using a narrowband illumination light has been commercialized recently.

FIG. 34 shows a simplified configuration of a conventional endoscope apparatus 1070, which employs a surface-sequential system, and can obtain an ordinary-light observation image and a narrowband-light observation image.

A light-source apparatus 1071 illuminates an object by emitting broadband R, G and B surface-sequential illumination light at ordinary-light observation, and emitting narrowband R, G and B surface-sequential illumination light at narrowband-light observation.

The illuminated object is surface-sequentially captured as an image by a CCD 1072. The CCD 1072 does not have a color filter for color separation provided on the image-capturing surface of the CCD, that is, it is a monochrome CCD. A surface-sequential image-capturing signal, which has undergone photoelectric transfer by the CCD 1072, is inputted to a CDS circuit 1074 of a video processing circuit 1073, and after a signal component has been extracted, is inputted to an A/D conversion circuit 1075, and, in addition, is inputted to a luminance detection circuit 1076.

A surface-sequential analog signal, which is inputted to the A/D conversion circuit 1075, is converted to a digital signal, and thereafter inputted to a synchronization circuit 1077 and converted to a synchronized RGB signal. The RGB signal outputted from the synchronization circuit 1077 is subjected to enlargement processing in an enlargement circuit 1078, after which it is inputted to a highlighting circuit 1079, and subsequent to contour highlighting, is outputted from an output terminal to a monitor not shown in the figure, and an endoscopic image of either an ordinary-light observation mode or a narrowband-light observation mode is displayed in color.

Further, the luminance detection circuit 1076 integrates inputted surface-sequential R, G and B signals, generates a light modulation reference signal, and outputs a signal of the difference with the reference brightness value to the light-source apparatus 1071 as a modulated-light signal. Then, the light-source apparatus 1071 adjusts the quantity of illumination light in accordance with the modulated-light signal.

In the prior art, it is possible to properly modulate light using a light modulation reference signal generated at ordinary-light observation, but since the illumination light constitutes a narrowband at narrowband-light observation, the quantity of illumination light is reduced, and appropriate light modulation cannot be carried out with the same light modulation reference signal generating means as that used at ordinary-light observation.

Further, at ordinary-light observation, the brightness of the image can be regulated at a luminance level, which comprises all the respective color component signals, but the drawback is that, since specified color signals can constitute important image data at narrowband-light observation, generating a light modulation reference signal the same as at ordinary-light observation does not enable proper light modulation across a broad range of light quantities.

That is, light modulation can be carried out in accordance with the average value of the respective signals at ordinary-light observation, but the disadvantage is that, since the image data of specified color components is important at narrowband-light observation, it is not possible to carry out proper light modulation simply using the average value of the respective signals.

Furthermore, a prior art endoscope apparatus, which employs a surface-sequential system, and is capable of obtaining an ordinary-light observation image and a narrowband-light observation image, for example, is disclosed in Japanese Patent Laid-open No. 2002-95635. In the official gazette, a light modulation control parameter is changed in a common light modulation circuit at ordinary-light observation and at narrowband-light observation.

According to the prior art of the official gazette, light modulation can be improved more than in the case of the circuit configuration of FIG. 34, but the disadvantage is that it is difficult to properly modulate light at narrowband-light observation even when the light modulation control parameter is changed due to the fact that a common light modulation circuit is being employed.

Meanwhile, FIG. 35 shows a simplified configuration of a conventional synchronous-type endoscope apparatus 1080 that performs an ordinary-light observation and a narrowband-light observation using an endoscope equipped with image-capturing means including an optical filter.

A light-source apparatus 1081 generates an illumination light of white light at ordinary-light observation, and generates an illumination light of R, G and B narrowband light at narrowband-light observation, and illuminates an object.

The illuminated object is captured as an image by a CCD 1083 to which a color filter 1082 is provided on the image-capturing surface. An image-capturing signal, which has undergone photoelectric transfer by the CCD 1083, is inputted to a CDS circuit 1085 of a video processing circuit 1084, and after a signal component has been extracted, is inputted to Y/C separation circuit 1086, and, in addition, is inputted to a luminance detection circuit 1087.

The image-capturing signal, which was inputted to the Y/C separation circuit 1086, is separated into a luminance signal Y and color difference signals Cr and Cb, and thereafter is inputted to a first matrix circuit 1088 and converted to an RGB signal. The RGB signal is inputted to a second matrix circuit 1089, and converted to luminance signal Y and color difference signals R-Y and B-Y.

The luminance signal Y and color difference signals R-Y and B-Y are subjected to enlargement processing by an enlargement circuit 1090, and thereafter are inputted to a highlighting circuit 1091, where they undergo contour highlighting. After that, these signals are inputted to a third matrix circuit 1092 and converted to RGB signals (three primary color signals), and then outputted from an output terminal to a monitor not shown in the figure, and an endoscopic image of either an ordinary-light observation mode or a narrowband-light observation mode is displayed in color.

Further, the luminance detection circuit 1087 integrates an inputted CDS output signal and the like, computes an average value for the CDS output signal, generates a light modulation reference signal, and outputs a signal of the difference with the reference brightness value to the light-source apparatus 1081 as a modulated-light signal. Then, the light-source apparatus 1081 adjusts the quantity of illumination light in accordance with the modulated-light signal.

In the case of the synchronous system shown in FIG. 35, the disadvantage is the same as was explained in the case of the surface-sequential system, that is, it is difficult to properly modulate light at narrowband-light observation because a light modulation reference signal is generated by a common circuit configuration at ordinary-light observation and at narrowband-light observation.

In the second embodiment and in the third embodiment, which will be explained hereinbelow, an object is to provide an endoscope apparatus capable of properly modulating light during both ordinary-light observation and narrowband-light observation.

As shown in FIG. 28, an endoscope apparatus 1001 according to the second embodiment comprises an electronic endoscope (hereinafter, abbreviated simply as endoscope) 1002 for being inserted into a body cavity and performing an endoscopic examination; a light-source apparatus 1003 for supplying an illumination light to the endoscope 1002; a video processor 1004 for driving image-capturing means incorporated into the endoscope 1002, and for performing signal processing to an output signal of image-capturing means; and a monitor 1005 for displaying an endoscopic image captured by image-capturing means in accordance with the inputting of a video signal outputted from the video processor 1004.

The endoscope 1002 comprises a long, thin insertion unit 1007; an operation unit 1008 provided at the back end of the insertion unit 1007; and a universal cable 1009 extending from the operation unit 1008. A light-guide connector 1011 at the distal end of the universal cable 1009 is detachably connected to the light-source apparatus 1003, and a signal connector is detachably connected to the video processor 1004.

A light guide 1013 for transmitting illumination light is inserted into the above-mentioned insertion unit 1007, and illumination light from the light-source apparatus 1003 is supplied to the light guide 1013 by connecting a light-guide connector 1011 at the hand-side end of the light guide 1013 to the light-source apparatus 1003.

The light-source apparatus 1003 emits white light (visible region) illumination light as ordinary illumination light when in the ordinary-light observation mode, and supplies to the light guide 1013, and emits narrowband illumination light when in the narrowband-light observation mode, and supplies to the light guide 1013.

Instructions for switching the ordinary-light observation mode and the narrowband-light observation mode, for example, can be carried out via a scope switch or other such mode-switching switch 1014 provided on the operation unit 1008 of the endoscope 1002. Furthermore, the mode-switching switch 1014, instead of being constituted as a scope switch provided on the endoscope 1002, can also be constituted by a foot switch, can be provided on the front panel of the video processor 1004, or can be constituted by a keyboard not shown in the figure.

A mode switching signal from the mode-switching switch 1014 is inputted to a control circuit 1015 inside the video processor 1004, and when the mode switching signal is inputted, the control circuit 1015 selectively switches between ordinary illumination light and narrowband illumination light by controlling a filter insertion/removal mechanism 1016 of the light-source apparatus 1003.

Further, as will be explained below, the control circuit 1015 can also implement control for switching a characteristic of the video signal processing system inside the video processor 1004 in response to the switching control of the illumination light supplied to the light guide 1013 from the light-source apparatus 3.

The light-source apparatus 1003 is equipped with a lamp 1020, which emits illumination light, and the lamp 1020 emits illumination light that covers the wavelength region of visible light (red, green and blue). The illumination light, subsequent to being made approximately white illumination light by cutting the infrared light via an infrared cutting filter 1021, is irradiated onto a diaphragm 1022. The size of the opening of the diaphragm 1022 is controlled by a diaphragm drive circuit 1023. The amount of illumination light passing through the diaphragm 1022 is thereby controlled.

The illumination light passing through the diaphragm 1022 is irradiated onto a condenser lens 1025, either by passing through a narrowband filter 1024 removably inserted into the illumination light path by the filter insertion/removal mechanism 1016 configured by a plunger or the like, or by not passing through the narrowband filter 1024, is condensed by the condenser lens 1025, and is irradiated onto the end face of the hand side of the light guide 1013, that is, onto the incident end face.

FIG. 30 shows one example of the spectral characteristics of the narrowband filter 1024. The narrowband filter 1024 exhibits trimodal filter characteristics, and, for example, comprises a narrowband transmittance filter characteristic portion Ra, Ga, Ba for each of the wavelength regions of red, green and blue.

More specifically, the narrowband transmittance filter characteristic portions Ra, Ga, Ba have bandpass characteristics in which the respective center wavelengths are 600 nm, 540 nm and 420 nm, and the full widths at half maximum are between 20 and 40 nm.

Therefore, when the narrowband filter 1024 is positioned in the illumination light path, a three-band narrowband illumination light that transmits the narrowband transmittance filter characteristic portions Ra, Ga, Ba is irradiated onto the light guide 1013.

By contrast, when the narrowband filter 1024 is not positioned in the illumination light path, white light is supplied to the light guide 1013.

Illumination light from the light guide 1013 is transmitted by the light guide 1013 to the distal end face thereof, passes through an illumination lens 1027 mounted to an illumination window provided on the distal end portion 1026 of the insertion unit 1007, and is outputted to the outside, illuminating the surface of the living tissue of a diseased part or the like of a body cavity.

An observation window is provided adjacent to the illumination window in the distal end portion 1026, and an objective lens 1028 is mounted to the observation window. The objective lens 1028 forms an optical image via the light reflected from the living tissue. A charge-coupled device (abbreviated CCD) 1029 is positioned at the image-forming location of the objective lens 1028 as a solid-state image-capturing device, and the image is subjected to photoelectric transfer by the CCD 1029.

For example, the complementary color filter shown in FIG. 29 is mounted in pixel units to the image-capturing surface of the CCD 1029 as a color separation filter 1030 for separating colors optically.

The four color chips of the complementary color filter, magenta (Mg), green (G), cyan (Cy) and yellow (Ye), are positioned in front of each pixel, with Mg and G being alternately arranged in the horizontal direction, and the arrays Mg, Cy, Mg, Ye and G, Ye, G, Cy being arranged in that order in the vertical direction.

Then, the CCD 1029, which uses of the complementary color filter, is constituted so as to add and sequentially read out the two rows of pixels adjacent to one another in the vertical direction, reading out the rows of pixels by staggering the even and odd fields. As is known, luminance and color difference signals are then generated by the color separation circuit in the subsequent stage.

The above-mentioned CCD 1029 is connected to one end of a signal line, and connecting a signal connector, which is connected to the other end of the signal line, to the video processor 1004 connects a CCD drive circuit 1031 and CDS circuit 1032 inside the video processor 1004.

The CCD 1029 inputs an image-capturing signal, which has undergone photoelectric transfer, to the CDS circuit 1032 in accordance with the application of a CCD drive signal from the CCD drive circuit 1031. After a signal component has been extracted from the image-capturing signal, and converted to a baseband signal by the CDS circuit 1032, the baseband signal is inputted to a Y/C separation/synchronization circuit 1033, which performs Y/C separation and synchronization, and, in addition, is inputted to a selector 1035, which constitutes a modulated-light signal generation circuit 1034 for generating a modulated-light signal, and to a light modulation circuit 1037 by way of an integration circuit 1036.

The Y/C separation/synchronization circuit 1033, subsequent to generating a luminance signal Y and a line-sequential color difference signal, passes these signals through a low-pass filter not shown in the figure to create a luminance signal Y and line-sequential color difference signal of a prescribed band. In addition, the Y/C separation/synchronization circuit 1033 utilizes a delay line or the like not shown in the figure to make the line-sequential color difference signal into synchronized color difference signals Cr (=2R−G) and Cb (=2B−G), and outputs these signals to a first matrix circuit 1038 together with the luminance signal Y.

Furthermore, when the observation mode is switched from the ordinary-light observation mode to the narrowband-light observation mode by operating the mode-switching switch 1014, the control circuit 1015 changes the pass band of the low-pass filter through which the color difference signals Cr and Cb passed in the Y/C separation/synchronization circuit 1033 to broadband, thereby increasing the resolving power (resolution) thereof.

The first matrix circuit 1038 converts the inputted luminance signal Y and color difference signals Cr, Cb to color signals R, G and B, and outputs the converted color signals R, G, B to a second matrix circuit 1039.

The first matrix circuit 1038 converts the inputted luminance signal Y and color difference signals Cr, Cb to color signals R, G, B, which are not mixed colors.

Further, the second matrix circuit 1039 converts the color signals R, G, B to a luminance signal Y and color difference signals R-Y and B-Y.

In this case, the second matrix circuit 1039 uses a known method to convert the color signals R, G, B to a luminance signal Y and color difference signals R-Y and B-Y when in the ordinary-light observation mode, but when in the narrowband-light observation mode, the control circuit 1015 changes a matrix coefficient, and carries out a conversion that increases the ratio of G and B color signals, which are short wavelengths, and more particularly the ratio of the shortest wavelength B color signals, relative to the long-wavelength R color signal.

In other words, when in the narrowband-light observation mode, the control circuit 1015 operates such that a luminance signal Ynbi and color difference signals R-Y and B-Y, which are weighted toward the B signal in particular, are generated from color signals R, G, B.

The conversion equation in this case is as follows when using three-row, three-column matrices A and K.

$$\begin{pmatrix} Ynbi \\ R-Y \\ B-Y \end{pmatrix} = A \begin{pmatrix} 0 & k1 & 0 \\ 0 & 0 & k2 \\ 0 & 0 & k3 \end{pmatrix} \begin{pmatrix} R \\ G \\ B \end{pmatrix} \quad (2)$$

Here, matrix K, for example, comprises three real coefficients k1 through k3 (the other coefficient component is 0), and, a conversion equation like Equation (2) suppresses the long-wavelength R color signal, and, by contrast, increases the weight of the short-wavelength G and B color signals. Furthermore, when in the ordinary-light observation mode, conversion is carried out omitting the matrix K in Equation (2).

Further, A is a matrix for converting from RGB signals to Y color difference signals, and the following known operation coefficient (3) can be used.

$$A = \begin{pmatrix} 0.299 & 0.587 & 0.114 \\ -0.299 & -0.587 & 0.886 \\ 0.701 & -0.587 & -0.114 \end{pmatrix} \quad (3)$$

The luminance signal Y and color difference signals R-Y and B-Y outputted from the second matrix circuit 1039 are inputted to an enlargement circuit 1040, and are subjected to enlargement processing. Further, the luminance signal Y is inputted to the selector 1035.

The output signal of the enlargement circuit 1040 is inputted to a highlighting circuit 1041, and subjected to structural highlight processing. The output signal of this highlighting circuit 1041 is inputted to a third matrix circuit 1042. Furthermore, the luminance signal Y component alone can be highlighted by the highlighting circuit 1041.

The luminance signal Y and color difference signals R-Y and B-Y inputted to the third matrix circuit 1042 are converted to color signals R, G, B by the third matrix circuit 1042, and outputted to the monitor 1005 from an output terminal. Then, the endoscopic image captured by the CCD 1029 is displayed on the display screen of the monitor 1005.

The above-mentioned control circuit 1015 controls signal selection by the selector 1035 using a mode switching signal.

More specifically, when switching to the narrowband-light observation mode, the control circuit 1015 implements switching such that the luminance signal Y outputted from the second matrix circuit 1039 is inputted to the integration circuit 1036 and light modulation circuit 1037 by way of the selector 1035. Furthermore, the integration circuit 1036, which integrates an input signal and outputs an average value, can also be an equalization circuit for generating an average value.

Meanwhile, in the ordinary-light observation mode, the control circuit 1015 implements switching such that an output signal from the CDS circuit 1032 is inputted to the integration circuit 1036 and light modulation circuit 1037 by way of the selector 1035.

The configuration of the modulated-light signal generation circuit 1034 will be explained below in accordance with FIG. 31. In the present embodiment, the modulated-light signal generation circuit 1034 equalizes an output signal of the CDS circuit 1032 and generates a light modulation reference signal <Yn> in the ordinary-light observation mode, and equalizes a luminance signal outputted by way of the second matrix circuit 1039, and generates a light modulation reference signal <Ynbi> in the narrowband-light observation mode.

In the narrowband-light observation mode, the ratio of respective color signals in the light modulation reference signal <Ynbi> differs from the ratio of respective color signals in the light modulation reference signal <Yn> resulting from the second matrix circuit 1039 implementing a conversion and the like that increases the ratio of a short-wavelength color signal.

FIG. 31 shows an example of a configuration of the modulated-light signal generating circuit 1034.

As explained hereinabove, a signal selected by the selector 1035 is inputted to the integration circuit 1036, where it becomes a light modulation reference signal of either <Yn> or <Ynbi> (notated as <Yn>/<Ynbi> in this specification and drawings), which has undergone integration and equalization in a prescribed period, and is inputted to a subtraction circuit 1045, which constitutes a light modulation circuit 1037. Furthermore, the integration circuit 1036 is equipped with a S/H circuit, which performs sample/hold (S/H), and outputs to the subtraction circuit 1045 an integration value integrated in a prescribed period by an S/H control signal Ssh from the control circuit 1015.

The subtraction circuit 1045 outputs to the diaphragm drive circuit 1023 of the light-source apparatus 1003, as a modulated-light signal, a value arrived at by subtracting from the light modulation reference signal <Yn>/<Ynbi> a reference value (a light modulation target value) En/Enbi corresponding to the proper brightness generated by a reference value generation circuit (target value generation circuit) 1046.

Furthermore, En is the reference value in the ordinary-light observation mode, and Enbi is the reference value in the narrowband-light observation mode. Respectively setting such target values, which constitute light modulation references, in the ordinary-light observation mode and in the narrowband-light observation mode makes it possible to modulate light to an appropriate target value in both modes.

In this case, the control circuit 1015, operating in response to a mode-switching signal, uses a switching control signal Sc to switch between the selector 1035 and the reference value En/Enbi. Further, the control circuit 1015 applies to the integration circuit 1036 a control signal Ssh, which performs sample/hold, and outputs to the subtraction circuit 1045 a light modulation reference signal <Yn>/<Ynbi> that has been integrated in a prescribed period.

The modulated-light signal outputted from the light modulation circuit 1037 is outputted to the diaphragm drive circuit 1023.

The diaphragm drive circuit 1023 reduces the size of the opening of the diaphragm 1022 when the modulated-light signal is a positive value, for example, and, conversely, increases the size of the opening of the diaphragm 1022 when the modulated-light signal is a negative value, and adjusts the quantity of illumination light, automatically modulating the light such that the light modulation reference signal <Yn>/<Ynbi> constitutes a reference value En/Enbi of proper brightness.

The automatic light modulation makes it possible for an endoscopic image captured by the CCD 1029 and displayed on the monitor 1005 to constantly maintain the proper brightness.

Furthermore, three primary color signals R, G, B actually inputted to the respective R, G, B channels of the monitor 1005 from the video signal output terminal constitute the signals G, B, B (weighting differs according to the coefficients) when Equation (1) is employed in the narrowband-light observation mode, the ratio of B signals in particular increases, and thanks to the B signals, it becomes possible to display, under easy-to-identify circumstances, an endoscopic image corresponding to a structure, such as the capillary vessels in the vicinity of a superficial portion of a living tissue.

That is, the signals respectively inputted to the R, G, B channels of the monitor 1005 in the narrowband-light observation mode are actually G, B, and B signals, thereby enhancing visibility.

Operation according to the present embodiment will be explained below by referring to FIG. 32.

An operator connects an endoscope 1002 to a light-source apparatus 1003 and video processor 1004 as shown in FIG. 28, turns on the power, and the control circuit 1015 of the video processor 1004 starts initialization processing, and as shown in Step S1, for example, sets the ordinary-light observation mode as the operation mode of the light-source apparatus 1003 and video processor 1004.

In this state, the light-source apparatus 1003 is set such that the narrowband filter 1024 is separated from the illumination light path as shown in FIG. 28, and image capturing is performed by the endoscope 1002 under white illumination light. Further, the respective parts of the video processor 1004 are also set to perform signal processing in the ordinary-light observation mode state.

In this case, the control circuit 1015 controls the signal switching of the selector 1035 such that an output signal from the CDS circuit 1032 is inputted to the integration circuit 1036. Then, the control circuit 1015 implements control so as to generate a light modulation reference signal <Yn> in accordance with an output signal of the CDS circuit 1032, and, in addition, to send a modulated-light signal, from which a brightness reference value En has been subtracted by the light modulation circuit 1037, to the diaphragm drive circuit 1023 of the light-source apparatus 1003, such that the diaphragm 1022 constitutes the appropriate quantity of illumination light.

An operator inserts the insertion unit 1007 of the endoscope 1002 into a body cavity of a patient, making it possible to conduct an endoscopic examination in a state of illumination under which an image of appropriate brightness can be obtained. When he wants to observe in more detail the location or course of the surface blood vessels of a tissue targeted for examination, such as a diseased part of the body cavity, the operator operates the mode-switching switch 1014.

As shown in step S2, the control circuit 1015 monitors whether or not the mode-switching switch 1014 has been operated, and when the mode-switching switch 1014 has not been operated, it maintains this status, and when the mode-switching switch 1014 has been operated, it proceeds to the next step S3.

In step S3, the control circuit 1015 changes the operation mode of the light-source apparatus 1003 and video processor 1004 to the setting state of the narrowband-light observation mode.

More specifically, the control circuit 1015 performs control relative to the light-source apparatus 1003 such that the narrowband filter 1024 is positioned in the illumination light path as indicated by the two-dot chain line in FIG. 28. As indicated by the transmittance characteristics shown in FIG. 30, positioning the narrowband filter 1024 in the path of the illumination light results in illumination by a narrowband illumination light in accordance with the narrowband transmission filter characteristic sections Ra, Ga, Ba.

Further, the control circuit 1015 changes the settings of the respective parts of the video processor 1004. More specifically, the control circuit 1015 implements changes so as to increase a matrix coefficient of the second matrix circuit 1039, and more particularly the ratio of signal components resulting from the color signal B (in accordance with the narrowband transmission filter characteristic section Ba) in the luminance signal Ynbi.

Further, the control circuit 1015 switches the selector 1035, and a luminance signal Ynbi from the second matrix circuit 1039 is inputted to the integration circuit 1036 by way of the selector 1035, becoming the light modulation reference signal <Ynbi>, and, in addition, the light modulation circuit 1037 subtracts the brightness reference value Enbi and generates a modulated-light signal. This modulated-light signal adjusts the quantity of illumination light. Then, an appropriate quantity of illumination light for facilitating a diagnosis is set in the narrowband-light observation mode.

Further, since changing the settings of the above-mentioned signal processing system implements changes that increase, for example, a matrix coefficient of the second matrix circuit 1039 in the narrowband light observation mode, and more particularly the ratio of signal components of the color signal B, it is possible to observe in an easy-to-identify state the course of a capillary vessel in the vicinity of a superficial portion of a living tissue, the image of which was captured under B illumination light via the narrowband transmission filter characteristic section Ba.

Further, since narrowband properties are converted to broadband when color difference signals Cr, Cb are generated in the Y/C separation/synchronization circuit 1033, it is possible to enhance the resolution of the course of a capillary vessel, as well as the course of a blood vessel located deeper than the superficial portion, the image of which was captured under G illumination light via the narrowband transmission filter characteristic section Ga.

In the next step S4, the control circuit 1015 monitors whether or not the mode-switching switch 1014 has been operated, and when the mode-switching switch 1014 has not been operated, maintains the status, and when the mode-switching switch 1014 has been operated, returns to the next step S1.

According to an embodiment like this, a modulated-light signal suited to light modulation is generated from respective luminance signals in the ordinary-light observation mode and the narrowband-light observation mode, thereby producing an endoscopic image of a brightness well suited to each mode of observation.

Further, according to the present embodiment, it is possible to adequately secure the observation function of the narrowband-light observation mode by holding a color image-capturing function resulting from an ordinary synchronous system, and by changing a coefficient and other settings of the respective parts of the video processor 1004 in the narrowband-light observation mode as well.

Next, a concrete example for appropriately setting, in both the ordinary-light observation mode and narrowband-light observation mode, the ratio of the contribution of the respective color signals that generate a light modulation reference signal, will be explained.

FIG. 33 shows a configuration of the peripheral parts of modulated-light signal generation circuit 1034B in a variation of the present embodiment. In the modulated-light signal generation circuit 1034B, color signals R, G, B of the first matrix circuit 1038 are inputted into respective multipliers 1047a, 1047b, and 1047c, and after being respectively multiplied by coefficients outputted from a ROM 1048, which stores multiplier coefficients, are added by an addition circuit 1049.

The ROM 1048 stores coefficients for the ordinary-light observation mode, and coefficients for the narrowband-light observation mode, and the control circuit 1015, operating in response to a mode-switching signal, reads out the corresponding coefficients, and outputs to the multipliers 1047a, 1047b, 1047c.

More specifically, in the ordinary-light observation mode, coefficients of a ratio of 5:9:3 (when equalized, this ratio becomes 5/17:9/17:3/17) are inputted to the multipliers 1047a, 1047b, 1047c from the ROM 1048, and subsequent to being respectively multiplied with R, G, B color signals, these coefficients are added by the addition circuit 1049.

Therefore, the light modulation reference signal Yn, prior to being outputted from the addition circuit 1049 and equalized in the ordinary-light observation mode, constitutes Yn=5R/17+9G/17+3B/17.

Further, in the narrowband-light observation mode, coefficients of a ratio of 0:5:12 (when equalized, this ratio becomes 0/17:5/17:12/17) are inputted to the multipliers 1047a, 1047b, 1047c from the ROM 1048, and subsequent to being respectively multiplied with R, G, B color signals, these coefficients are added by the addition circuit 1049.

Therefore, the light modulation reference signal Ynbi, prior to being outputted from the addition circuit 49 and equalized in the narrowband-light observation mode, constitutes Ynbi=0×R/17+5G/17+12B/17. Thus, the output signal Yn or Ynbi (that is, Yn/Ynbi) of the addition circuit 1049 is inputted to the integration circuit 1036, is integrated, respectively become a light modulation reference signal <Yn>/<Ynbi>, and is inputted to the light modulation circuit 1037.

The rest of the configuration is the same as that of the second embodiment.

According to this variation, since the configuration is such that the ratio of color signals is appropriately set, and a light modulation reference signal is generated in both the ordinary-light observation mode and the narrowband-light observation mode just like in the second embodiment, it is possible to achieve an image of a brightness that facilitates a diagnosis in each mode.

Furthermore, as described hereinabove, since signal processing, which suppresses the R color signal via the narrowband transmission filter section Ra in the narrowband-light observation mode is performed, a narrowband filter that does not have the transmittance characteristics of the narrowband transmission filter section Ra can be used as the narrowband filter 1024 shown in FIG. 30. In this case, the narrowband filter constitutes a two-peak filter having the narrowband transmission filter sections Ga and Ba, and can contribute toward lowering costs.

Third Embodiment

Next, a third embodiment of the present invention will be explained by referring to FIGS. 36 through 39. Since the third embodiment is practically the same as the second embodiment, only the points of difference will be explained, and an explanation of identical components having the same reference numerals will be omitted.

Figure 36:
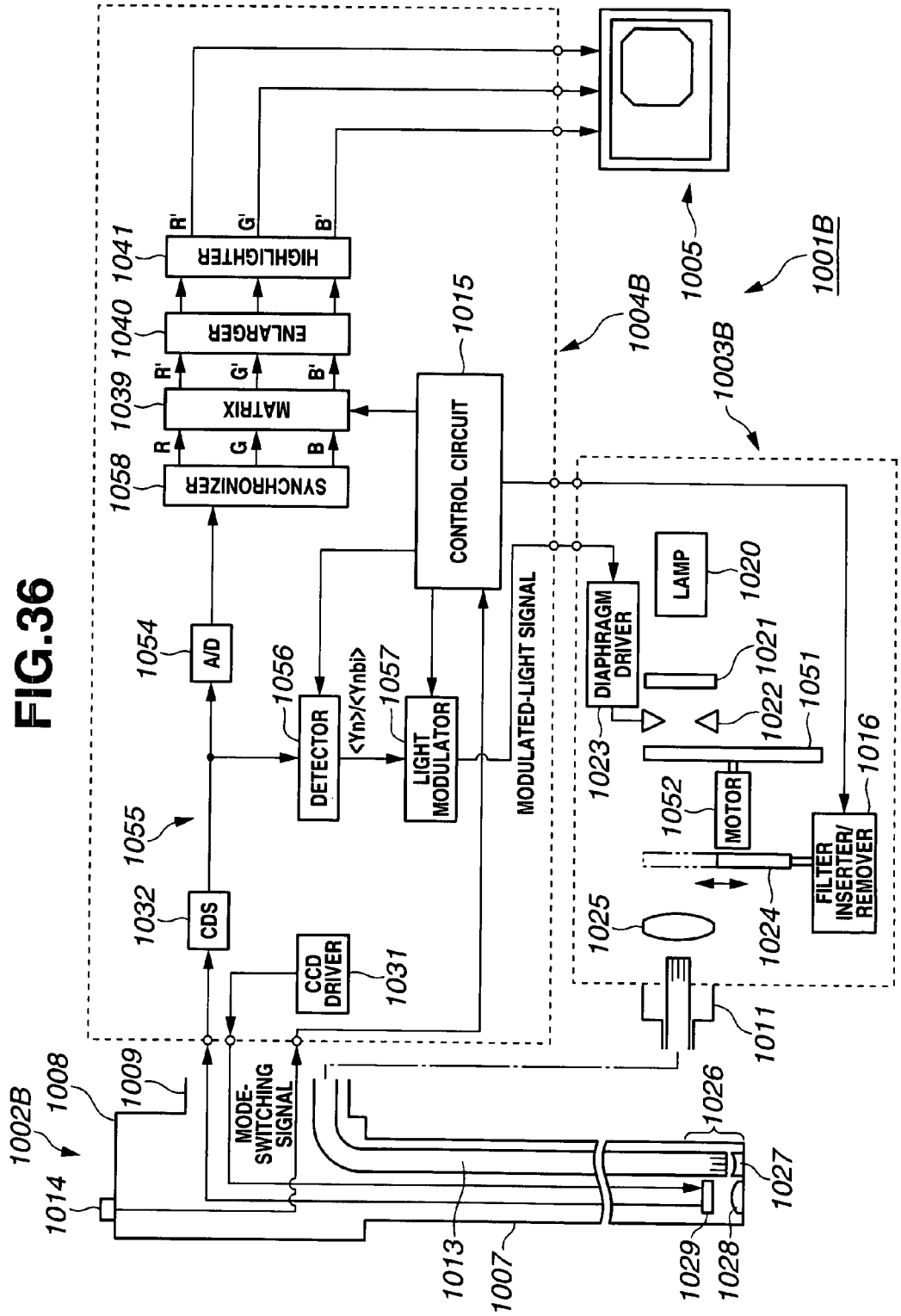
FIG. 36 is a block diagram showing a configuration of an endoscope apparatus according to a third embodiment of the present invention.

FIG. 36 shows a configuration of an endoscope apparatus 101B according to a third embodiment of the present invention. The second embodiment is a synchronous-type endoscope apparatus 1001, which captures a color image using a synchronous-type endoscope 1002 including a color filter (optical filter for color separation), but the present embodiment is a surface-sequential-type endoscope apparatus 1001B, which surface-sequentially captures a color image using a surface-sequential-type endoscope 1002B that does not have a color filter.

As shown in FIG. 36, the endoscope apparatus 1001B comprises an endoscope 1002B; a light-source apparatus 1003B for supplying illumination light to the endoscope 1002B; a video processor 1004B, which drives image-capturing means built into the endoscope 1002B, and performs signal processing for image-capturing means output signals; and a monitor 1005, which displays an endoscopic image captured by image-capturing means in accordance with the inputting of a video signal outputted from the video processor 1004B.

The endoscope 1002B employs a CCD 1029 that does not have a color separation filter 1030, in other words, a monochrome CCD, instead of the color separation filter 1030-equipped CCD 1029 in the endoscope 1002 of FIG. 28.

Further, the light-source apparatus 1003B has a rotating filter 1051 arranged in the optical path between, for example, the diaphragm 1022 and filter 1024 in the endoscope 1003 of FIG. 28, and the rotating filter 1051 is rotated at a constant speed by a motor 1052.

R, G and B filters 1053R, 1053G, 1053B which respectively transmit light of the respective bands of R, G, B, are circumferentially mounted to the rotating filter 1051 as shown in FIG. 37(A). The transmittance characteristics of these R, G, B filters 1053R, 1053G, 1053B comprise transmission sections Rb, Gb, Bb, which transmit the respective R, G, B wavelength regions in broadband as shown in FIG. 37(B).

Then, in the ordinary-light observation mode, the broadband R, G, B illumination light, which permeates the R, G, B filters 1053R, 1053G, 1053B of the rotating filter 1051, is surface-sequentially supplied to the light guide 1013.

Meanwhile, in the narrowband-light observation mode, the narrowband filter 1024 is arranged in the optical path, and the broadband R, G, B illumination light, which permeates the R, G, B filters 1053R, 1053G, 1053B of the rotating filter 1051, is made into narrowband R, G, B illumination light by the narrowband filter 1024, and surface-sequentially supplied to the light guide 1013.

Further, in the video processor 1004B of the present embodiment, the CCD 1029 is driven by the CCD drive circuit 1031, and an image-capturing signal captured by the CCD 1029 is inputted to the CDS circuit 1032, and subjected to CDS processing.

The output signal of the CDS circuit 1032 is inputted to an A/D conversion circuit 1054, and converted to a digital signal, and, in addition, is inputted to a light modulation circuit 1057 by way of a detection circuit 1056, which constitutes a modulated-light signal generation circuit 1055.

A digital signal generated by the A/D conversion circuit 1054 is inputted to a synchronization circuit 1058, and after surface-sequentially captured R, G, B color component images are temporarily stored in a memory constituting the synchronization circuit 1058, R, G, B signals, which have been simultaneously read out and synchronized, are outputted to a matrix circuit 1059.

A matrix coefficient of the matrix circuit 1059 is changed in the ordinary-light observation mode and in narrowband-light observation mode by the control circuit 1015. More specifically, in the ordinary-light observation mode, it is a matrix of units, but in the narrowband-light observation mode, the matrix coefficient is changed so as to possess a function similar to that of the second matrix circuit 1039 of the second embodiment.

An output signal of the matrix circuit 1059 is outputted to the monitor 1005 from an output terminal after respectively undergoing enlargement and highlight processing by the enlargement circuit 1040 and highlighting circuit 1041 the same as in the second embodiment.

Figure 38:
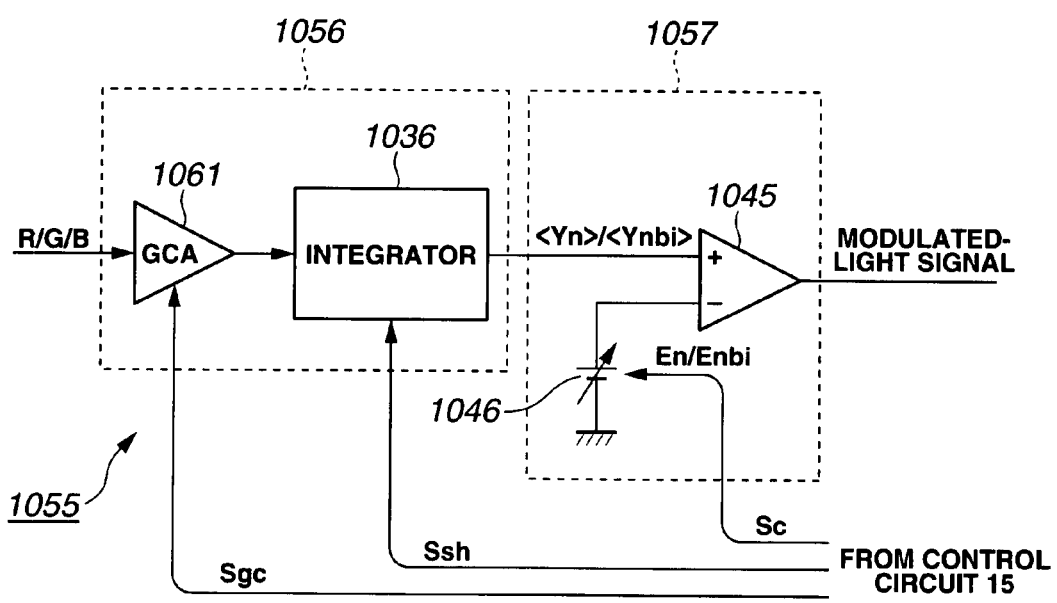
FIG. 38 is a circuit diagram showing a configuration of the modulated-light signal generation circuit.

FIG. 38 shows an example of the circuitry of the modulated-light signal generation circuit 1055. Surface-sequential R, G, B signals are inputted, for example, to a gain control amplifier (abbreviated GCA) 1061, which constitutes the detection circuit 1056, and a gain control signal Sgc from the control circuit 1015 is applied to a gain control terminal of the GCA 1061. The GCA 1061 has the gain (amplification factor) at output by amplifying an input signal variably controlled in accordance with the signal level of the gain control signal Sgc.

The gain control signal Sgc changes each signal period of a surface-sequential input signal, and in the ordinary-light observation mode, for example, the gain of the GCA 1061 is set, for example, at the ratio 5:9:3 relative to R, G, B input signals. The ratio setting when equalized (standardized) becomes 5/17:9/17:3/17.

Meanwhile, in the narrowband-light observation mode, for example, the gain of the GCA 1061 is set, for example, at the ratio 0:5:12 relative to the R, G, B input signals. The ratio setting when equalized becomes 0/17:5/17:12/17.

Further, an output signal of the above-mentioned GCA 1061 is inputted to the integration circuit 1036, where it is integrated, and a light modulation reference signal <Yn>/<Ynbi> is generated.

In the ordinary-light observation mode, the light modulation reference signal <Yn> becomes <Yn>=5<R>/17+9<G>/17+3<B>/17.

Further, in the narrowband-light observation mode, the light modulation reference signal <Ynbi> becomes <Ynbi>=0 x<R>/17+5<G>/17+12<B>/17.

The light modulation reference signal <Yn>/<Ynbi> outputted from the integration circuit 1036 is inputted to the subtraction circuit 1045, which constitutes a light modulation circuit 1057, and a signal, from which reference values En/Enbi of the reference value generation circuit 1046 have been subtracted, is outputted to the diaphragm drive circuit 1023 as a modulated-light signal.

Further, a reference value E is also variably set corresponding to the ordinary-light observation mode and the narrowband-light observation mode by a switching control signal Sc from the control circuit 1015.

Furthermore, the detection circuit 1056 may be constituted from a multiplier and a coefficient unit.

According to the present embodiment, which has a configuration and operations like this, it is possible to automatically adjust the quantity of illumination light appropriately in both the ordinary-light observation mode and in the narrowband-light observation mode the same as in the variation of the second embodiment.

Figure 39:
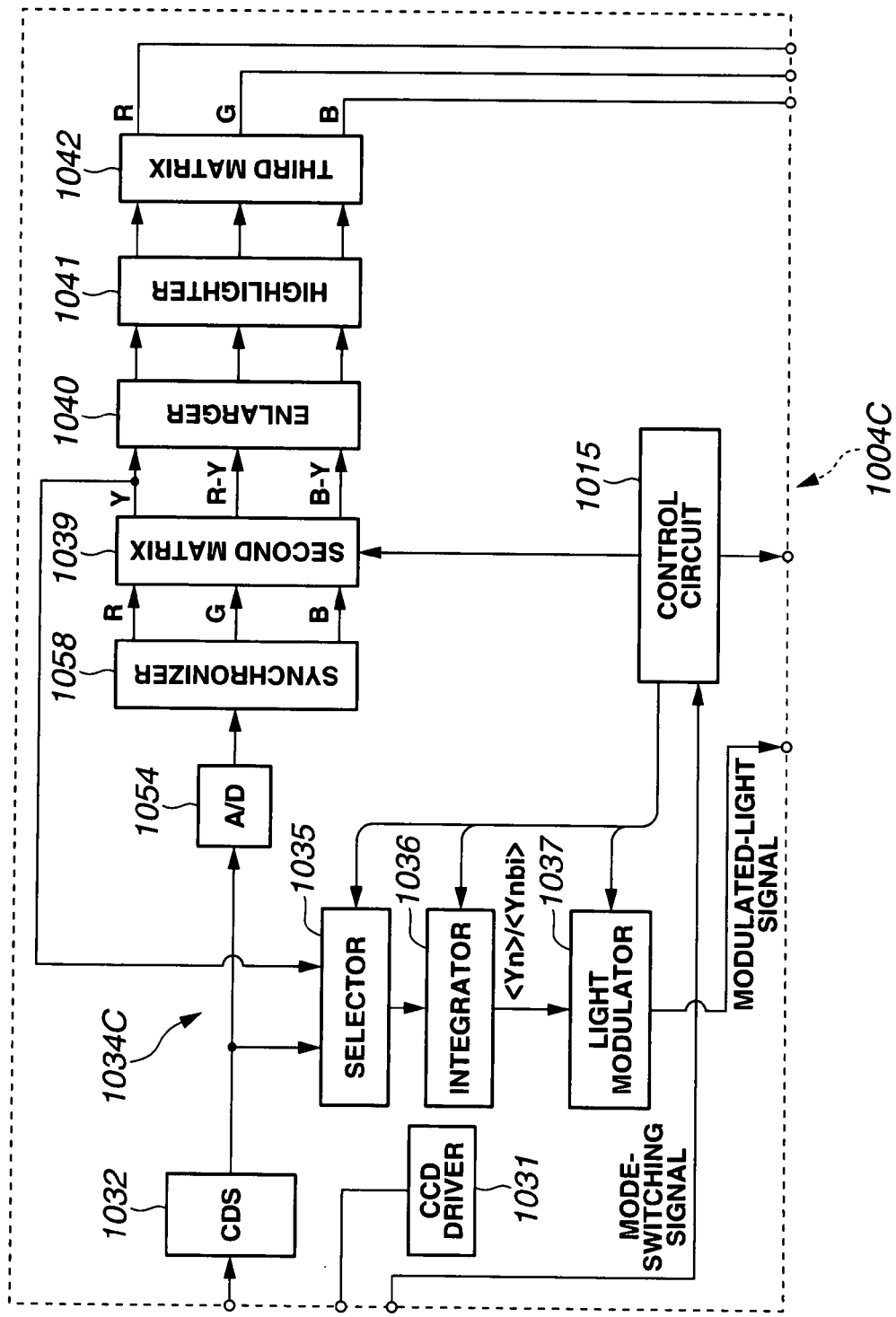
FIG. 39 is a block diagram showing a configuration of the video processor of a variation of the third embodiment.

FIG. 39 shows a configuration of a video processor 1004C of a variation of the third embodiment. The video processor 1004C applies the modulated-light signal generation circuit 1034 in the second embodiment, which is a synchronous-type, and comprises a surface-sequential-type modulated-light signal generation circuit 1034C, which is similar to the modulated-light signal generation circuit 1034.

Thus, the video processor 1004C employs the second matrix circuit 1039 of the second embodiment instead of the matrix circuit 1059 in the video processor 1004B of FIG. 36. The second matrix circuit 1039 converts R, G, B signals outputted from a synchronization circuit 1058 to a luminance signal Y and color difference signals R-Y, B-Y.

In this case, the matrix coefficients of the second matrix circuit 1039 are linked to mode switching and are switched by the control circuit 1015 as in the second embodiment.

That is, in the ordinary-light observation mode, the second matrix circuit 1039 converts an RGB signal to a luminance signal Y and color difference signals R-Y, B-Y, but in the narrowband-light observation mode, conversion is performed as in Equation (2) explained in the second embodiment.

Then, the luminance signal Ynbi in the narrowband-light observation mode is integrated by the integration circuit 1036 by way of the selector 1035, which constitutes the modulated-light signal generation circuit 1034C, to become light modulation reference signal <Ynbi>, which is inputted to the light modulation circuit 1037 and becomes a modulated-light signal.

Further, in the ordinary-light observation mode, an output signal of the CDS circuit 1032 is integrated by the integration circuit 1036 by way of the selector 1035, which constitutes the modulated-light signal generation circuit 1034C, to become light modulation reference signal <Yn>, which is inputted to the light modulation circuit 1037 and becomes a modulated-light signal.

Furthermore, an output signal of the highlighting circuit 1041 is inputted to the third matrix circuit 1042, and subsequent to being converted to a color signal RGB, is outputted to the monitor 1005 from an output terminal.

According to a variation of the third embodiment constituted like this, it is a surface-sequential system, but the same operational effect as that of the second embodiment can be obtained.

Furthermore, for example, a two-peak filter, which comprises the narrowband transmission filter characteristic sections Ga, Ba, but does not comprise the transmittance characteristics of the narrowband transmission filter characteristic section Ra as explained in the second embodiment, can also be used in the third embodiment as the narrowband filter 1024.

Fourth Embodiment

Figure 40:
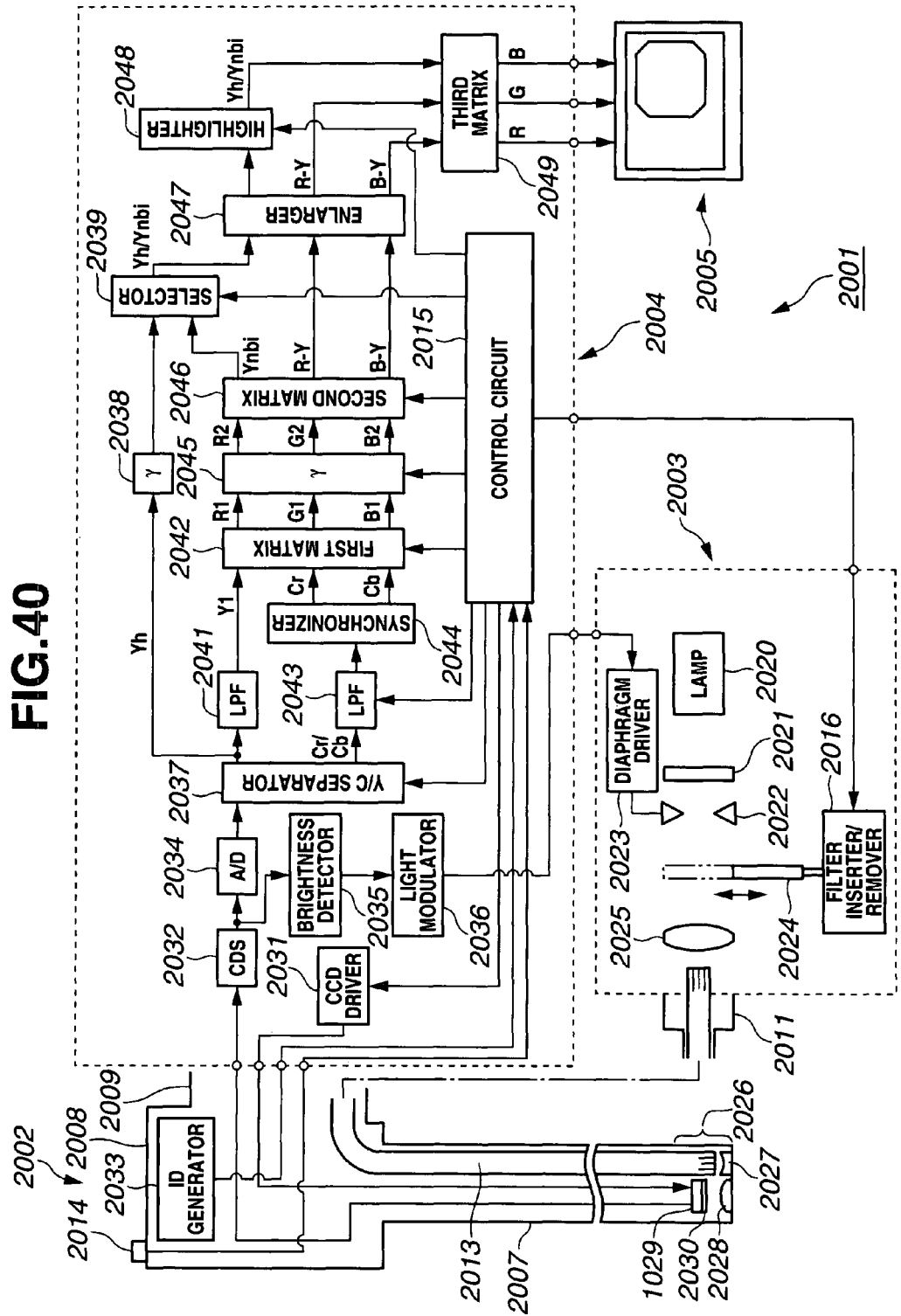
FIG. 40 is a block diagram showing a configuration of an endoscope apparatus according to a fourth embodiment of the present invention.
Figure 41:
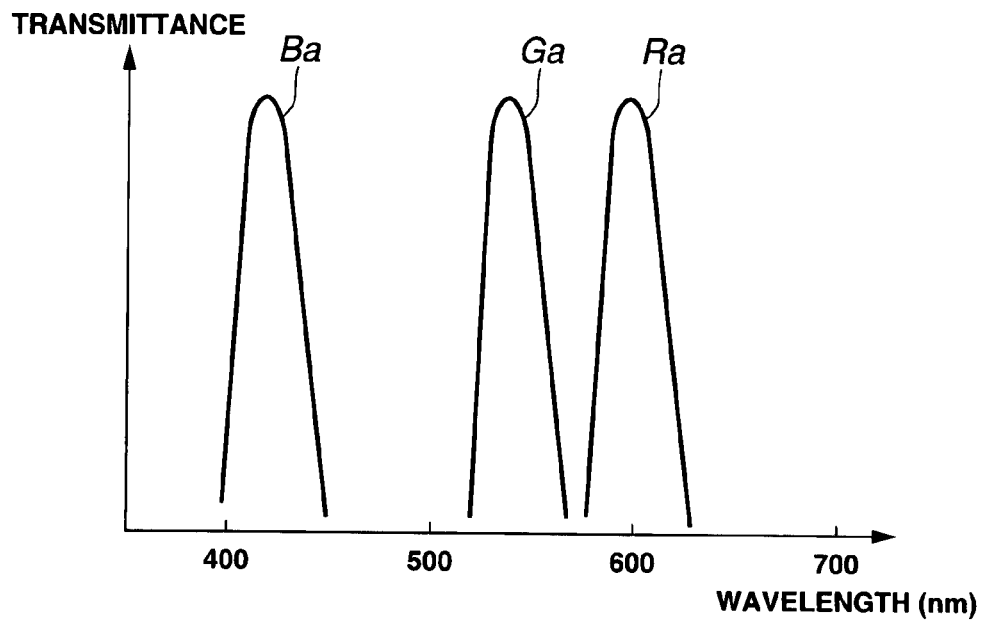
FIG. 41 is a diagram showing a configuration of a filter array of color separating filters provided in a solid-state image-capturing device.
Figure 42:
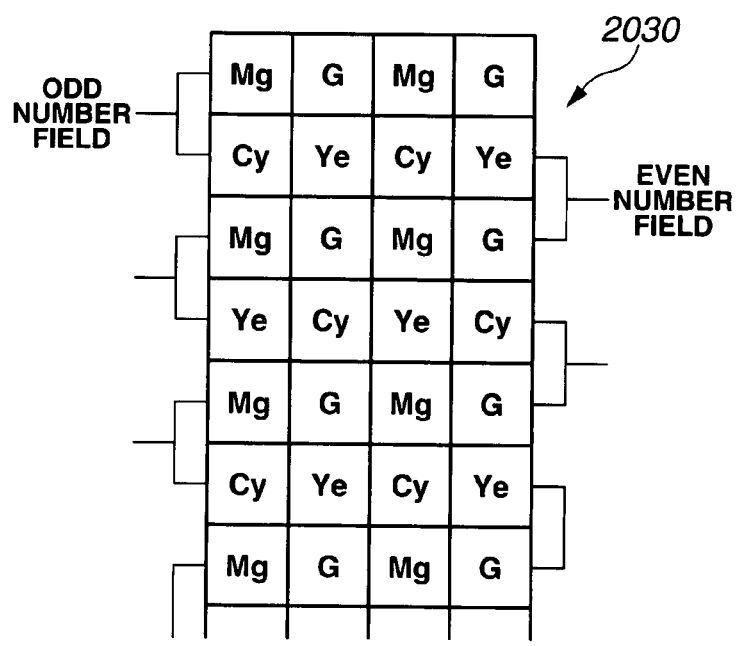
FIG. 42 is a characteristics diagram showing an example of the spectral characteristics of a narrowband filter.
Figure 43:
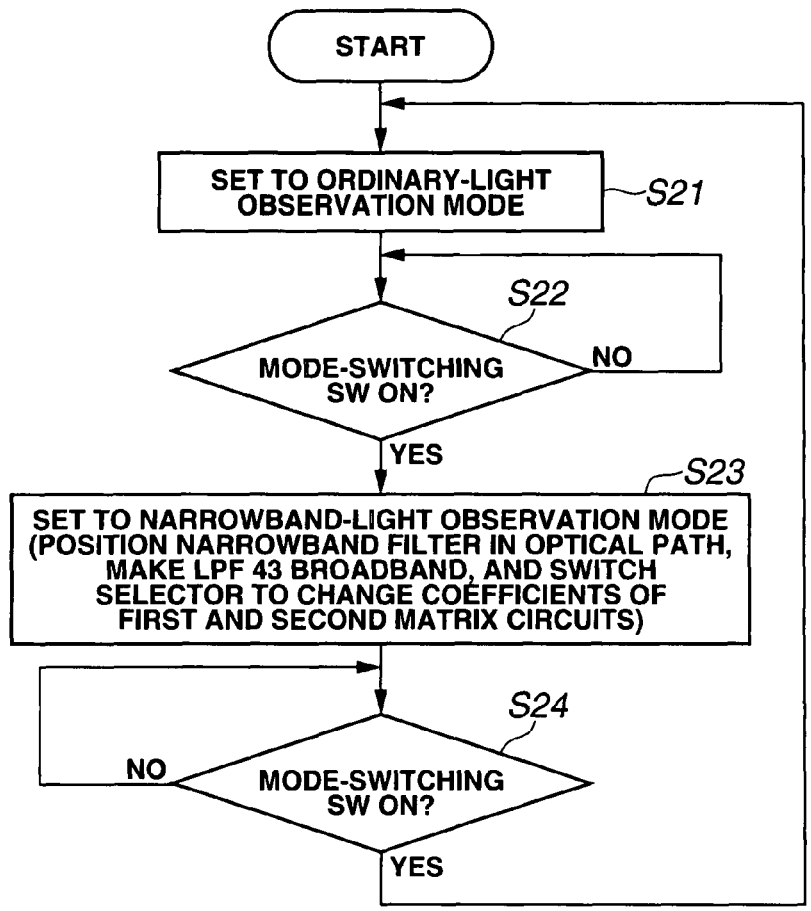
FIG. 43 is a flowchart for explaining the operation of the fourth embodiment.
Figure 44:
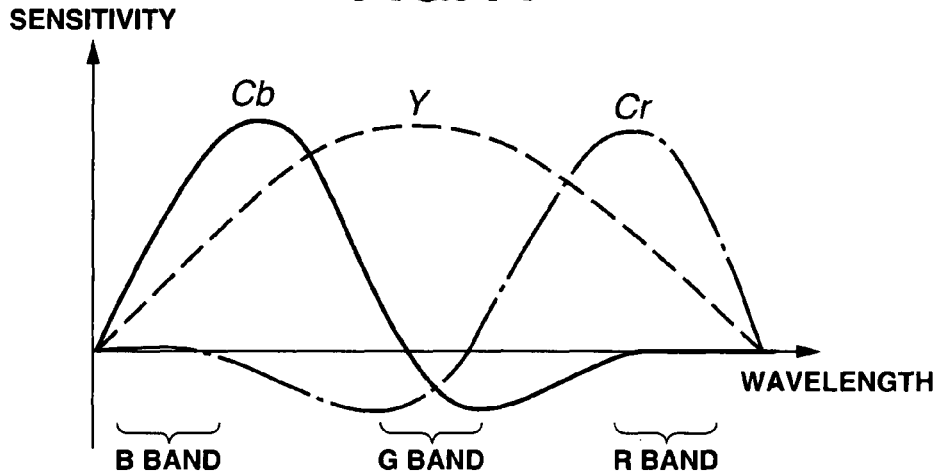
FIG. 44 is a diagram showing the signal bands for a luminance signal and color difference signals.
Figures 45, 46:
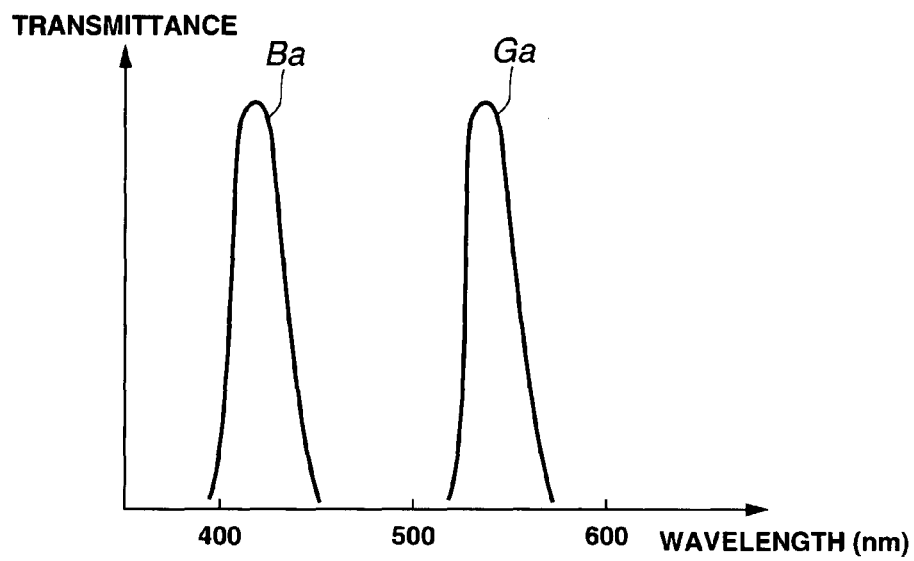
FIG. 45 is a diagram showing coefficients of a second matrix circuit set in a first variation of the fourth embodiment that takes into account the characteristics of FIG. 44.
FIG. 46 is a characteristic diagram showing the spectral characteristics of a narrowband filter in a second variation of the fourth embodiment.
Figure 48:
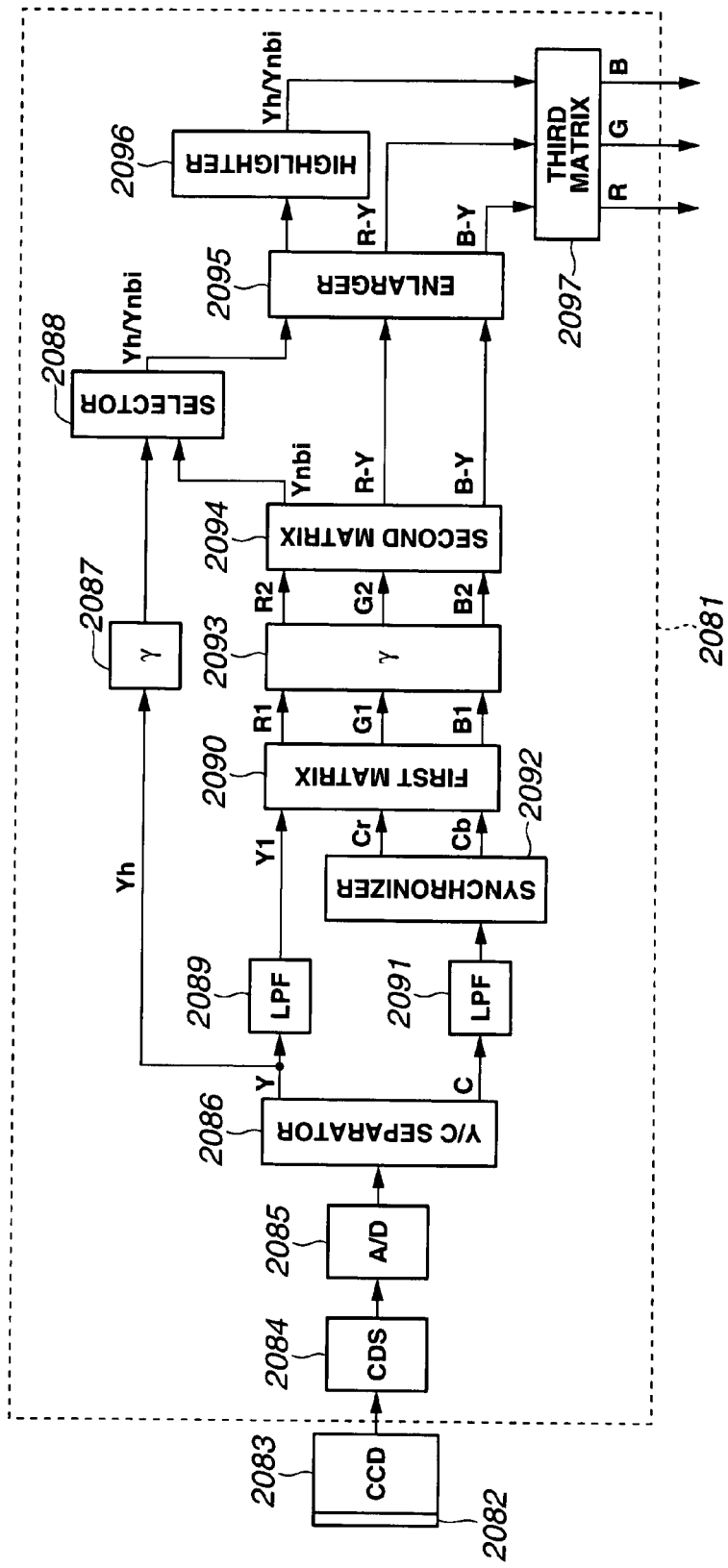
FIG. 48 is a block diagram showing a configuration of a video signal processing apparatus of a conventional example.

FIGS. 40 through 48 are related to a fourth embodiment of the present invention. FIG. 40 shows a configuration of an endoscope apparatus according to a fourth embodiment of the present invention; FIG. 41 shows a configuration of a filter array of color separating filters provided in a solid-state image-capturing device; FIG. 42 shows an example of the spectral characteristics of a narrowband filter; FIG. 43 shows a flowchart used for explaining the operation of the present embodiment; FIG. 44 shows the signal bands in a luminance signal and color difference signals; FIG. 45 shows the coefficients of a second matrix circuit set in a first variation that takes into account the characteristics of FIG. 44; FIG. 46 shows the spectral characteristics of a narrowband filter in a second variation; FIG. 47 shows the coefficient of the second matrix circuit set in the second variation of FIG. 46; and FIG. 48 shows a block diagram depicting a configuration of a video signal processing apparatus of the prior art.

In recent years, electronic endoscopes including image-capturing means have come to be widely employed in various types of endoscopic examinations.

When performing an endoscopic examination using an electronic endoscope, there is a synchronous-type endoscope apparatus, which captures a color image under white light by using an image-capturing device including a color optical filter, and there is a surface-sequential-type endoscope apparatus, which generates a color image by using a monochrome image-capturing device, and respectively capturing an image under R, G and B surface-sequential illumination lights. The signal processing system differs in the two types of apparatuses.

Further, for example, Japan Patent Laid-open No. 2002-95635 discloses a endoscope apparatus, which uses narrowband illumination light, and which can display, as readily identifiable image data, the state of a blood vessel's course in the depth direction in the vicinity of a superficial portion of a mucous membrane. Such data can be easily buried in optical data obtained with ordinary visible light.

In the prior art of the above-mentioned official gazette, a narrowband image is surface-sequentially generated using a narrowband illumination light, making it possible to obtain a narrowband image relatively easily without having to make a big change in the signal processing system, if the illumination light is changed to narrowband illumination light instead of R, G, B surface-sequential illumination light.

Meanwhile, FIG. 48 shows a configuration of a video signal processing apparatus 2081 for a synchronous-type electronic endoscope of the prior art.

A color image-capturing signal captured by a charge-coupled device (abbreviated CCD) 2083, which comprises a color separation filter 2082, is inputted to a CDS circuit 2084 inside the video signal processing apparatus 2081, where it is subjected to CDS processing, and a baseband signal component is extracted.

An output signal of the CDS circuit 2084 is inputted to an A/D conversion circuit 2085, where it is converted from an analog signal to a digital signal. The digital signal is inputted to a Y/C separation circuit 2086, and is separated into a luminance signal Y and a line-sequential color signal (color difference signal) C in the Y/C separation circuit 2086.

The luminance signal Y is inputted to a selector 2088 by way of a γ circuit 2087 (this luminance signal becomes Yh), and, in addition, is inputted to a first low-pass filter (abbreviated LPF) 2089. The LPF 2089 is set to broadband, and the luminance signal Y1 of the band set by the LPF 2089 is inputted to a first matrix circuit 2090.

Further, the color signal C is inputted to a (line-sequential) synchronization circuit 2092 by way of a second LPF 2091. In this case, the second LPF 2091 is a lower band than the first LPF 2089.

The synchronization circuit 2092 generates synchronized color difference signals Cr (=2R−G) and Cb (=2B−G), and inputs the color difference signals Cr, Cb to the first matrix circuit 2090.

The first matrix circuit 2090 converts the luminance signal Y1 and color difference signals Cr, Cb to three primary color signals R1, G1, B1, and outputs them to a γ circuit 2093. The three primary color signals R2, G2, B2, which have been subjected to γ-correction by the γ circuit 2093, are inputted to a second matrix circuit 2094, and are converted to a luminance signal Ynbi and color difference signals R-Y, B-Y by the second matrix circuit 2094.

In this case, the second matrix circuit 2094 converts the three primary color signals R2, G2, B2 to the luminance signal Ynbi and color difference signals R-Y and B-Y so that the color constitutes a natural tone.

The luminance signal Ynbi outputted by the second matrix circuit 2094 is inputted to an enlargement circuit 2095 by way of the selector 2088, and the color difference signals R-Y, B-Y are inputted to the enlargement circuit 2095. The selector 2088 selects the γ-corrected luminance signal Yh from the Y/C separation circuit 2086, and the luminance signal Ynbi inputted by way of the second matrix circuit 2094, and outputs them to the enlargement circuit 2095.

The luminance signal Yh/Ynbi, which was subjected to enlargement processing by the enlargement circuit 2095, is inputted to a third matrix circuit 2097 by way of a highlighting circuit 2096, and the color difference signals R-Y, B-Y, which were subjected to enlargement processing by the enlargement circuit 2095, are inputted to the third matrix circuit 2097 without going through the highlighting circuit 2096.

Then, by the third matrix circuit 2097, conversion to three primary color signals R, G, B is carried out, and output to a color monitor not shown in the figure is performed.

Furthermore, the selector 2088 selects the luminance signal Yh at ordinary light observation via ordinary light, and selects the luminance signal that passed through the second matrix circuit 2094, that is, the luminance signal Ynbi, at narrowband-light observation via the illumination of narrowband light.

In the conventional video signal processing apparatus 2081, since signal processing that conforms to specifications of a standard video signal is carried out, broadband signal processing is implemented for the luminance signal Y, and low-band signal processing is implemented for the color signal C.

In the prior art shown in FIG. 48, image quality is ensured in ordinary-light observation, but the drawback is that the color signal C is processed as a low-band color signal in narrowband light observation, resulting in an image with low resolution.

Furthermore, because the illumination light is made narrowband at narrowband-light observation (NBI observation), the observation image becomes dark.

With the foregoing in mind, an object of the present embodiment and the fifth embodiment, which will be explained hereinbelow, is to provide an endoscope apparatus that can support ordinary-light observation, and achieve a good quality endoscopic image during narrowband-light observations as well.

An endoscope apparatus 2001 according to a fourth embodiment, as shown in FIG. 40, comprises an electronic endoscope (hereinafter, abbreviated as simply endoscope) 2002, which is inserted into a body cavity, and which carries out an endoscopic examination; a light-source apparatus 2003, which supplies illumination light to the endoscope 2002; a video processor 2004 as an endoscopic video signal processing unit, which drives image capturing means built into the endoscope 2002, and carries out signal processing relative to an output signal of image-capturing means; and a monitor 2005, which, in accordance with being inputted with a video signal outputted from the video processor 2004, displays an endoscopic image captured by image-capturing means.

The endoscope 2002 comprises a long, thin insertion unit 2007; an operation unit 2008, which is disposed at the back end of the insertion unit 2007; and a universal cable 2009, which extends from the operation unit 2008, and a light-guide connector 2011 at the end of the universal cable 2009 is removably connected to the light-source apparatus 2003, and a signal connector is removably connected to the video processor 2004.

A light guide 2013, which transmits illumination light, is inserted into the above-mentioned insertion unit 2007, and illumination light from the light-source apparatus 2003 is supplied to the light guide 2013 by connecting the light-guide connector 2011 of the light-source apparatus 2003 end of the light guide 2013 to the light-source apparatus 2003.

The light-source apparatus 2003 generates an illumination light of white light (visible region) as the ordinary illumination light in the ordinary-light observation mode, and supplies same to the light guide 2013, and generates narrowband illumination light in the narrowband-light observation mode, and supplies to the light guide 2013.

Switching instructions of the ordinary-light observation mode and narrowband-light observation mode, for example, can be executed by a scope switch or other such mode-switching switch 2014 provided to the operation unit 2008 of the endoscope 2002. Furthermore, in addition to being constituted by a scope switch provided to the endoscope 2002, the mode-switching switch 2014 can also be constituted by a foot switch, can be provided on the front panel of the video processor 2004, and can also be constituted by a keyboard not shown in the figure.

A switching signal from the mode-switching switch 2014 is inputted to the control circuit 2015 inside the video processor 2004, and when a switching signal is inputted, the control circuit 2015 controls the filter insertion/removal mechanism 2016 of the light-source apparatus 2003, and selectively switches between an ordinary illumination light and a narrowband illumination light.

Further, as will be explained hereinbelow, the control circuit 2015 operates in response to the switching control of the illumination light supplied to the light guide 2013 from the light-source apparatus 2003, and also executes control for switching the characteristics of the video signal processing system in the video processor 2004. Then, the control circuit 2015 is able to carry out signal processing respectively suitable for the ordinary-light observation mode and the narrowband-light observation mode by switching the characteristics of the video signal processing system by a switch operation via the mode-switching switch 2014.

The light-source apparatus 2003 is equipped with a lamp 2020 for generating an illumination light, and the lamp 2020 generates an illumination light including the visible light region. The illumination light, subsequent to having infrared light cut by an infrared cutting filter 2021, and being made into illumination light approaching a wavelength band of approximate white light, is irradiated onto a diaphragm 2022. The size of the opening of the diaphragm 2022 is adjusted by a diaphragm drive circuit 2023, thereby controlling the quantity of light passing therethrough.

The illumination light that has passed through the diaphragm 2022 either passes through a narrowband filter 2024, which is removably inserted into the illumination light path by the filter insertion/removal mechanism 2016 constituting a plunger or the like (in the narrowband-light observation mode), or does not pass through the narrowband filter 2024 (in the ordinary-light observation mode), is irradiated onto a condenser lens 2025, is condensed by the condenser lens 2025, and is irradiated onto the hand-side end face of the light guide 2013, that is, the incident end face.

FIG. 41 shows one example of the spectral characteristics of the narrowband filter 2024. The narrowband filter 2024 exhibits three-peak filter characteristics, and, for example, has the respective narrowband transmission filter characteristic sections Ra, Ga, Ba in the respective wavelength regions of red, green and blue.

More specifically, the narrowband transmission filter characteristic sections Ra, Ga, Ba have bandpass characteristics in which the respective center wavelengths are 600 nm, 540 nm and 420 nm, and the full widths at half maximum thereof are between 20 nm and 40 nm.

Therefore, when the narrowband filter 2024 is positioned in the illumination light path, three bands of narrowband illumination light, which permeate the narrowband transmission filter characteristic sections Ra, Ga, Ba, are irradiated into the light guide 2013.

By contrast, when the narrowband filter 2024 is not positioned in the illumination light path, white light is supplied to the light guide 2013.

The illumination light from the light guide 2013 is transmitted by the light guide 2013 to the distal end face thereof, and is outputted to the outside by way of an illumination lens 2027 mounted to an illumination window provided at the distal end face 2026 of the insertion unit 2007, and illuminates the surface of living tissue inside a patient's body cavity.

An observation window is provided adjacent to the illumination window in the distal end face 2026, and an objective lens 2028 is mounted to the observation window. The objective lens 2028 provides an optical image by reflected light from the living tissue. A charge-coupled device (abbreviated CCD) 2029 is arranged as a solid-state image-capturing device at the imaging location of the objective lens 2028, and the CCD 2029 performs photoelectric transfer.

For example, the complementary color filter shown in FIG. 42 is mounted in pixel units to the image-capturing surface of the CCD 2029 as a color separation filter 2030 for separating colors optically.

The four color chips of the complementary color filter, magenta (Mg), green (G), cyan (Cy) and yellow (Ye), are positioned in front of each pixel, with Mg and G being alternately arranged in the horizontal direction, and the arrays Mg, Cy, Mg, Ye and G, Ye, G, Cy being arranged in that order in the vertical direction.

Then, the CCD 2029, which uses the complementary color filter, is constituted so as to add and sequentially read out the two rows of pixels adjacent to one another in the vertical direction, reading out the rows of pixels by staggering the even and odd fields. As is known, luminance and color difference signals are then generated by the color separation circuit in the subsequent stage.

The above-mentioned CCD 2029 is connected to one end of a signal line, and by connecting a signal connector, which is connected to the other end of the signal line, to the video processor 2004, CCD 2029 is connected to a CCD drive circuit 2031 and CDS circuit 2032 inside the video processor 2004.

Furthermore, each endoscope 2002 comprises an ID generation unit 2033, which generates specific identification information (ID) to the endoscope 2002, and an ID by the ID generation unit 2033 is inputted to the control circuit 2015, and the control circuit 2015 uses the ID to identify the type of endoscope 2002 connected to the video processor 2004, and the number and type of pixels of the CCD 2029 built into the endoscope 2002.

Then, the control circuit 2015 controls a CCD drive circuit 2031 so as to properly drive the CCD 2029 of the identified endoscope 2002.

The CCD 2029 inputs an image-capturing signal, which has undergone photoelectric transfer, to correlated double sampling circuit (abbreviated CDS circuit) 2032 in accordance with the application of a CCD drive signal from the CCD drive circuit 2031. After a signal component has been extracted from the image-capturing signal and converted to a baseband signal by the CDS circuit 2032, the baseband signal is inputted to an A/D conversion circuit 2034, converted to a digital signal, and inputted to a brightness detection circuit 2035, which detects brightness (the average luminance of a signal).

A brightness signal detected by the brightness detection circuit 2035 is inputted to a light modulation circuit 2036, and a modulated-light signal is generated for carrying out light modulation in accordance with the difference with a reference brightness (target value of modulated light). The modulated-light signal from the light modulation circuit 2036 is inputted to the diaphragm drive circuit 2023, and the size of the opening of the diaphragm 2022 is adjusted so as to achieve the reference brightness.

A digital signal outputted from the A/D conversion circuit 2034 is inputted to a Y/C separation circuit 2037, and a luminance signal Y and line-sequential color difference signals Cr (=2R−G) and Cb (=2B−G) (as broadly defined color signals C) are generated. The luminance signal Y is inputted to a selector 2039 via a γ circuit 2038 (the luminance signal is notated as Yh), and, in addition, is inputted to a first low-pass filter (abbreviated LPF) 2041, which restricts the pass band of the signal.

The LPF 2041 is set to a broad pass band corresponding to the luminance signal Y, and a luminance signal Y1 of the band set by the pass band characteristics of the LPF 2041 is inputted to a first matrix circuit 2042.

Further, the color difference signals Cr, Cb are inputted to a (line-sequential) synchronization circuit 2044 via a second LPF 2043 for restricting the pass bands of the signals.

In this case, the second LPF 2043 changes the pass band characteristics thereof in accordance with the observation mode by the control circuit 2015. More specifically, in the ordinary-light observation mode, the second LPF 2043 is set to a lower band than the first LPF 2041.

Meanwhile, in the narrowband-light observation mode, the second LPF 2043 is changed to a broader band than the low band for the ordinary-light observation mode. For example, the second LPF 2043 is set (changed) to a broadband that is practically the same as that of the first LPF 2041. Thus, the second LPF 2043 operates in response to the switching of the observation mode, forming processing characteristic changing means for changing the processing characteristics that restrict the pass band for the color difference signals Cr, Cb.

The synchronization circuit 2044 generates synchronized color difference signals Cr, Cb, and the color difference signals Cr, Cb are inputted to the first matrix circuit 2042.

The first matrix circuit 2042 converts the luminance signal Y and color difference signals Cr, Cb to three primary color signals R, G, B, and outputs to the γ circuit 2045.

Further, the first matrix circuit 2042 is controlled by the control circuit 2015, and the value of matrix coefficients (determining the conversion characteristics) corresponding to the characteristics of the color separation filter 2030 of the CCD 2029, or the characteristics of the narrowband filter 2024 is changed, and conversion to three primary color signals R1, G1, B1, which are not mixed colors or have had mixed colors eliminated for the most part, is performed.

For example, there are cases where the characteristics of the color separation filter 2030 of the CCD 2029 mounted in the endoscope 2002, which is actually connected to the video processor 2004, are different, and the control circuit 2015 changes the coefficients of the first matrix circuit 2042 in accordance with the characteristics of the color separation filter 2030 of the CCD 2029 that is actually being used according to the ID information, thus making it possible to appropriately deal with a situation in which the types of image-capturing means actually being used differ, making it possible to prevent the generation of pseudo-colors, and to convert to three primary color signals R1, G1, B 1 that are not mixed colors.

Furthermore, generating three primary color signals R1, G1, B1, which are not mixed colors, has the operational advantage of making it possible to effectively prevent a color signal, the image of which was captured under narrowband light of a specific color, from becoming difficult to be identified due to a color signal that was captured under a narrowband light of another color.

In other words, in the prior art shown in FIG. 48, the drawback is that a plurality of image components captured under respective narrowband lights respectively set in each of the wavelength bands of R, G, and B blend together to produce a mixed color, thereby obscuring the characteristic feature of an image component corresponding to a specific narrowband light of note, but the present embodiment makes it possible to prevent mixed colors that result in this kind of obscuring.

Further, preventing the mixing of colors can also make it possible in subsequent stages to produce a display by increasing the ratio of a noteworthy image component corresponding to a specific narrowband light, and to produce a display using only a noteworthy image component corresponding to a specific narrowband light, thereby also making it possible to produce an image display that clearly reflects the characteristic features of a noteworthy image component corresponding to a specific narrowband light.

The γ circuit 2045 is also controlled by the control circuit 2015. Specifically, in the narrowband-light observation mode, the control circuit 2015 changes a γ correction characteristic to a γ characteristic that is highlighted more than in the ordinary-light observation mode. Thus, the contrast at the low signal level side is highlighted, making for display characteristics that are easier to identify. Three primary color signals R2, G2, B2, which have undergone γ correction by the γ circuit 2045, are inputted to the second matrix circuit 2046, and the second matrix circuit 2046 converts the three primary color signals R2, G2, B2 to a luminance signal Y and color difference signals R-Y, B-Y.

In this case, the control circuit 2015 sets matrix coefficients of the second matrix circuit 2046 so as to simply convert the three primary color signals R2, G2, B2 to a luminance signal Y and color difference signals R-Y, B-Y in the ordinary-light observation mode.

In the narrowband-light observation mode, the control circuit 2015 changes matrix coefficients of the second matrix circuit 2046 from the value of the ordinary-light observation mode, setting this value such that a luminance signal Ynbi, which increases the ratio (weight) for the B signal in particular, and color difference signals R-Y, B-Y are generated from the three primary color signals R2, G2, B2.

The conversion equation in this case is as follows when using three-row, three-column matrices A and K.

$$\begin{pmatrix} Ynbi \\ R-Y \\ B-Y \end{pmatrix} = A \begin{pmatrix} 0 & k1 & 0 \\ 0 & 0 & k2 \\ 0 & 0 & k3 \end{pmatrix} \begin{pmatrix} R2 \\ G2 \\ B2 \end{pmatrix} \quad (4)$$

Here, matrix K, for example, comprises three real components k1 through k3 (the other component is 0), and, a conversion equation like Equation (4) increases the weight of G and B color signals relative to the R color signal, and maximizes the weight (ratio) of the color signal of B in particular. In other words, equation (4) suppresses the long-wavelength R color signal, and highlights the short-wavelength B color signal.

Further, A is a matrix for converting from an RGB signal to Y and color difference signals, and the following known operation coefficients (5) can be used.

$$A = \begin{pmatrix} 0.299 & 0.587 & 0.114 \\ -0.299 & -0.587 & 0.886 \\ 0.701 & -0.587 & -0.114 \end{pmatrix} \quad (5)$$

The luminance signal Ynbi outputted by the second matrix circuit 2046 is inputted to the selector circuit 2039. The switching of the selector 2039 is controlled by the control circuit 2015. That is, the control circuit 2015 selects luminance signal Yh in the ordinary-light observation mode, and selects luminance signal Ynbi in the narrowband-light observation mode.

The color difference signals R-Y, B-Y outputted from the second matrix circuit 2046 are inputted to an enlargement circuit 2047 together with either a Yh or Ynbi (notated as Yh/Ynbi) luminance signal that has passed through the selector 2039.

A luminance signal Yh/Ynbi, which has undergone enlargement processing by the enlargement circuit 2047, is inputted to a third matrix circuit 2049 subsequent to undergoing contour highlighting by a highlighting circuit 2048, and the color difference signals R-Y, B-Y, which underwent enlargement processing by the enlargement circuit 2047, are inputted to the third matrix circuit 2049 without passing through the highlighting circuit 2048.

Then, the luminance signal Yh/Ynbi and color difference signals R-Y, B-Y are converted to three primary color signals R, G, and B by the third matrix circuit 2049, and thereafter, the three primary color signals R, G, B are converted to analog video signals by a D/A conversion circuit not shown in the figure, and outputted to the monitor 2005 from a video signal output terminal.

Furthermore, the contour highlighting by the highlighting circuit 2048 may have highlighting characteristics changed corresponding to CCD 2029 and type of color separation filter 2030 and the like (the highlighting band can be changed to a medium/low band, or it can be changed to a medium/high band).

In particular, the luminance signal Ynbi is subjected to highlight processing in the narrowband-light observation mode. In this case, when equation (5) is employed, processing is carried out for highlighting the structure of capillary vessels and the like in the vicinity of the superficial portion of a living tissue via the B signal as will be explained below, making it possible to clearly display a noteworthy image component.

Furthermore, the three primary color signals R, G, B, which are actually inputted to the respective R, G, B channels of the monitor 5 from the video signal output terminal, constitute G, B, B signals (weighting differs according to the coefficients) when equation (5) is employed in the narrowband-light observation mode, and more particularly, the ratio of the B signal becomes the largest, making it possible to display in an easy-to-identify state via a B signal an endoscopic image corresponding to the structure of a capillary vessel in the vicinity of a superficial portion of a living tissue.

In other words, the signals respectively inputted to the RGB channels of the monitor 5 in the narrowband-light observation mode actually constitute G, B, B signals (apart from the value of the coefficients).

Thus, a feature of the present embodiment is the formation of processing characteristic changing means for changing a processing characteristic of a signal processing system of the video processor 2004 (more specifically, a signal processing system other than the Y/C separation circuit 2037) so as to be able to carry out signal processing that is suited to the respective observation modes by operating in response to the switching of the observation modes.

In this case, a characteristic feature is that it is possible to carry out processing that is suitable to both observation modes by changing the processing characteristics in practically compatible processing circuits without providing a dedicated processing circuit for each observation mode, enabling both observation modes to be appropriately supported using a simple configuration.

Operations according to the present embodiment will be explained hereinbelow by referring to FIG. 43.

An operator connects an endoscope 2002 to the light-source apparatus 2003 and video processor 2004 as shown in FIG. 40, and turns on the power, and the control circuit 2015 of the video processor 2004 starts initialization processing, and as shown in Step S21, for example, sets the ordinary-light observation mode as the operation mode of the light-source apparatus 2003 and video processor 2004.

In this state, the light-source apparatus 2003 is set such that the narrowband filter 2024 is separated from the illumination light path as indicated by the solid line in FIG. 40, constituting a state in which image capturing is performed by the endoscope 2002 under white illumination light. Further, the respective parts of the video processor 2004 are also set to perform signal processing in the state of the ordinary-light observation mode.

An operator inserts the insertion unit 2007 of the endoscope 2002 into a body cavity of a patient, making it possible to conduct an endoscopic examination. When he wants to observe in more detail the course of the surface blood vessels of a tissue targeted for examination, such as a diseased part of the body cavity, the operator operates the mode-switching switch 2014.

As shown in step S22, the control circuit 2015 monitors whether or not the mode-switching switch 2014 has been operated, and when the mode-switching switch 2014 has not been operated, it maintains the status, and when the mode-switching switch 2014 has been operated, it proceeds to the next step S23.

In step S23, the control circuit 2015 changes the operation mode of the light-source apparatus 2003 and video processor 2004 to the setting state of the narrowband-light observation mode.

More specifically, the control circuit 2015 performs control relative to the light-source apparatus 2003 such that the narrowband filter 2024 is positioned in the illumination light path as indicated by the two-dot chain line in FIG. 40. As indicated by the transmittance characteristics shown in FIG. 41, positioning the narrowband filter 2024 in the path of the illumination light results in illumination by a narrowband illumination light in accordance with the narrowband transmission filter characteristic sections Ra, Ga, Ba.

Further, the control circuit 2015 changes the settings of the respective parts of the video processor 2004. More specifically, the control circuit 2015 carries out changes and settings so as to make the band characteristics of the LPF 2043 broadband, change the matrix coefficients of the first matrix circuit 2042 such that a mixed color is not generated, change a γ characteristics of the γ circuit 2045, change the matrix coefficients of the second matrix circuit 2046 so as to increase the ratio of the signal component of a B color signal (according to the narrowband transmission filter characteristic section Ba) in particular, and switch the selector 2039 such that luminance signal Ynbi is selected.

By making changes and settings like this, the matrix coefficients of the second matrix circuit 2046, for example, are changed to processing characteristics, which increase the ratio of the signal components of a B color signal in particular, thereby making it possible to display in an easy-to-identify state the course of a capillary vessel in the vicinity of a superficial portion of a living tissue achieved by a B color signal, the image of which was captured under B illumination light via the narrowband transmission filter characteristic section Ba.

Further, since the band characteristics of the signal passband of LPF 2043 are made broadband, it is possible to enhance the resolution (resolving power) of the course of a capillary vessel, and the course of a blood vessel in the vicinity of a superficial portion achieved by a G color signal, the image of which was captured under G illumination light approaching the luminance signal via the narrowband transmission filter characteristic section Ga.

In the next step S24, the control circuit 2015 monitors whether or not the mode-switching switch 2014 has been operated, and when the mode-switching switch 2014 has not been operated, maintains the status, and when the mode-switching switch 2014 has been operated, returns to the next step S21.

According to the present embodiment, which operates like this, retaining a color image-capturing function in accordance with an existing synchronous system and changing processing characteristics, such as changing the coefficients and other settings of the respective parts of the video processor 2004, in the ordinary-light observation mode, makes it possible to ensure full observation functions in the narrowband-light observation mode.

That is, in the prior art, preventing a drop in resolving power makes it possible to achieve an endoscopic image having good resolution, and to more clearly display in an easy-to-identify state the course of a capillary vessel, the image of which was captured under a B narrowband illumination light (which, for example, was apt to be buried in the prior art due to the signal having its image captured under R narrowband illumination light).

Further, according to the present embodiment, it is possible to readily support both the ordinary-light observation mode and the narrowband-light observation mode by switching the processing characteristics of a portion of the signal processing system, thereby achieving an apparatus that is extremely convenient and useful during an endoscopic examination.

Further, a light-source apparatus of a narrowband light can be readily formed by providing in the light-source apparatus 2003 means for removably inserting a narrowband filter 2024 in the optical path, in addition to ordinary-light illumination means.

A first variation of the fourth embodiment will be explained next. In the fourth embodiment, multiplication processing is reduced by using a first matrix circuit 2042 to carry out processing as below.

The above-mentioned first matrix circuit 2042 generates three primary color signals R1, G1, B1 from an inputted luminance signal Y and color difference signals Cr, Cb.

In this case, the matrix operation equation by the first matrix circuit 2042 uses a three-row, three-column matrix M (matrix coefficients m11 through m33), and generally is as follows.

$$\begin{pmatrix} R1 \\ G1 \\ B1 \end{pmatrix} = \begin{pmatrix} m11 & m12 & m13 \\ m21 & m22 & m23 \\ m31 & m32 & m33 \end{pmatrix} \begin{pmatrix} Y \\ Cr \\ Cb \end{pmatrix} \quad (6)$$

Meanwhile, the luminance signal Y and color difference signals Cr, Cb inputted to the first matrix circuit 2042 have the characteristics generally depicted in FIG. 44.

If the ratios (percentages) of the contributions of luminance signal Y and color difference signals Cr and Cb relative to the respective bands of R, G, and B in FIG. 44 are taken into account when carrying out the operation of the above equation (6), the following approximations can be made. The ratio contributed by color difference signal Cb in the R band in FIG. 44 can be approximated as 0, which is sufficiently smaller than those of the others.

That is, the above-mentioned coefficient m13 can be approximated as 0. Further, the ratio contributed by color difference signal Cr in the G band can be approximated as a sufficiently small 0. That is, the above-mentioned coefficient m22 can be approximated as 0.

Further, the ratio contributed by color difference signal Cr in the B band can be approximated as a sufficiently small 0. That is, the above-mentioned coefficient m32 can be approximated as 0.

Therefore, the following equation can be employed as the above-mentioned matrix M.

$$M = \begin{pmatrix} m11 & m12 & 0 \\ m21 & 0 & m23 \\ m31 & 0 & m33 \end{pmatrix} \quad (7)$$

The coefficients of the matrix M are shown in FIG. 45(A). Further, the coefficients of the matrix M can also be approximated from the characteristics of FIG. 44 as in FIG. 45(B), FIG. 45(C), and FIG. 45(D). By approximating like this, it becomes possible to reduce or simplify the configuration of the multiplier of the first matrix circuit 2042, enabling high-speed processing and lower costs.

Next, a second variation of the fourth embodiment will be explained. In the above explanation, the narrowband filter 2024 employed a three-peak filter, but a two-peak filter such as that below can also be used.

A filter with transmittance characteristics like those shown in FIG. 46 can be employed as the narrowband filter 2024B in the second variation. The narrowband filter 2024B is a two-peak filter, and it has the respective narrowband transmission filter characteristic sections Ga and Ba in the G and B wavelength regions. That is, this filter does not provide the narrowband transmission filter characteristic section Ra of the three-peak narrowband filter 2024 in the fourth embodiment.

More specifically, the narrowband transmission filter characteristic sections Ga, Ba have bandpass characteristics in which the center wavelengths are 420 nm and 540 nm, respectively, and the full widths at half maximum are between 20 nm and 40 nm.

Therefore, when the narrowband filter 2024B is positioned in the illumination light path, the two-band narrowband illumination light, which permeates the narrowband transmission filter characteristic sections Ga, Ba thereof is irradiated into the light guide 2013.

The matrix operation equation of the first matrix circuit 2042 in this case uses a two-row, three-column matrix M, and generally is as follows.

$$\begin{pmatrix} G1 \\ B1 \end{pmatrix} = \begin{pmatrix} m21 & m22 & m23 \\ m31 & m32 & m33 \end{pmatrix} * \begin{pmatrix} Y \\ Cr \\ Cb \end{pmatrix} \quad (8)$$

Meanwhile, the luminance signal Y and color difference signals Cr, Cb inputted to the first matrix circuit 2042 have the characteristics depicted in FIG. 44. Then, carrying out approximation the same way as expressed in equation (7) makes it possible to approximate the coefficients m22 and m32 as 0.

That is, in this case, the equation becomes as follows.

$$M = \begin{pmatrix} m21 & 0 & m23 \\ m31 & 0 & m33 \end{pmatrix} \quad (9)$$

This is depicted in FIG. 47(A). Further, carrying out approximation via another method makes it possible to use a coefficient matrix M such as coefficients of FIG. 47(B) and FIG. 47(C).

Approximating a portion of the coefficients of the matrix M as 0 like this makes it possible to reduce the number of multipliers. Further, it also has the effect of enabling matrix computations to be processed faster. In addition, using a two-peak filter also makes it possible to lower the cost of an expensive narrowband filter.

Fifth Embodiment

Figure 49:
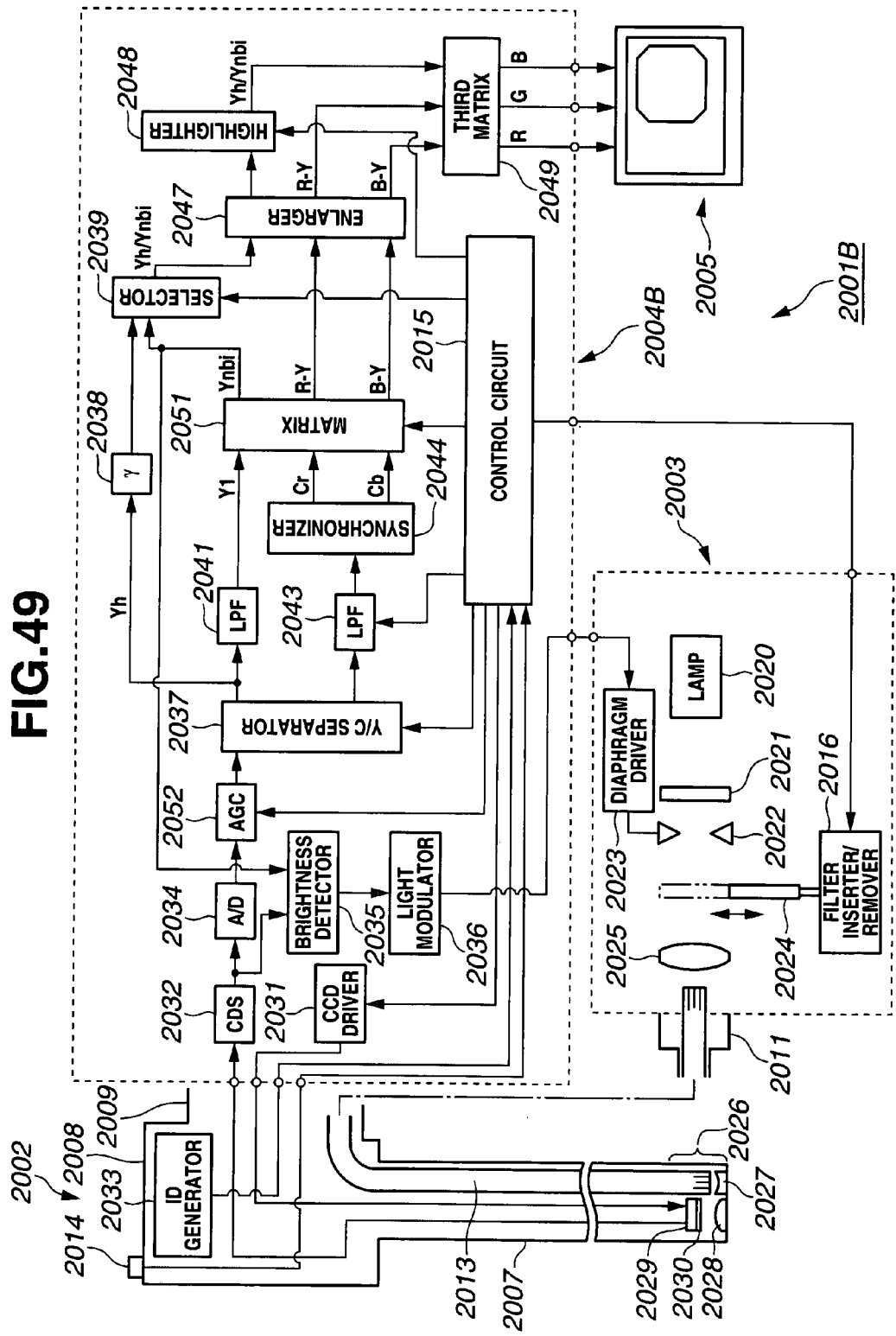
FIG. 49 is a block diagram showing a configuration of an endoscope apparatus according to a fifth embodiment of the present invention.

Next, a fifth embodiment of the present invention will be explained by referring to FIG. 49. FIG. 49 shows an endoscope apparatus 2001B according to the fifth embodiment of the present invention. Since the fifth embodiment is practically the same as the fourth embodiment, only the points of difference will be explained, and an explanation of identical components having the same reference numerals will be omitted.

The endoscope apparatus 2001B employs a video processor 2004B that changes a portion of the video processor 2004 of FIG. 40. The video processor 2004B configures the first matrix circuit 2042, γ circuit 2045, and second matrix circuit 2046 in the video processor 2004 of FIG. 40 into a single matrix circuit 2051.

Then, the control circuit 2015 changes the matrix coefficients of the matrix circuit 2051 the same as it changed a γ characteristic of the γ circuit 2045 and the matrix coefficients of the second matrix circuit 2046 by switching signals via the mode-switching switch 2014 as explained in the fourth embodiment.

When the observation mode is switched from the ordinary-light observation mode to the narrowband-light observation mode, processing for performing a conversion without mixed colors, for changing a γ characteristic, and for performing a conversion, which suppresses a long-wavelength color signal (highlights a short-wavelength color signal) is collectively carried out by changing the coefficients of the matrix circuit 2051.

Further, an AGC circuit 2052, which applies auto-gain control to the signal level of input signals, is provided between the A/D conversion circuit 2034 and the Y/C separation circuit 2037.

Further, the configuration is such that an output signal of the CDS circuit 2032, and a luminance signal Ynbi from the matrix circuit 2051 are inputted to the brightness detection circuit 2035. Also, the control circuit 2015 changes the AGC gain and the follow-up speed of the AGC circuit 2052 in accordance with the observation mode by switching the mode-switching switch 2014.

Specifically, in the narrowband-light observation mode, the control circuit 2015 sets the AGC gain of the AGC circuit 2052 higher than it was in the ordinary-light observation mode, and, for example, also sets the follow-up speed of AGC gain control slower than the diaphragm control speed of the diaphragm 2022 of the light-source apparatus 2003. This gives priority to the light modulation operation of the diaphragm 2022 over the signal gain control operation of the AGC circuit 2052.

Further, the control circuit 2015 also switches the reference brightness (target light modulation value) in the light modulation circuit 2036 in the ordinary-light observation mode and in the narrowband-light observation mode.

By doing thus, light modulation is carried out giving priority to the light modulation operation of the diaphragm 2022 in the light-source apparatus 2003. When light modulation cannot be adequately performed by the diaphragm 2022 in accordance with this light modulation operation, an auto-gain control operation is supplementary carried out by the AGC circuit 2052.

Specifically, since the AGC circuit 2052 is designed to function when the diaphragm 2022 is open and the quantity of illumination light is at the maximum but the brightness is still not sufficient, (prior to the diaphragm 2022 opening) the AGC circuit 2052 operates, making it possible to prevent S/N degradation, and to achieve an endoscopic image of appropriate brightness.

According to the present embodiment, the configuration is such that, in addition to the operational advantages of the fourth embodiment, it is also possible to prevent S/N degradation, and to achieve an endoscopic image of appropriate brightness, particularly in the narrowband-light observation mode.

Sixth Embodiment

Figure 50:
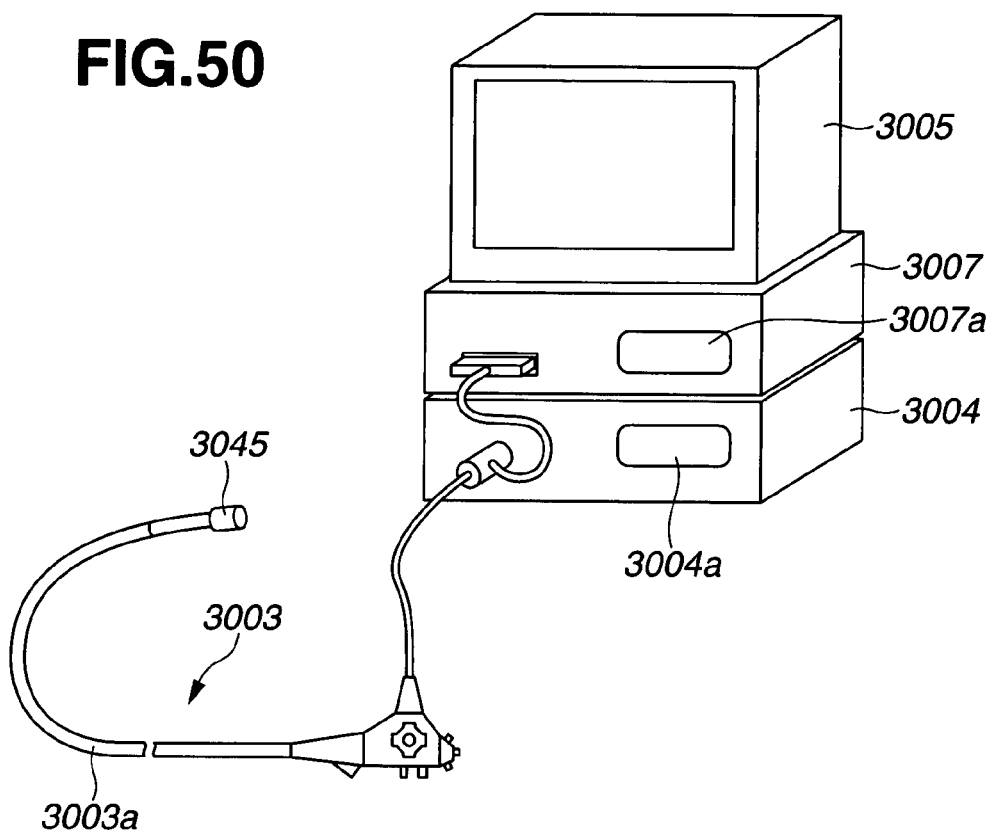
FIG. 50 is an external view showing the external configuration of an endoscope apparatus related to the first embodiment of the present invention.
Figure 51:
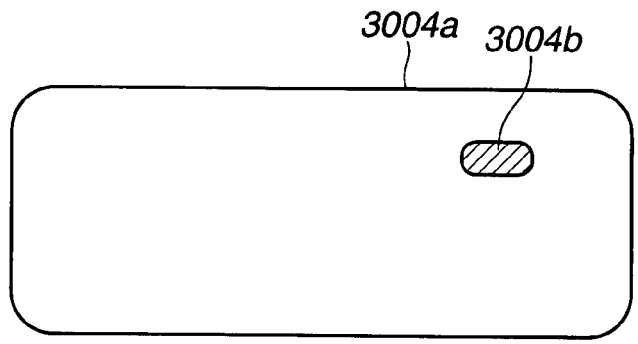
FIG. 51 is a diagram showing the front panel of the light-source apparatus of FIG. 50.
Figure 52:
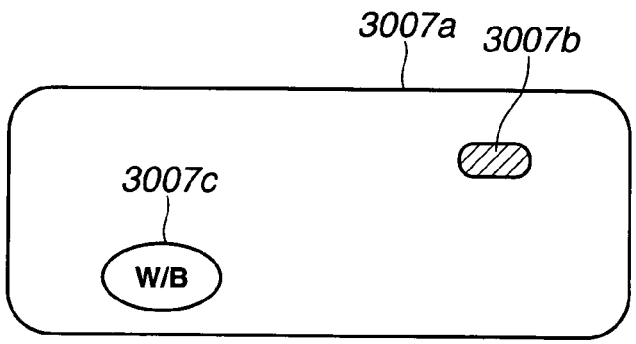
FIG. 52 is a diagram showing the front panel of the video processor of FIG. 50.
Figure 53:
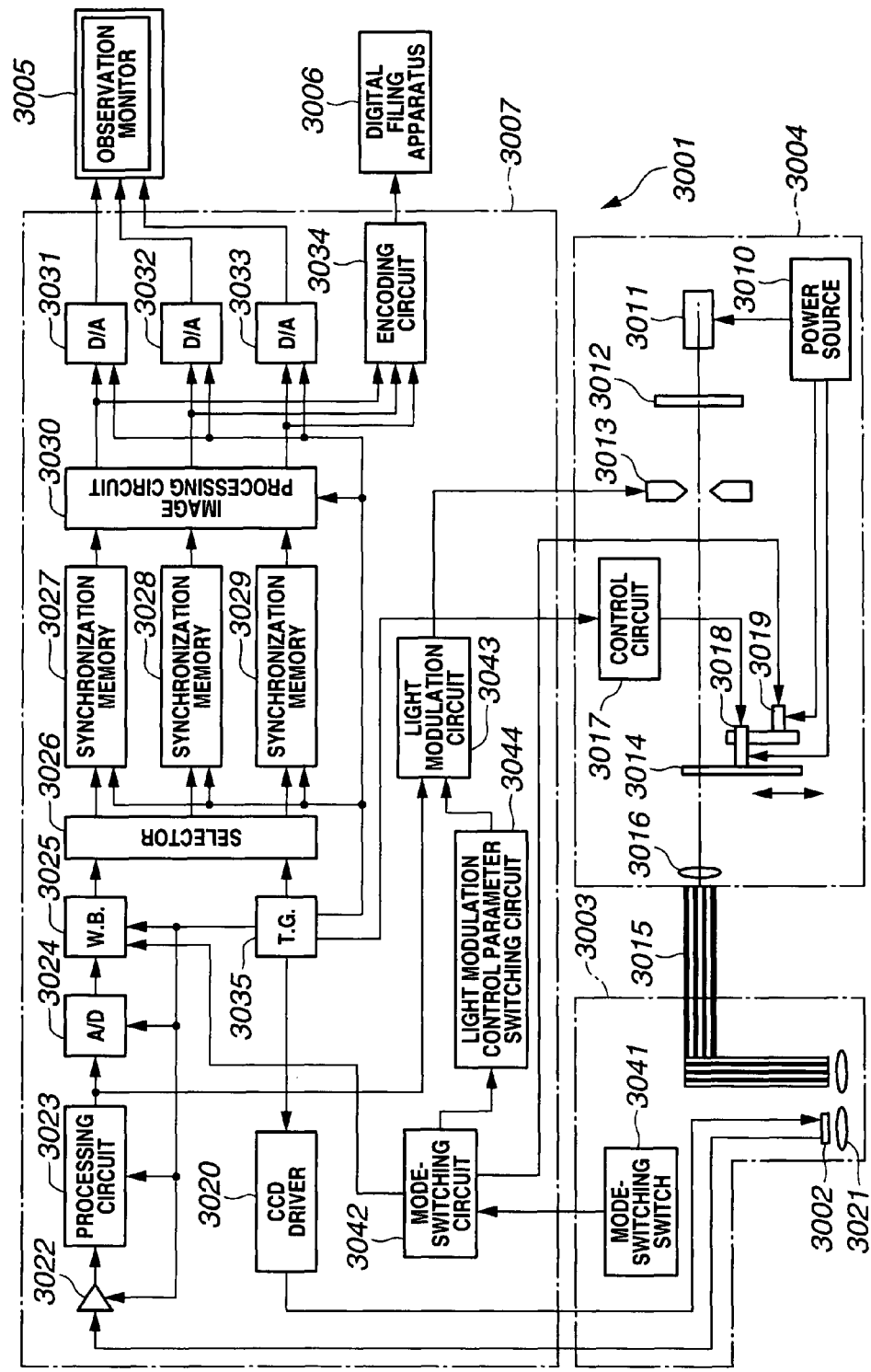
FIG. 53 is block diagram showing a configuration of the endoscope apparatus of FIG. 50.
Figure 54:
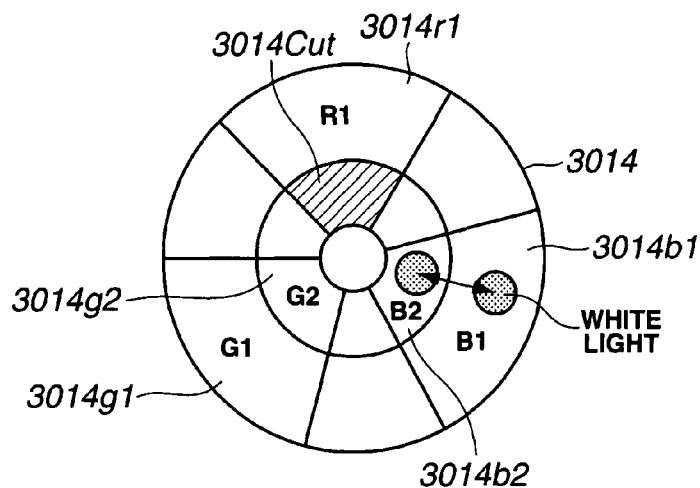
FIG. 54 is a block diagram showing a configuration of the rotating filter of FIG. 53.
Figure 55:
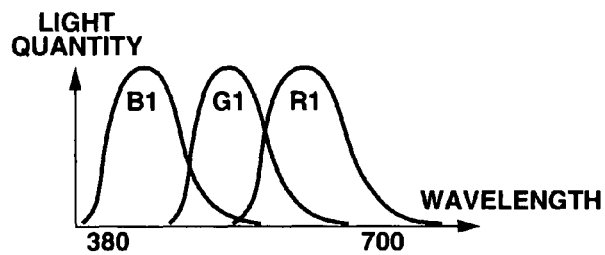
FIG. 55 is a diagram showing the spectral characteristics of a first filter group of the rotating filter of FIG. 54.
Figure 56:
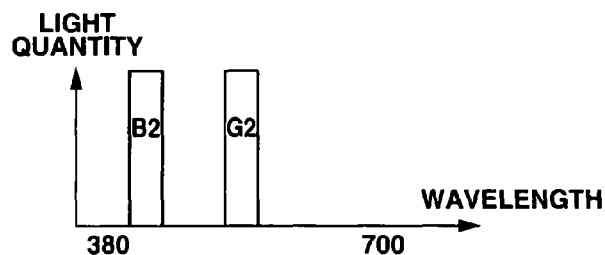
FIG. 56 is a diagram showing the spectral characteristics of a second filter group of the rotating filter of FIG. 54.
Figure 57:
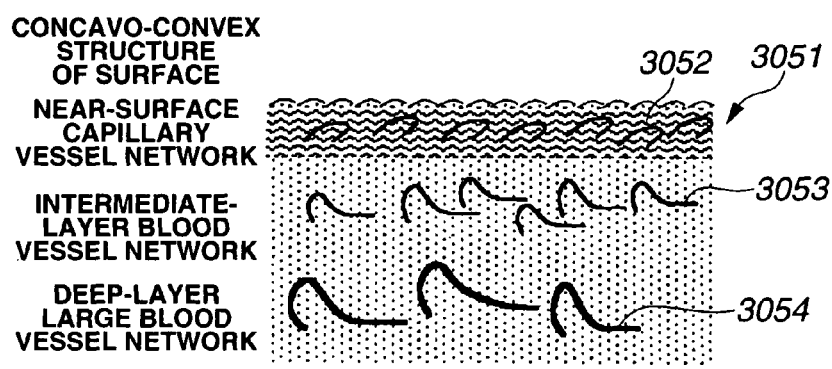
FIG. 57 is a diagram showing the layered structure of a living tissue observed via the endoscope apparatus of FIG. 53.
Figure 58:
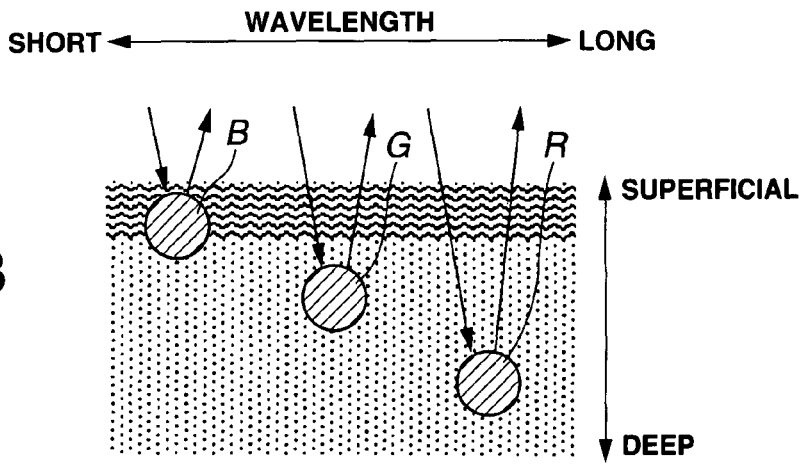
FIG. 58 is a diagram illustrating the access state in the direction of the layers of a living tissue of illumination light from the endoscope apparatus of FIG. 53.
Figure 59:
FIG. 59 is a first diagram showing the respective band images resulting from the surface-sequential light permeating the first filter group of FIG. 55.
Figure 60:
FIG. 60 is a second diagram showing the respective band images resulting from the surface-sequential light permeating the first filter group of FIG. 55.
Figure 61:
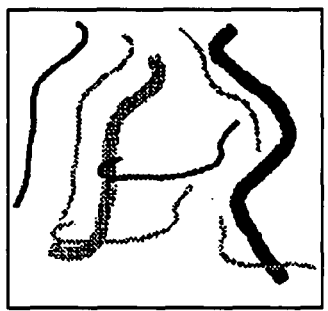
FIG. 61 is a third diagram showing the respective band images resulting from the surface-sequential light permeating the first filter group of FIG. 55.
Figure 62:
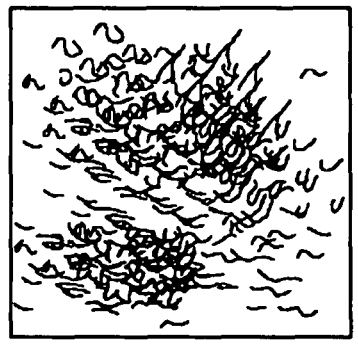
FIG. 62 is a first diagram showing the respective band images resulting from the surface-sequential light permeating the second filter group of FIG. 56.
Figure 63:
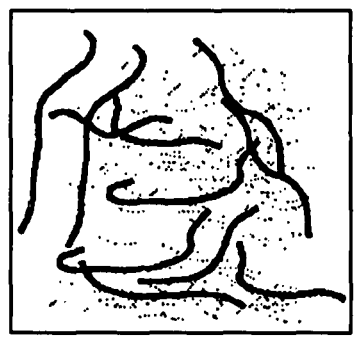
FIG. 63 is a second diagram showing the respective band images resulting from the surface-sequential light permeating the second filter group of FIG. 56.
Figure 64:
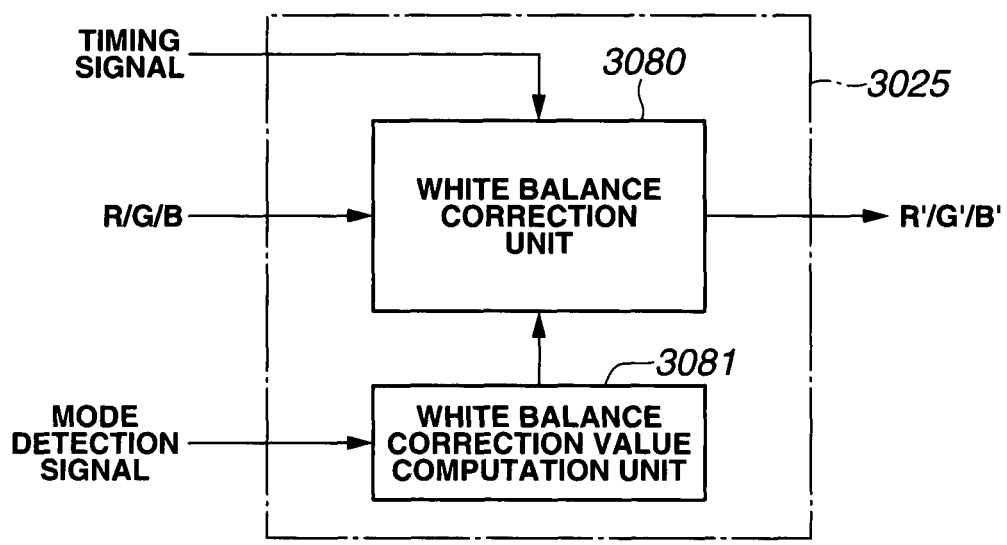
FIG. 64 is a block diagram showing a configuration of the white balance circuit of FIG. 53.
Figure 65:
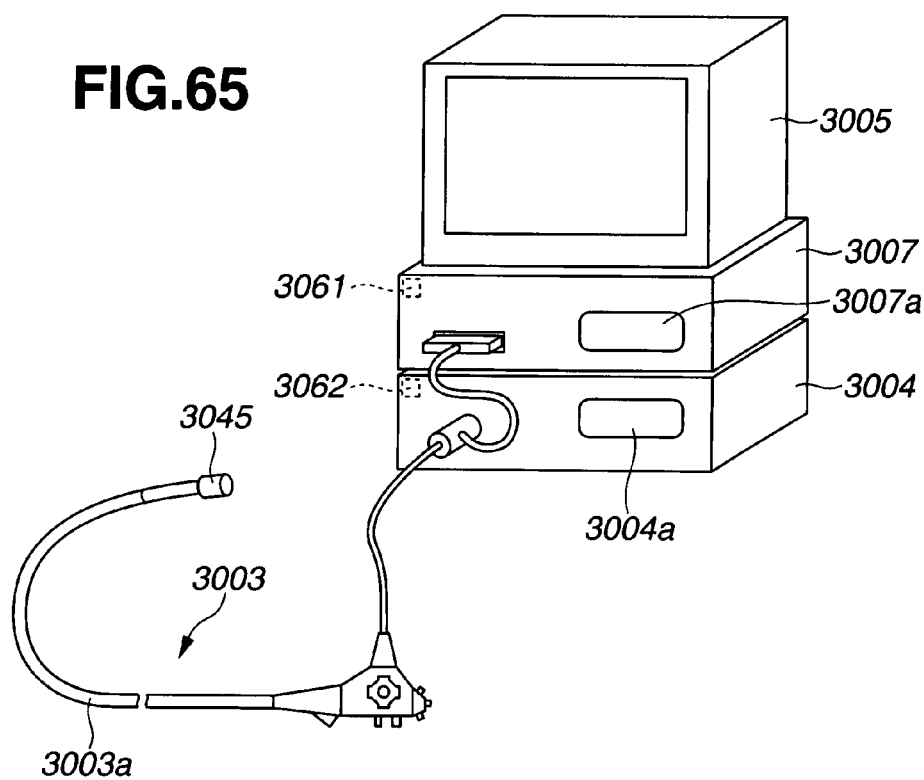
FIG. 65 is an external view showing the external configuration of a first variation of the endoscope apparatus of FIG. 50.
Figure 66:
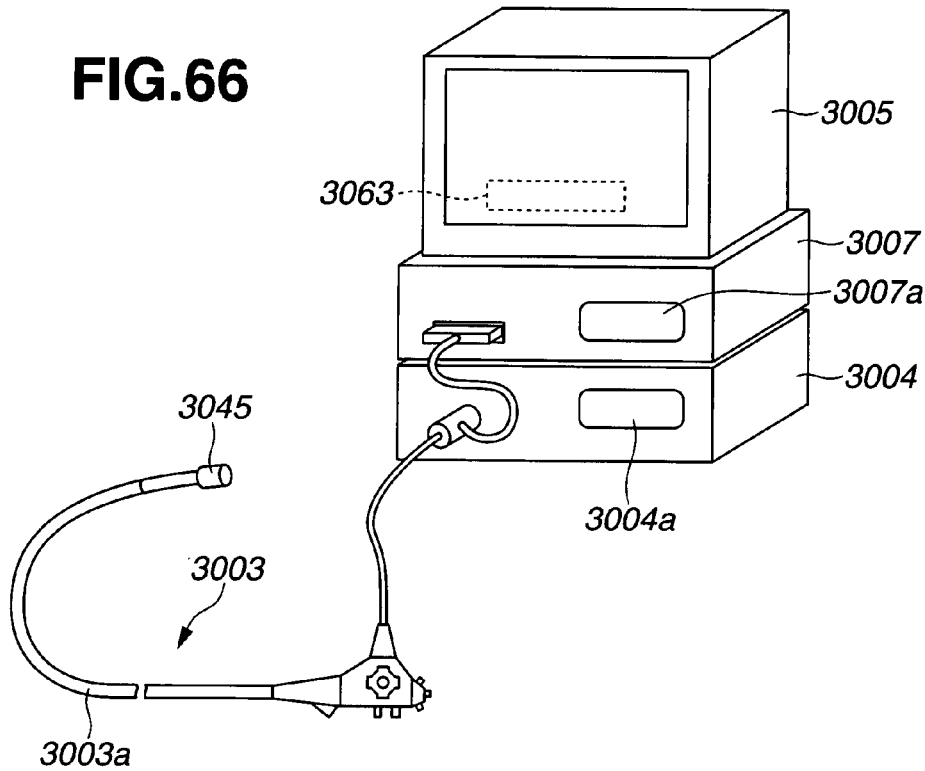
FIG. 66 is an external view showing the external configuration of a second variation of the endoscope apparatus of FIG. 50.
Figure 67:
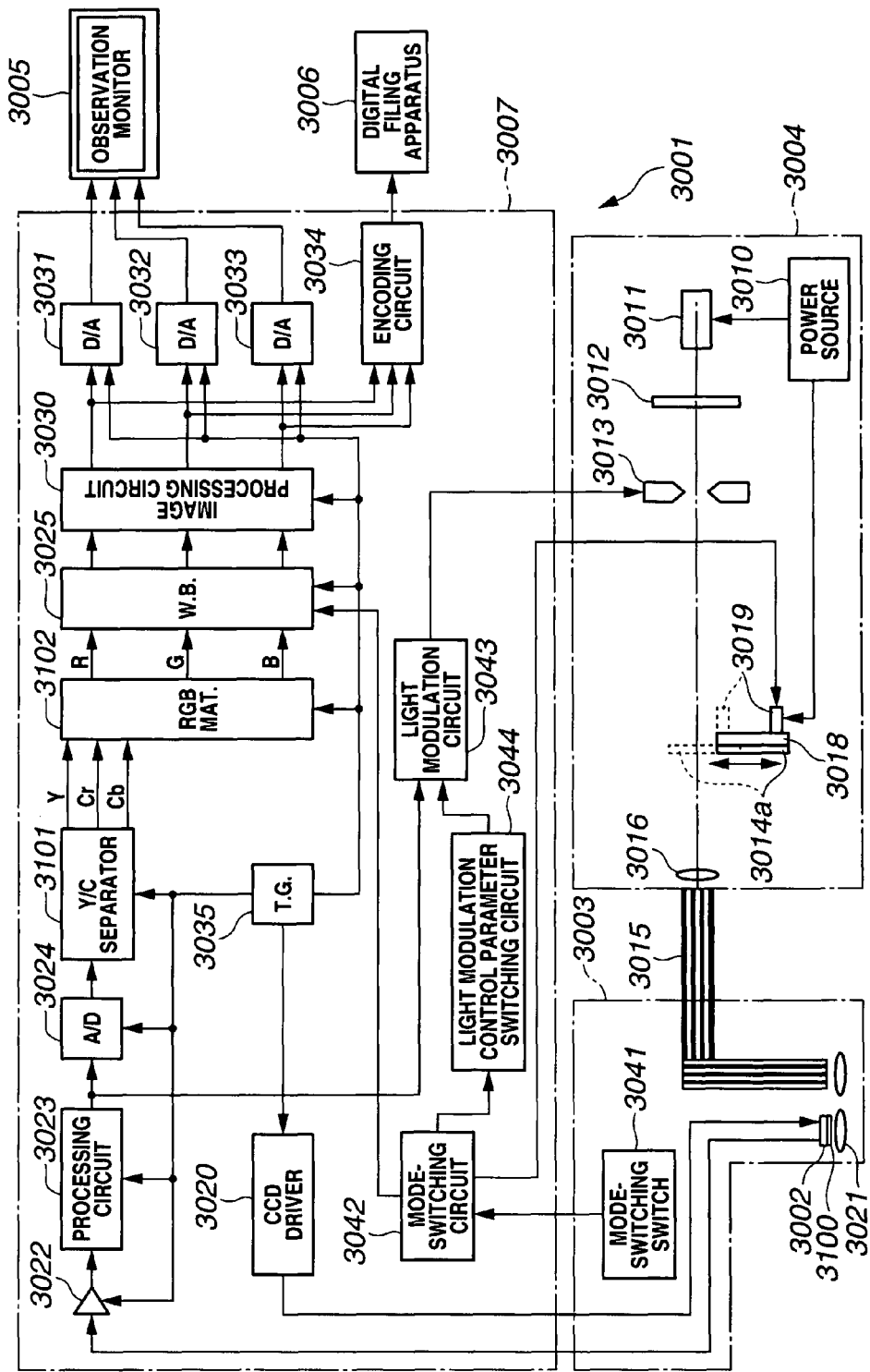
FIG. 67 is a block diagram showing a configuration of a synchronous-type endoscope apparatus, which is a variation of the endoscope apparatus of FIG. 53.
Figure 68:
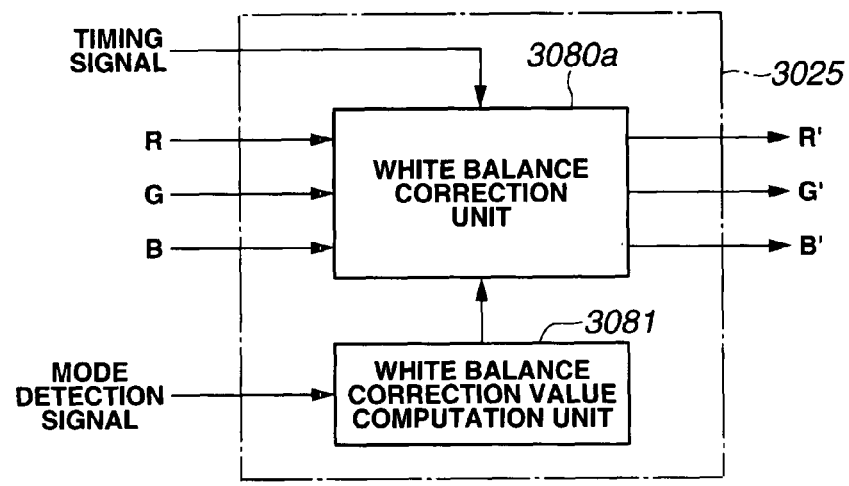
FIG. 68 is a block diagram showing a configuration of the white balance circuit of FIG. 67.

FIGS. 50 through 68 are related to a sixth embodiment of the present invention. FIG. 50 is an external view showing the external configuration of an endoscope apparatus; FIG. 51 is a diagram showing the front panel of the light-source apparatus of FIG. 50; FIG. 52 is a diagram showing the front panel of the video processor of FIG. 50; FIG. 53 is block diagram showing a configuration of the endoscope apparatus of FIG. 50; FIG. 54 is a block diagram showing a configuration of the rotating filters of FIG. 53; FIG. 55 is a diagram showing the spectral characteristics of a first filter group of the rotating filter of FIG. 54; FIG. 56 is a diagram showing the spectral characteristics of a second filter group of the rotating filter of FIG. 54; FIG. 57 is a diagram showing the layered structure of a living tissue observed via the endoscope apparatus of FIG. 53; FIG. 58 is a diagram illustrating the access state in the direction of the layers of a living tissue of illumination light from the endoscope apparatus of FIG. 53; FIG. 59 is a first diagram showing the respective band images resulting from the surface-sequential light permeating the first filter group of FIG. 55; FIG. 60 is a second diagram showing the respective band images resulting from the surface-sequential light permeating the first filter group of FIG. 55; FIG. 61 is a third diagram showing the respective band images resulting from the surface-sequential light permeating the first filter group of FIG. 55; FIG. 62 is a first diagram showing the respective band images resulting from the surface-sequential light permeating the second filter group of FIG. 56; FIG. 63 is a second diagram showing the respective band images resulting from the surface-sequential light permeating the second filter group of FIG. 56; FIG. 64 is a block diagram showing a configuration of the white balance circuit of FIG. 53; FIG. 65 is an external view showing the external configuration of a first variation of the endoscope apparatus of FIG. 50; FIG. 66 is an external view showing the external configuration of a second variation of the endoscope apparatus of FIG. 50; FIG. 67 is a block diagram showing a configuration of a synchronous-type endoscope apparatus, which is a variation of the endoscope apparatus of FIG. 53; and FIG. 68 is a block diagram showing a configuration of the white balance circuit of FIG. 67.

In ordinary-light observation, white balance is achieved in order to compensate for the irregularities of the various optical characteristics. In white balance, a correction value for multiplying a R signal and a B signal is obtained, and RGB signals output at white-light observation are made uniform. This makes it possible to suppress the affect of the above-mentioned irregularities on color reproducibility.

White balance must also be achieved prior to the start of an examination in narrowband-light observation (NBI observation) the same as in ordinary-light observation. This makes it possible to correct the irregularities of an optical filter for narrowband light, and stabilizes color reproducibility.

The illumination light in narrowband-light observation (NBI observation) used to be three-band R, G, B narrowband light, but the problem of changing to the two bands of G and B narrowband light in order to stabilize the reproducibility of mucous membrane information using narrowband light is that an R-light-based video signal cannot be achieved with a surface-sequential-type narrowband light, and therefore, since a G signal output is divided by an R signal output for a white balance correction value the same as with ordinary light, it becomes impossible to calculate the correction value for an R signal. Further, with synchronous-type narrowband light as well, it is impossible to employ the same correction value calculation method as with ordinary light because two signals are produced by converting from YCrCb, and the two signals do not include an R signal.

With the foregoing in view, it is an object of the present embodiment and a seventh embodiment, which will be explained hereinbelow, to provide an endoscope apparatus, which makes it possible to switch to white balance that corresponds to ordinary-light observation and narrowband-light observation.

As shown in FIG. 50, an endoscope apparatus 3001 of the present embodiment includes an electronic endoscope 3003 including a CCD 3002, which will be explained hereinbelow as image-capturing means, which is inserted into a body cavity, and which captures an image of body cavity tissue; a light-source apparatus 3004, which supplies illumination light to the electronic endoscope 3003; and a video processor 3007, which carries out signal processing of an image-capturing signal from the CCD 3002 of the electronic endoscope 3003, and displays an endoscopic image on an observation monitor 3005.

Front panels 3004a and 3007a are disposed on the front of the light-source apparatus 3004 and the video processor 3007, and, as shown in FIG. 51, a narrowband light observation mode display unit 3004b for notifying that the endoscope apparatus 3001 is in the narrowband-light observation mode is provided on the front panel 3004a of the light-source apparatus 3004. Further, a white balance switch 3007c, which indicates acquisition of white balance of an image-capturing signal from the CCD 3002, and a narrowband-light observation mode display unit 7300b for notifying that the endoscope apparatus 3001 is in the narrowband-light observation mode are provided on the front panel 3007a of the video processor 3007 as shown in FIG. 52.

In an endoscopic examination with the electronic endoscope 3003, which utilizes the light-source apparatus 3004 and video processor 3007, white balance must be achieved prior to examination, but in this case, white balance processing is performed by attaching a tubular white cap 3045, the inside of which has been made white, to the distal end of an insertion unit 3003a of the electronic endoscope 3003.

Meanwhile, when performing an examination using a special observation light, such as a narrowband light, white balance processing must be performed a total of two times, once each for an ordinary light and a special light.

However, since white balance processing is performed one time when conducting an ordinary endoscopic examination using ordinary light, there is the risk that the white cap 3045 may be removed from the end of the insertion unit 3003a of the electronic endoscope 3003 prior to the second white balance processing being completed, making it impossible to carry out the second white balance processing normally.

Accordingly, in the present embodiment, by notifying of the narrowband-light observation mode via the narrowband-light observation mode display units 3004b, 3007b provided on the front panels 3004a, 3007a, the fact that white balance processing of the narrowband light is in progress is visually recognizable from the narrowband-light observation mode display units 3004b, 3007b.

As shown in FIG. 53, the video processor 3007 is constituted so as to enable an endoscopic image to be encoded and outputted to an image filing apparatus 3006 as a compressed image.

The light-source apparatus 3004 includes a xenon lamp 3011 for emitting illumination light; a heat cutting filter 3012 for blocking the heat of a white light; a diaphragm device 3013 for controlling the quantity of light of a white light via the heat cutting filter 3012; a rotating filter 3014 for making the illumination light a surface-sequential light; a condensing lens 3016 for condensing the surface-sequential light via the rotating filter 3014 on the incident surface of a light guide 3015 arranged inside the electronic endoscope 3003; and a control circuit 3017 for controlling the rotation of the rotating filter 3014.

The rotating filter 3014, as shown in FIG. 54, is constituted in a disk shape, and has a dual structure centered around an axis of rotation, an R1 filter section 3014r1, a G1 filter section 3014g1, and a B1 filter section 3014b1, which constitute a first filter group for outputting surface-sequential light of overlapping spectral characteristics, which, as shown in FIG. 55, is well suited to color reproduction, are arranged in the outer radial part, and a G2 filter section 3014g2, a B2 filter section 3014b2, and a shading filter section 3014Cut, which constitute a second filter group for outputting narrowband surface-sequential light of discrete spectral characteristics, capable, as shown in FIG. 56, of extracting the desired layer tissue information, are arranged in the inner radial part.

Then, as shown in FIG. 53, the rotating filter 3014 is rotated in accordance with the control circuit 3017 driving and controlling a rotating filter motor 3018, and movement in the radial direction (movement, which is perpendicular to the optical path of the rotating filter 3014, and which selectively moves the first filter group and second filter group of the rotating filter 3014 in the optical path) is carried out by a mode switching motor 3019 in accordance with a control signal from a mode switching circuit 3042 inside the video processor 3007, which will be explained hereinbelow.

Furthermore, power is supplied from a power unit 3010 to the xenon lamp 3011, diaphragm device 3013, rotating filter motor 3018, and mode switching motor 3019.

The video processor 3007 includes a CCD drive circuit 3020 for driving the CCD 3002; an amplifier 3022 for amplifying an image-capturing signal, which is an image of a body cavity tissue captured by the CCD 3002 via an objective optical system 3021; a processing circuit 3023, which performs correlated double sampling and noise removal for an image-capturing signal through the amplifier 3022; an A/D converter 3024 for converting an image-capturing signal that has passed through the processing circuit 3023 to digital signal image data; a white balance circuit (W.B.) 3025 for performing white balance processing on the image data from the A/D converter 3024; a selector 3026 and synchronization memories 3027, 3028, 3029 for synchronizing surface-sequential light using the rotating filter 3014; an image processing circuit 3030 for reading out the respective image data of the surface-sequential light stored in the synchronization memories 3027, 3028, 3029, and performing gamma correction processing, contour highlight processing, and color processing; D/A circuits 3031, 3032, 3033 for converting image data from the image processing circuit 3030 to analog signals; an encoding circuit 3034 for encoding image data from the image processing circuit 3030; and a timing generator (T.G.) 3035 for inputting from the control circuit 3017 of the light-source apparatus 3004 a synchronization signal synchronized to the rotation of the rotating filter 3014, and outputting various timing signals to the above-described respective circuits.

Further, a mode-switching switch 3041 is provided in the electronic endoscope 3002, and the output of the mode-switching switch 3041 is outputted to a mode-switching circuit 3042 inside the video processor 3007. The mode-switching circuit 3042 of the video processor 3007 outputs control signals to the white balance circuit (W.B.) 3025, a light modulation circuit 3043, a light modulation control parameter switching circuit 3044, and the mode-switching motor 3019 of the light-source apparatus 3004. The light modulation control parameter switching circuit 3044 outputs a light modulation control parameter corresponding to the first filter group and the second filter group of the rotating filter 3014 to the light modulation circuit 3043, and the light modulation circuit 3043 performs proper brightness control by controlling the diaphragm device 3013 of the light-source apparatus 3004 based on the control signal from the mode-switching circuit 3042 and the light modulation control parameter from the light modulation control parameter switching circuit 3044.

As shown in FIG. 57, in most cases, for example, body cavity tissue 3051 has an absorbent distributed structure of blood vessels and the like that differ in the depth direction. In the vicinity of the superficial portion of the mucous membrane, mainly capillary vessels 3052 are distributed in large numbers, and in the intermediate layer, which is deeper than the superficial layer, blood vessels 3053 that are larger than capillary vessels are distributed in addition to capillary vessels, and in yet a deeper layer, even larger blood vessels 3054 are distributed.

Meanwhile, the invasion depth in the depth direction of light relative to a body cavity tissue 3051 is dependent on the wavelength of the light, and when illumination light including the visible region is a short wavelength like that of blue (B), as shown in FIG. 58, the light only penetrates as far as the vicinity of the superficial layer as a result of the absorption characteristics and scattering characteristics of the living tissue, is subjected to absorption and scattering in that depth range, and the light that exits from the surface is observed. Further, in the case of green (G) light, which has a longer wavelength than blue (B) light, the light penetrates deeper than the range to which the blue (B) light penetrates, is subjected to absorption and scattering in that range, and the light that exits from the surface is observed. And red (R) light, which has a longer wavelength than green (G) light, reaches an even deeper range.

At ordinary observation, the mode switching circuit 3042 inside the video processor 3007 controls the mode switching motor 3019 via a control signal such that the R1 filter 3014r1, G1 filter 3014g1, and B1 filter 3014b1, which are the first filter group of the rotating filter 3014, are located in the optical path of the illumination light.

As shown in FIG. 55, because the respective wavelength regions of the R1 filter 3014r1, G1 filter 3014g1, and B1 filter 3014b1 overlap one another at ordinary observation of a body cavity tissue 3051, (1) a band image including shallow layer and intermediate layer tissue information, which includes numerous tissue information of the shallow layer as shown in FIG. 59, is captured in an image-capturing signal, which is an image captured by the CCD 3004 via the B1 filter section 3014b1; (2) further, a band image including shallow layer and intermediate layer tissue information, which includes numerous tissue information of the intermediate layer as shown in FIG. 60, is captured in an image-capturing signal, which is an image captured by the CCD 3004 via the G1 filter section 3014g1; and (3) in addition, a band image including intermediate layer and deep layer tissue information, which includes numerous tissue information of the deep layer as shown in FIG. 61, is captured in an image-capturing signal, which is an image captured by the CCD 3004 via the R1 filter section 3014r1.

Then, an endoscopic image of a desired or natural color reproduction can be obtained as the endoscopic image by the video processor 3007 synchronizing the RGB image-capturing signals and performing signal processing.

Meanwhile, if the mode-switching switch 3041 of the electronic endoscope 3003 is pressed, the signal is inputted to the mode switching circuit 3042 of the video processor 3007. By outputting a control signal to the mode switching motor 3019 of the light-source apparatus 3004, the mode switching circuit 3042 drives the rotating filter 3014 relative to the optical path so as to move the first filter group of the rotating filter 3014, which was in the optical path at ordinary observation, and position the second filter group in the optical path.

As shown in FIG. 56, because the G2 filter section 3014g2, B2 filter section 3014b2, and shading filter section 3014Cut change the illumination light to narrowband surface-sequential light of discrete spectral characteristics, and their respective wavelength regions do not overlap when body cavity tissue 3051 is being observed under narrowband light using the second filter group, (4) a band image including tissue information of the shallow layer as shown in FIG. 62 is captured in an image-capturing signal, which is an image captured by the CCD 3004 via the B2 filter section 3014b2; and (5) a band image including tissue information of the intermediate layer as shown in FIG. 63 is captured in an image-capturing signal, which is an image captured by the CCD 3004 via the G2 filter section 3014g2.

Meanwhile, the white balance circuit 3025 includes a white balance correction unit 3080, and a white balance correction value calculation unit 3081, as shown in FIG. 64.

In the endoscope apparatus 3001 of the present embodiment, white balance is achieved prior to an examination by attaching a tubular white cap 3045, the inside of which has been made white, to the distal end of the insertion unit 3003a of the electronic endoscope 3003.

Specifically, when the white balance switch 3007C provided on the front panel 3007a of the video processor 3007 is pressed in a state in which the white cap 3045 is attached to the distal end of the insertion unit 3003a of the electronic endoscope 3003, the first filter group of the rotating filter 3014 in the light-source apparatus 3003 is positioned in the optical path, and white balance is achieved a first time for ordinary light by the white balance circuit 3025 of the video processor 3007. Then, once white balance has been achieved at ordinary light, the second filter group of the rotating filter 3014 in the light-source apparatus 3003 is positioned in the optical path, and white balance is achieved by the white balance circuit 3025 of the video processor 3007 a second time for narrowband light. While white balance is being achieved a first time and second time, the narrowband-light observation mode display unit 3004b provided on the front panel 3004a of the light-source apparatus 3003, and the narrowband-light observation mode display unit 3007b provided on the front panel 3007a of the video processor 3007 are lit up in a prescribed color.

Furthermore, the color that lights while white balance is being achieved the first time, and the color that lights while white balance is being achieved the second time can be different colors. For example, the color that lights while white balance is being achieved the first time can be green, and the color that lights while white balance is being achieved the second time can be white.

In the white balance circuit 3025, the white balance correction value calculation unit 3081 switches to the white balance correction value calculation method in accordance with a mode detection signal, which is a control signal from the mode-switching circuit 3042.

Specifically, the first-time white balance for ordinary light is:

(R correction value)=(G average value)/(R average value), (B correction value)=(G average value)/(B average value)

Second-time white balance for narrowband light is:

(R correction value)=(prescribed fixed value), (B correction value)=(G average value)/(B average value)

Then, the white balance correction unit 3080 outputs a correction value for each signal by multiplying by the corresponding input signal.

Thus, in the present embodiment, since the white balance method is switched for ordinary light and narrowband light, a state in which it is impossible to calculate the correction value of an R signal can be avoided even when there are two bands of illumination light resulting from narrowband light, making white balance achievable. Further, the fact that a white balance operation is being carried out can be clearly understood visually, and using different colors makes it possible to visually glean which white balance operation is current being carried out.

Furthermore, in the present embodiment, it is supposed that white balance processing is performed in accordance with lighting up the narrowband-light observation mode display units 3004b, 3007b but the present invention is not limited to this, and as shown in FIG. 65, speakers 3061 and 3062 can be provided inside the light-source apparatus 3003 and the video processor 3007 so as to notify of white balance processing by sound. In this case, notification can be provided using the same sound while white balance is achieved a first time and a second time, or the sound generated while achieving white balance the first time can differ from the sound generated while achieving white balance the second time. The fact that a white balance operation is being carried out can be recognized as a sound, and which white balance operation is currently being performed can be gleaned without looking at the apparatus.

Further, as shown in FIG. 66, the configuration can be such that a message window 3063 is displayed on the observation monitor 3005, and a message, such as, for example, "white balance in progress" is displayed in the message window 3063. Notification can be provided using the same message, for example, "white balance in progress", while white balance is achieved a first time and a second time, or the displayed message can be changed, such that the message displayed while achieving white balance the first time reads, for example, "white balance 1 in progress", and the message displayed while achieving white balance the second time reads, for example, "white balance 2 in progress". Furthermore, a message such as "white balance in progress" can be displayed during the achievement of white balance, and a message, such as "white balance not in progress" can be displayed when white balance is not being achieved. Displaying the fact that a white balance operation is being carried out on the observation monitor 3005 as character information further facilitates visual recognition.

Furthermore, in the endoscope apparatus 3001 of the above-described embodiments, the explanation used as an example a surface-sequential-type endoscope apparatus in which the light-source apparatus 3004 supplies surface-sequential light, and the video processor 3007 produces an image by synchronizing surface-sequential image information, however, the present invention is not limited to this, and a synchronous-type endoscope apparatus is also applicable.

That is, as shown in FIG. 67, a synchronous-type endoscope apparatus 3001, which comprises a light-source apparatus 4 for supplying white light, an electronic endoscope 3003 including a color chip 3100 on the front face of the image-capturing surface of the CCD 3002, and a video processor 3007, which performs signal processing for image-capturing signals from the electronic endoscope 3003 can also apply the present embodiment.

In the light-source apparatus 3004, white light from the xenon lamp 3011 passes through a heat cutting filter 3012, the quantity of light is controlled by the diaphragm device 3013, and the white light is outputted to the incident surface of the light guide 3015, which is arranged inside the electronic endoscope 3003. A narrowband interference filter 3014a, which converts the white light to narrowband light of discrete spectral characteristics as shown in FIG. 56, is removably provided in the optical path.

In the electronic endoscope 3003, an image of body cavity tissue 3051 is captured by the CCD 3002 through the color chip 3100.

In the video processor 3007, image data from the A/D converter 3024 is separated into a luminance signal Y and color difference signals Cr, Cb by the Y/C separation circuit 3101, converted to RGB signals by the RGB matrix circuit 3102, and outputted to the white balance circuit 3025. The remaining configuration and operations are the same as those of the endoscope apparatus of FIG. 53.

Then, in the white balance circuit 3025, as shown in FIG. 68, white balance is achieved for each signal of the RGB signals from the RGB matrix circuit 3102. The white balance acquisition method at this time is the same as for the present embodiment.

Seventh Embodiment

Figure 69:
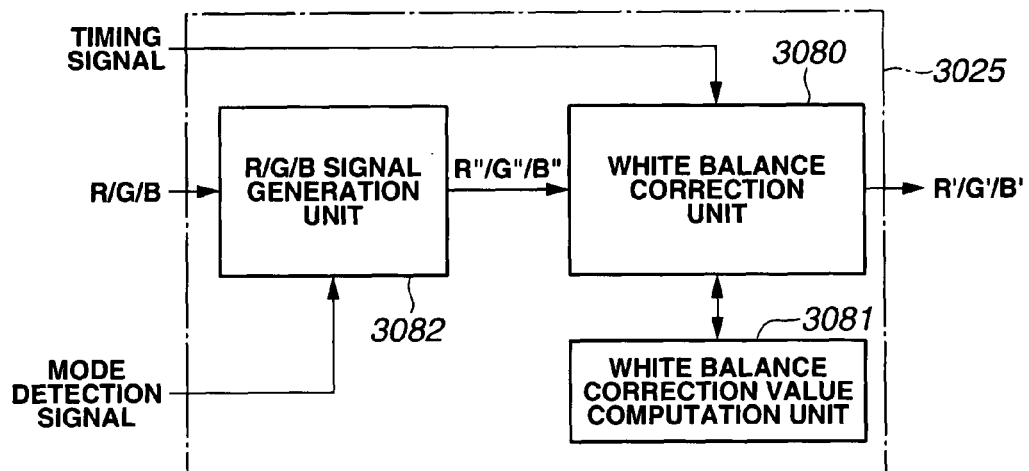
FIG. 69 is a block diagram showing a configuration of a white balance circuit related to a seventh embodiment of the present invention.

FIG. 69 is a block diagram showing a configuration of a white balance circuit related to a seventh embodiment of the present invention.

Since the seventh embodiment is practically the same as the sixth embodiment, only the points of difference will be explained, and an explanation of identical components having the same reference numerals will be omitted.

In the surface-sequential-type endoscope apparatus 3001 shown in FIG. 53, the white balance circuit 3025 of the present embodiment includes an R/G/B signal generation unit 3082 like the one shown in FIG. 69, and the R/G/B signal generation unit 3082, in response to the inputting of surface-sequential-type R/G/B signals, replaces the R signal in accordance with the observation mode, and thereafter, achieves white balance the same as the sixth embodiment.

That is, in the R/G/B signal generation unit 3082, replacement is performed as follows:
Ordinary light: R signal←R signal
Narrowband light: R signal←G signal
The post-replacement signal is outputted to the white balance correction unit 3080, and the white balance correction unit 3080 achieves white balance.

Furthermore, a B signal can be allocated to the R signal, and signal data prepared in advance can be used apart from the output of the CCD 3002.

Eighth Embodiment

Figure 70:
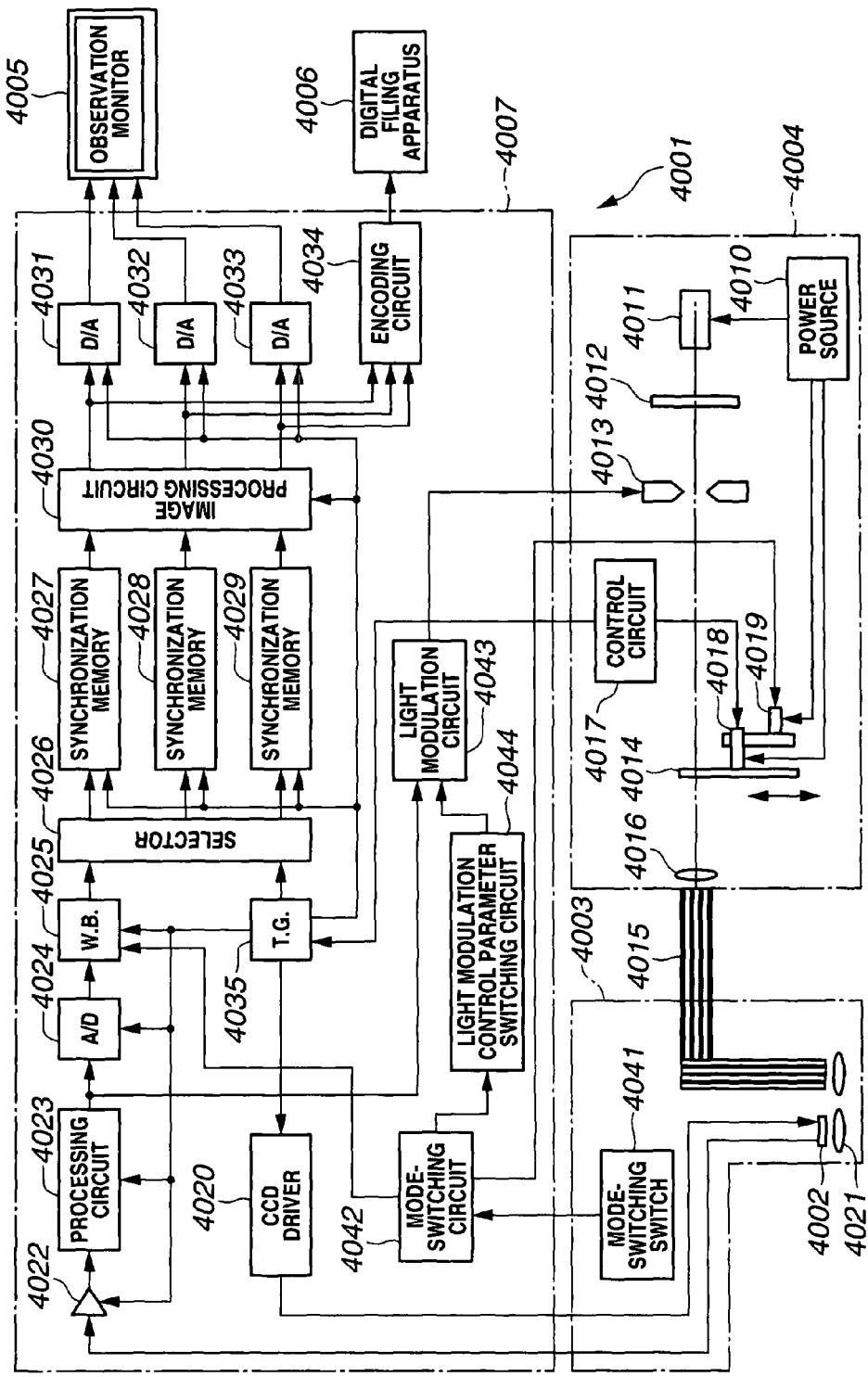
FIG. 70 is a block diagram showing a configuration of an endoscope apparatus related to an eighth embodiment of the present invention.
Figure 71:
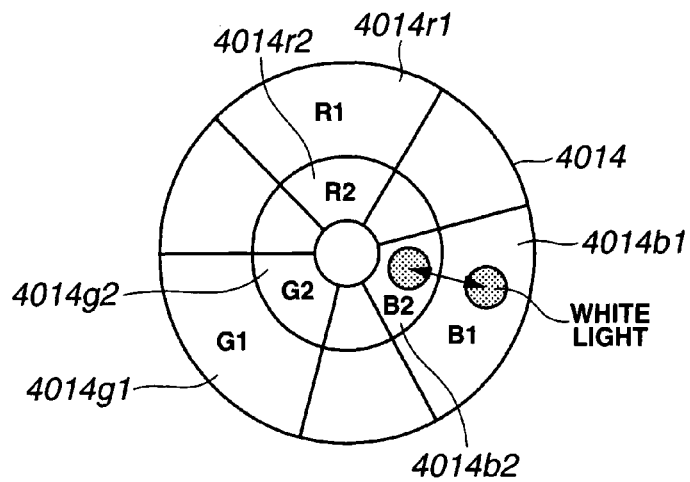
FIG. 71 is a block diagram showing a configuration of the rotating filter of FIG. 70.
Figure 72:
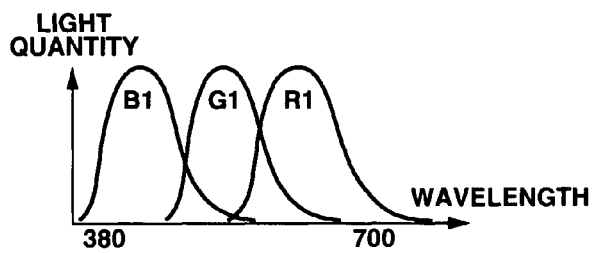
FIG. 72 is a diagram showing the spectral characteristics of a first filter group of the rotating filter of FIG. 71.
Figure 73:
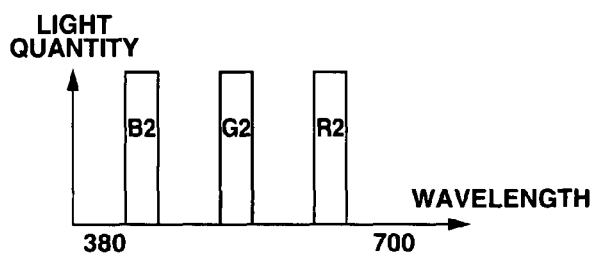
FIG. 73 is a diagram showing the spectral characteristics of a second filter group of the rotating filter of FIG. 71.
Figure 74:
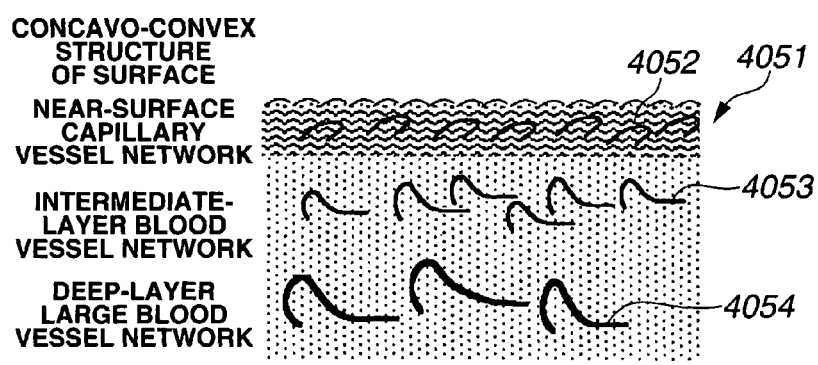
FIG. 74 is a diagram showing the layered structure of a living tissue observed via the endoscope apparatus of FIG. 70.
Figure 75:
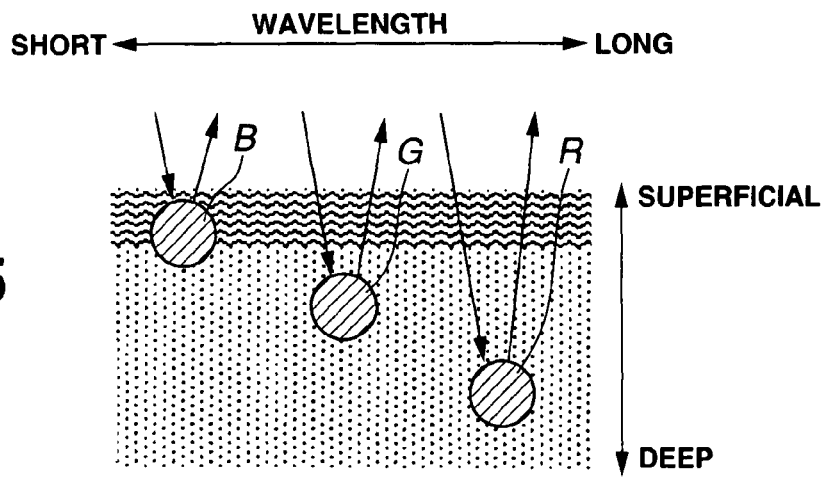
FIG. 75 is a diagram illustrating the access state in the direction of the layers of a living tissue of the illumination light from the endoscope apparatus of FIG. 70.
Figure 76:
FIG. 76 is a first diagram showing the respective band images resulting from the surface-sequential light permeating the first filter group of FIG. 72.
Figure 77:
FIG. 77 is a second diagram showing the respective band images resulting from the surface-sequential light permeating the first filter group of FIG. 72.
Figure 78:
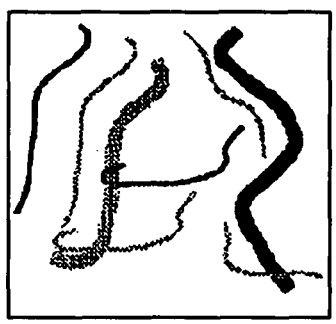
FIG. 78 is a third diagram showing the respective band images resulting from the surface-sequential light permeating the first filter group of FIG. 72.
Figure 79:
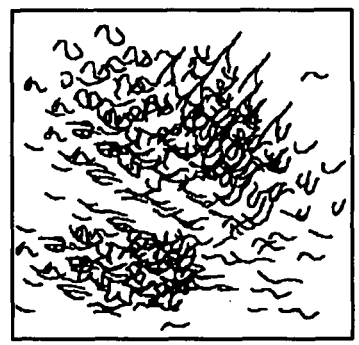
FIG. 79 is a first diagram showing the respective band images resulting from the surface-sequential light permeating the second filter group of FIG. 73.
Figure 80:
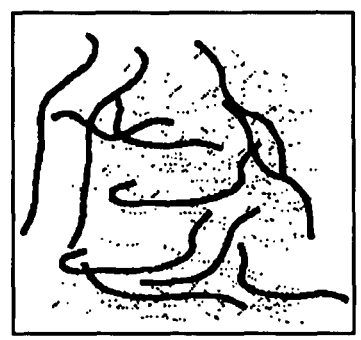
FIG. 80 is a second diagram showing the respective band images resulting from the surface-sequential light permeating the second filter group of FIG. 73.
Figure 81:
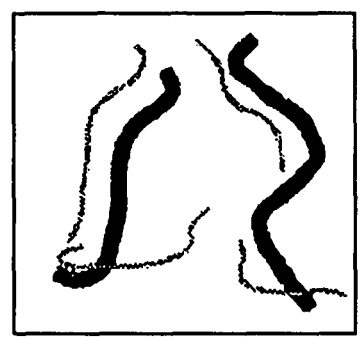
FIG. 81 is a third diagram showing the respective band images resulting from the surface-sequential light permeating the second filter group of FIG. 73.
Figure 82:
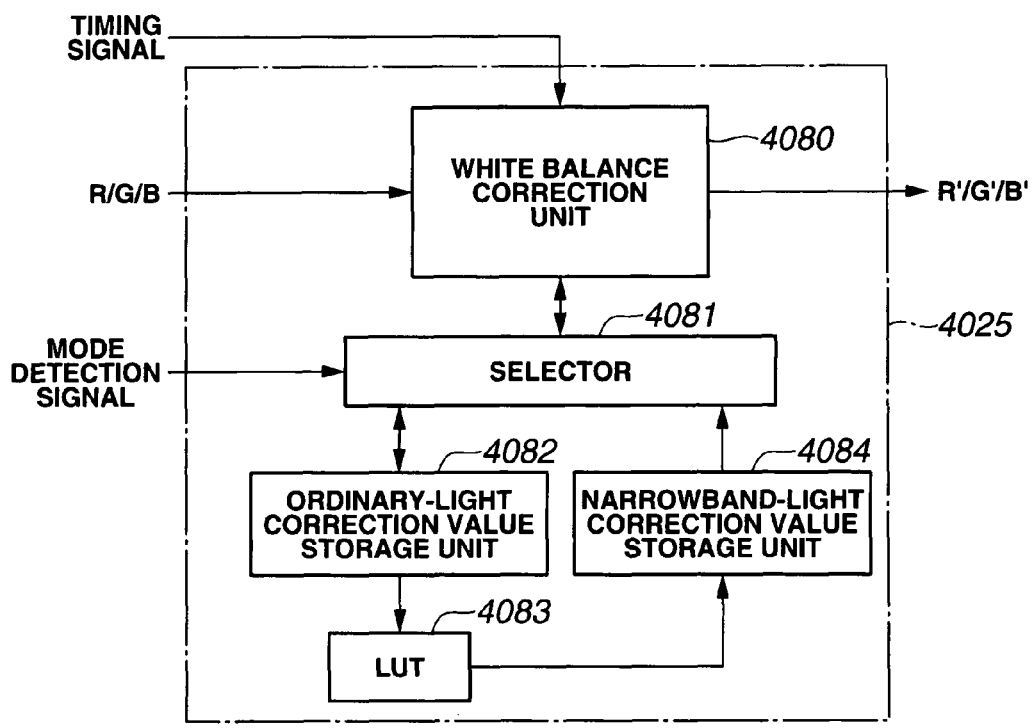
FIG. 82 is a block diagram showing a configuration of the white balance circuit of FIG. 70.
Figure 83:
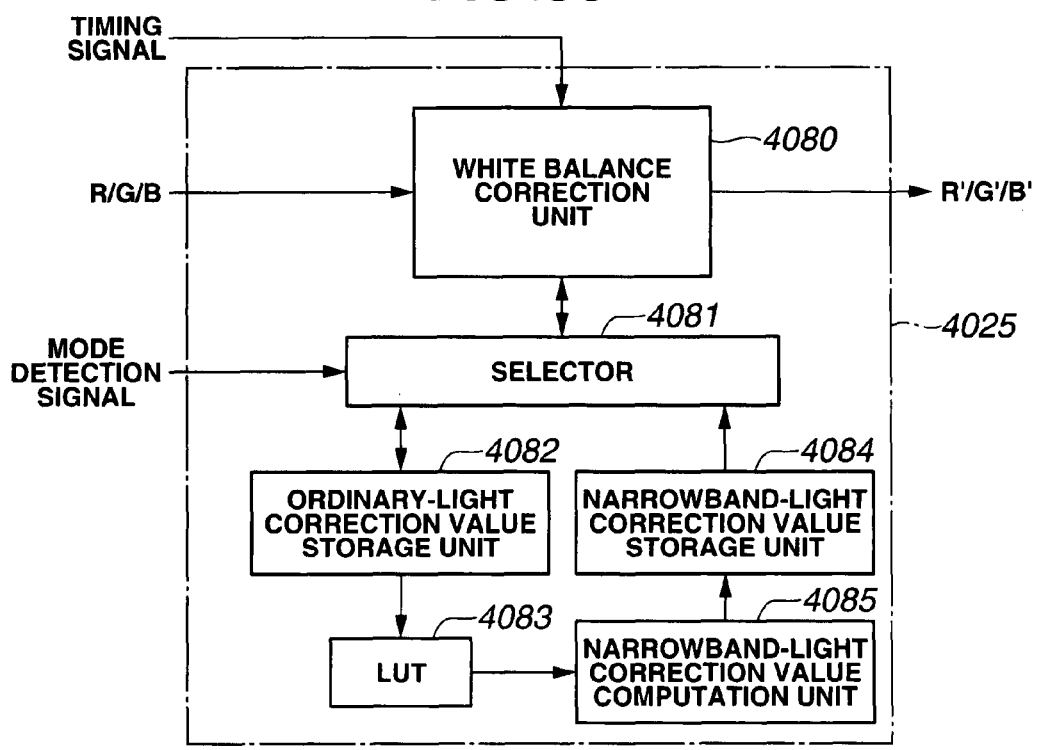
FIG. 83 is a block diagram showing a configuration of a variation of the white balance circuit of FIG. 82.
Figure 84:
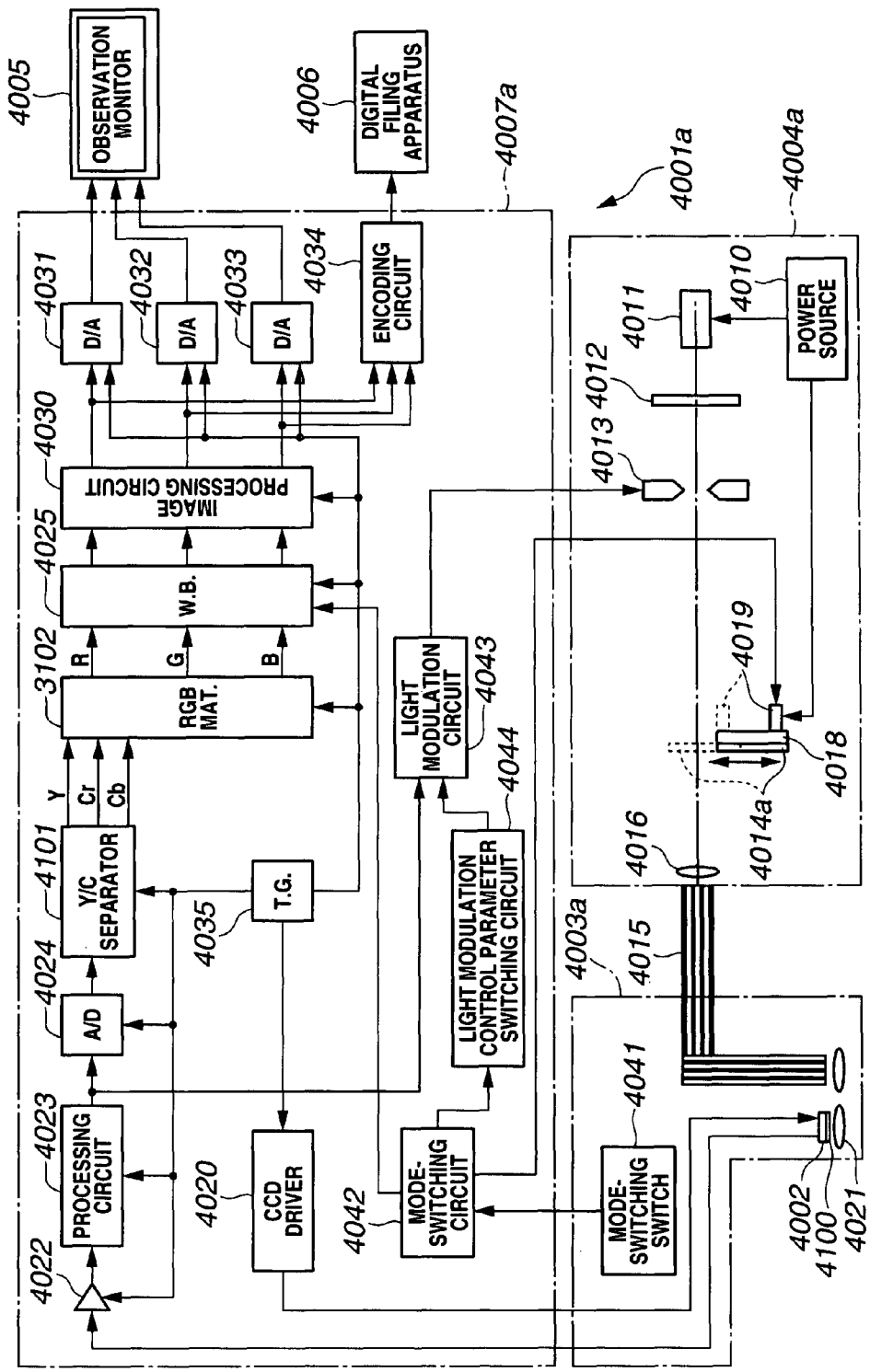
FIG. 84 is a block diagram showing a configuration of a first variation of the endoscope apparatus of FIG. 70.
Figure 85:
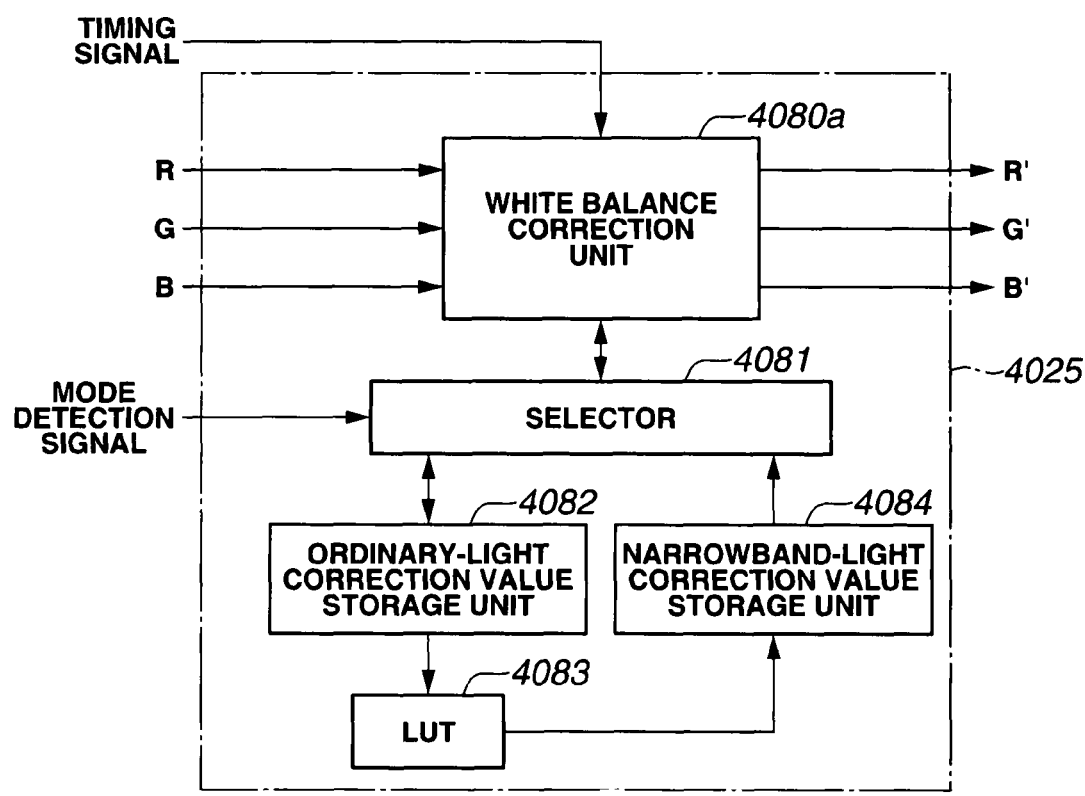
FIG. 85 is a block diagram showing a configuration of the white balance circuit of FIG. 84.
Figure 86:
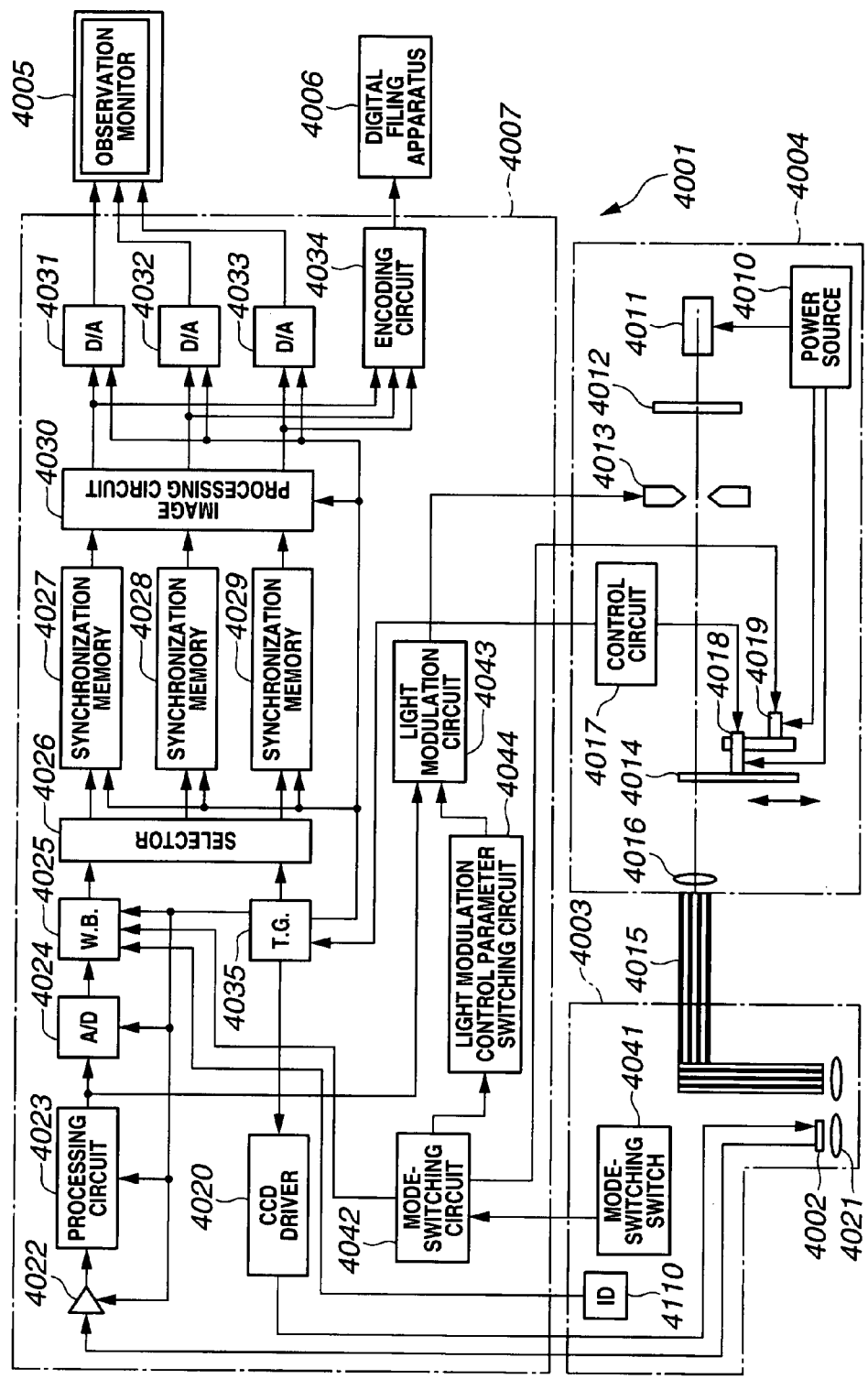
FIG. 86 is a block diagram showing a configuration of a second variation of the endoscope apparatus of FIG. 70.
Figure 87:
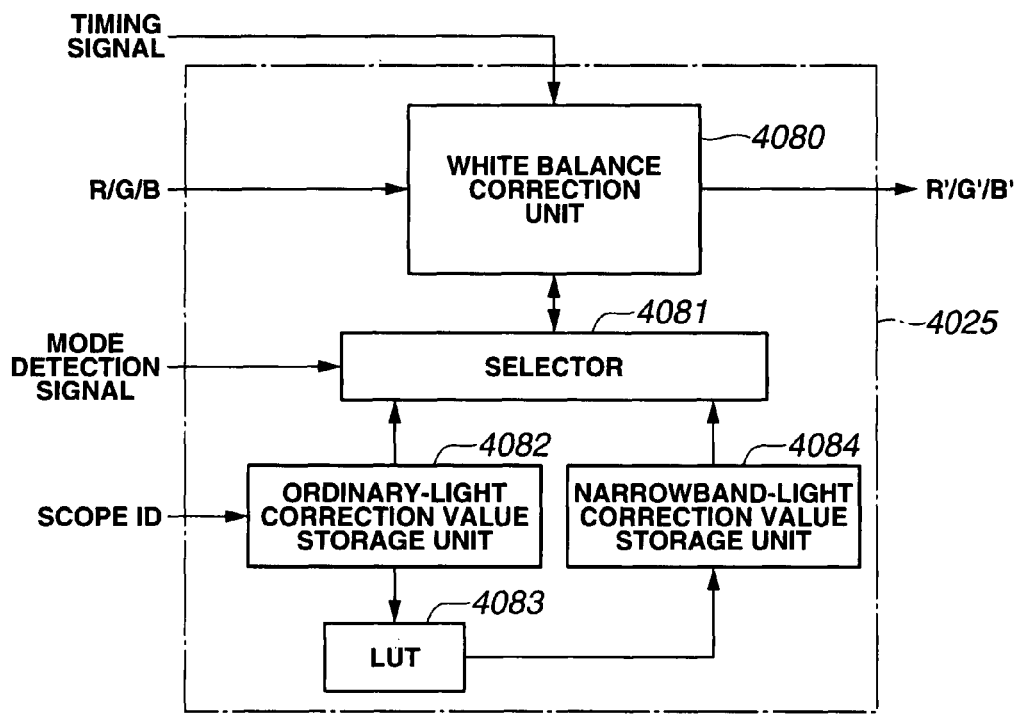
FIG. 87 is a block diagram showing a configuration of the white balance circuit of FIG. 86.
Figure 88:
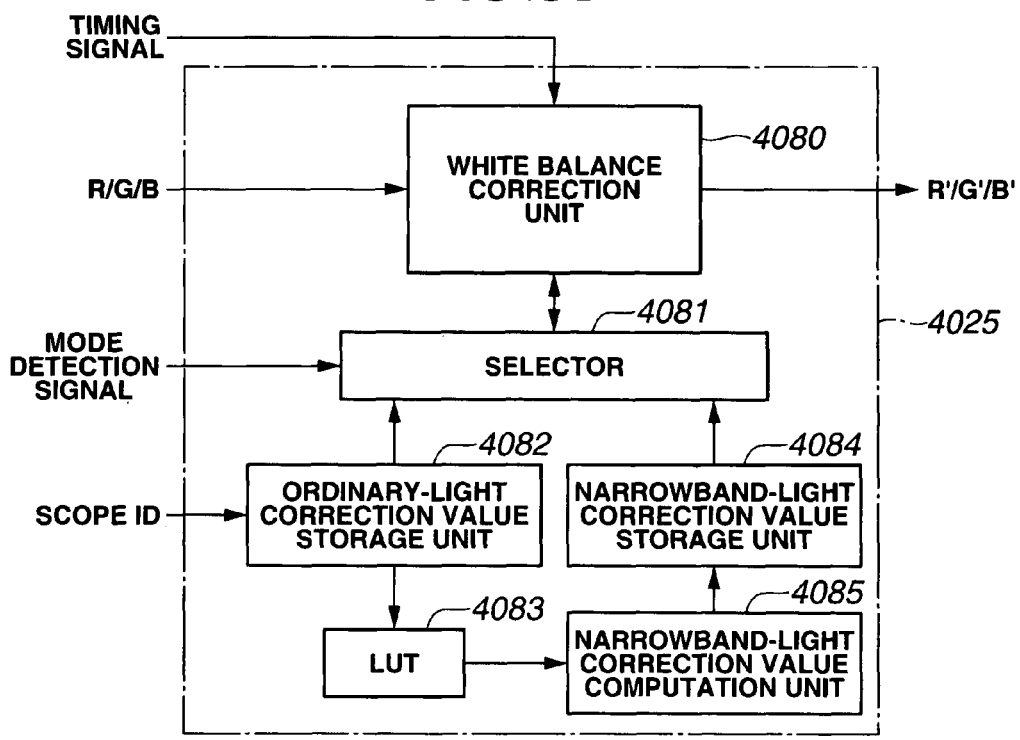
FIG. 88 is a block diagram showing a configuration of a variation of the white balance circuit of FIG. 86.

FIGS. 70 through 88 are related to an eighth embodiment of the present invention. FIG. 70 is a block diagram showing a configuration of an endoscope apparatus; FIG. 71 is a configuration diagram showing a configuration of the rotating filter of FIG. 70; FIG. 72 is a diagram showing the spectral characteristics of a first filter group of the rotating filter of FIG. 71; FIG. 73 is a diagram showing the spectral characteristics of a second filter group of the rotating filter of FIG. 71; FIG. 74 is a diagram showing the layered structure of a living tissue observed via the endoscope apparatus of FIG. 70; FIG. 75 is a diagram illustrating the access state in the direction of the layers of a living tissue of the illumination light from the endoscope apparatus of FIG. 70; FIG. 76 is a first diagram showing the respective band images resulting from the surface-sequential light permeating the first filter group of FIG. 72; FIG. 77 is a second diagram showing the respective band images resulting from the surface-sequential light permeating the first filter group of FIG. 72; FIG. 78 is a third diagram showing the respective band images resulting from the surface-sequential light permeating the first filter group of FIG. 72; FIG. 79 is a first diagram showing the respective band images resulting from the surface-sequential light permeating the second filter group of FIG. 73; FIG. 80 is a second diagram showing the respective band images resulting from the surface-sequential light permeating the second filter group of FIG. 73; FIG. 81 is a third diagram showing the respective band images resulting from the surface-sequential light permeating the second filter group of FIG. 73; FIG. 82 is a block diagram showing a configuration of the white balance circuit of FIG. 70; FIG. 83 is a block diagram showing a configuration of a variation of the white balance circuit of FIG. 82; FIG. 84 is a block diagram showing a configuration of a first variation of the endoscope apparatus of FIG. 70; FIG. 85 is a block diagram showing a configuration of the white balance circuit of FIG. 84; FIG. 86 is a block diagram showing a configuration of a second variation of the endoscope apparatus of FIG. 70; FIG. 87 is a block diagram showing a configuration of the white balance circuit of FIG. 86; and FIG. 88 is a block diagram showing a configuration of a variation of the white balance circuit of FIG. 86.

As shown in FIG. 70, an endoscope apparatus 4001 of the present embodiment includes an electronic endoscope 4003 including a CCD 4002 as image-capturing means, which is inserted into a body cavity, and which captures an image of the body cavity tissue; a light-source apparatus 4004, which supplies illumination light to the electronic endoscope 4003; and a video processor 4007, which performs signal processing of an image-capturing signal from the CCD 4002 of the electronic endoscope 4003, and displays an endoscopic image on an observation monitor 4005, and also encodes the endoscopic image and outputs as a compressed image to an image filing apparatus 4006.

The light-source apparatus 4004 includes a xenon lamp 4011 for emitting illumination light; a heat cutting filter 4012 for blocking the heat of a white light; a diaphragm device 4013 for controlling the quantity of light of a white light via the heat cutting filter 4012; a rotating filter 4014 for making an illumination light into a surface-sequential light; a condensing lens 4016 for condensing the surface-sequential light via the rotating filter 4014 on the incident surface of a light guide 4015 arranged inside the electronic endoscope 4003; and a control circuit 4017 for controlling the rotation of the rotating filter 4014.

The rotating filter 4014, as shown in FIG. 71, is constituted in a disk shape, and has a dual structure centered around an axis of rotation, an R1 filter section 4014*r*1, a G1 filter section 4014*g*1, and a B1 filter section 4014*b*1, which constitute a first filter group for outputting surface-sequential light of overlapping spectral characteristics, which, as shown in FIG. 72, is well suited to color reproduction, are arranged in the outer radial part, and a G2 filter section 4014*g*2, a B2 filter section 4014*b*2, and a R2 filter section 4014*r*2, which constitute a second filter group for outputting narrowband surface-sequential light of discrete spectral characteristics, capable, as shown in FIG. 73, of extracting the desired depth layer tissue information, are arranged in the inner radial part.

Then, as shown in FIG. 70, the rotating filter 4014 is rotated in accordance with the control circuit 4017 driving and controlling a rotating filter motor 4018, and movement in the radial direction (movement, which is perpendicular to the optical path of the rotating filter 4014, and which selectively moves the first filter group and second filter group of the rotating filter 4014 in the optical path) is carried out by a mode switching motor 4019 in accordance with a control signal from a mode switching circuit 4042 inside the video processor 4007, which will be explained hereinbelow.

Furthermore, power is supplied from a power unit 4010 to the xenon lamp 4011, diaphragm device 4013, rotating filter motor 4018, and mode switching motor 4019.

The video processor 4007 includes a CCD drive circuit 4020 for driving the CCD 4002; an amplifier 4022 for amplifying an image-capturing signal, which is an image of a body cavity tissue captured by the CCD 4002 via an objective optical system 4021; a processing circuit 4023, which performs correlated double sampling and noise removal for an image-capturing signal through the amplifier 4022; an A/D converter 4024 for converting an image-capturing signal that has passed through the processing circuit 4023 to digital signal image data; a white balance circuit (W.B.) 4025 for performing white balance processing on the image data from the A/D converter 4024; a selector 4026 and synchronization memories 4027, 4028, 4029 for synchronizing surface-sequential light via the rotating filter 4014; an image processing circuit 4030 for reading out the respective image data of the surface-sequential light stored in the synchronization memories 4027, 4028, 4029, and performing gamma correction processing, contour highlight processing, and color processing; D/A circuits 4031, 4032, 4033 for converting image data from the image processing circuit 4030 to analog signals; an encoding circuit 4034 for encoding image data from the image processing circuit 4030; and a timing generator (T.G.) 4035 for inputting from the control circuit 4017 of the light-source apparatus 4004 a synchronization signal synchronized to the rotation of the rotating filter 4014, and outputting various timing signals to the above-described respective circuits.

Further, a mode-switching switch 4041 is provided to the electronic endoscope 4002, and the output of the mode-switching switch 4041 is outputted to a mode-switching circuit 4042 inside the video processor 4007. The mode-switching circuit 4042 of the video processor 4007 outputs control signals to the white balance circuit (W.B.) 4025, a light modulation circuit 4043, a light modulation control parameter switching circuit 4044, and the mode-switching motor 4019 of the light-source apparatus 4004. The light modulation control parameter switching circuit 4044 outputs a light modulation control parameter corresponding to the first filter group and the second filter group of the rotating filter 4014 to the light modulation circuit 4043, and the light modulation circuit 4043 performs proper brightness control by controlling the diaphragm device 4013 of the light-source apparatus 4004 based on the control signal from the mode-switching circuit 4042 and the light modulation control parameter from the light modulation control parameter switching circuit 4044.

As shown in FIG. 74, in most cases, for example, body cavity tissue 4051 has an absorbent distributed structure of blood vessels and the like that differ in the depth direction. In the vicinity of the superficial portion of the mucous membrane, mainly capillary vessels 4052 are distributed in large numbers, and in the intermediate layer, which is deeper than the superficial layer, blood vessels 4053 that are larger than capillary vessels are distributed in addition to capillary vessels, and in yet a deeper layer, even larger blood vessels 4054 are distributed.

Meanwhile, the invasion depth in the depth direction of light relative to a body cavity tissue 4051 is dependent on the wavelength of the light, and when illumination light including the visible region is a short wavelength like that of blue (B), as shown in FIG. 75, the light only penetrates as far as the vicinity of the superficial layer as a result of the absorption characteristics and scattering characteristics of the living tissue, is subjected to absorption and scattering in that depth range, and the light that exits from the surface is observed. Further, in the case of green (G) light, which has a longer wavelength than blue (B) light, the light penetrates deeper than the range to which the blue (B) light penetrated, is subjected to absorption and scattering in that range, and the light that exits from the surface is observed. Furthermore, red (R) light, which has a longer wavelength than green (G) light, reaches an even deeper range.

At ordinary observation, the mode switching circuit 4042 inside the video processor 4007 controls the mode switching motor 4019 via a control signal such that the R1 filter 4014$r1$, G1 filter 4014$g1$, and B1 filter 4014$b1$, which are the first filter group of the rotating filter 4014, are located in the optical path of the illumination light.

As shown in FIG. 72, because the respective wavelength regions of the R1 filter 4014$r1$, G1 filter 4014$g1$, and B1 filter 4014$b1$ overlap one another at ordinary observation of a body cavity tissue 4051, (1) a band image including shallow layer and intermediate layer tissue information, which includes numerous tissue information of the shallow layer as shown in FIG. 76, is captured in an image-capturing signal, which is an image captured by the CCD 4004 via the B1 filter section 4014$b1$; (2) further, a band image including shallow layer and intermediate layer tissue information, which includes numerous tissue information of the intermediate layer as shown in FIG. 77, is captured in an image-capturing signal, which is an image captured by the CCD 4004 via the G1 filter section 4014$g1$; and (3) in addition, a band image including intermediate layer and deep layer tissue information, which includes numerous tissue information of the deep layer as shown in FIG. 78, is captured in an image-capturing signal, which is an image captured by the CCD 4004 via the R1 filter section 4014$r1$.

Then, an endoscopic image of a desired or natural color reproduction can be obtained as the endoscopic image by the video processor 4007 synchronizing the RGB image-capturing signals and performing signal processing.

Meanwhile, when the mode-switching switch 4041 of the electronic endoscope 4003 is pressed, the signal is inputted to the mode switching circuit 4042 of the video processor 4007. By outputting a control signal to the mode switching motor 4019 of the light-source apparatus 4004, the mode switching circuit 4042 drives the rotating filter 4014 relative to the optical path so as to move the first filter group of the rotating filter 4014, which was in the optical path during ordinary observation, and position the second filter group in the optical path.

As shown in FIG. 73, because the G2 filter section 4014$g2$, B2 filter section 4014$b2$, and R2 filter section 4014$r2$ change the illumination light to narrowband surface-sequential light of discrete spectral characteristics, and their respective wavelength regions do not overlap when body cavity tissue 4051 is being observed under narrowband light using the second filter group, (4) a band image including tissue information of the shallow layer as shown in FIG. 79 is captured in an image-capturing signal, which is an image captured by the CCD 4004 via the B2 filter section 4014$b2$; (5) a band image including tissue information of the intermediate layer as shown in FIG. 80 is captured in an image-capturing signal, which is an image captured by the CCD 4004 via the G2 filter section 4014$g2$, and (6) furthermore, a band image including tissue information of the deep layer as shown in FIG. 81 is captured in an image-capturing signal, which is an image captured by the CCD 4004 via the R2 filter section 4014$r2$.

The white balance circuit 4025 includes a white balance correction unit 4080, selector 4081, ordinary-light correction value storage unit 4082, look-up table (LUT) 4083, and narrowband-light correction value storage unit 4084, as shown in FIG. 82.

White balance at ordinary light is achieved prior to an examination using the endoscope apparatus 4001 by attaching a white cap (not shown in the figure) to the distal end of the electronic endoscope 4003.

In the white balance circuit 4025, ordinary surface-sequential R/G/B signals, which are image data from the A/D converter 4024 when the white cap is attached, are inputted to the white balance correction unit 4080, white balancing is performed for the ordinary surface-sequential R/G/B signals, and white-balance ordinary-light correction values are stored in the ordinary-light correction value storage unit 4082 by way of the selector 4081, and, in addition, white-balanced R'/G'/B' signals are outputted to the selector 4026.

A narrowband-light correction value, which is based on the ordinary-light correction value, is then read out from the LUT 4083, and stored in the narrowband-light correction value storage unit 4084 in the white balance circuit 4025.

Specifically, in the white balance correction unit 4080, correction values for R and B are calculated from the ratios G/R and G/B of the average values of the ordinary surface-sequential R/G/B signals, and if the observation mode detected by the mode-switching circuit 4042 is the ordinary-light mode, an ordinary-light correction value is stored in the ordinary-light correction value storage unit 4082, and if the observation mode detected by the mode-switching circuit 4042 is the narrowband-light mode, a narrowband-light correction value is determined from the ordinary-light correction value and LUT 4083, and stored in the narrowband-light correction value storage unit 4084. A correction value is sent to the white balance correction unit 4080 from either the ordinary-light correction value storage unit 4082 or the narrowband-light correction value storage unit 4084 in accordance with the observation mode detected by the selector 4081, the correction values are multiplied by the white balance correction unit 4080, and R' and B" signals are outputted. The G signal is outputted as-is at this time.

Furthermore, the LUT 4083 stores a narrowband-light correction value based on an ordinary-light correction value, but the present invention is not limited to this. As shown in FIG. 83, the configuration can also be such that a correction value coefficient k based on an ordinary-light correction value is stored in the LUT 4083, a narrowband-light correction value is computed by a narrowband-light correction value computation unit 4085 using the equation:

narrowband-light correction value=$k$×ordinary-light correction value and stored in the narrowband-light correction value storage unit 4084. Furthermore, k is a constant.

Thus, in the present embodiment, since correction is performed by calculating a narrowband-light correction value from the correction value for an ordinary light, the narrowband light does not need to undergo white balancing, making it possible to simplify operation, and to reliably avoid poor color reproduction due to an operational error.

Furthermore, in the endoscope apparatus 4001 of the above-described embodiment, the explanation gives as an example a surface-sequential-type endoscope apparatus in which the light-source apparatus 4004 supplies surface-sequential light, and the video processor 4007 synchronizes surface-sequential image information to create an image, but the present invention is not limited to this, and is also applicable to a synchronous-type endoscope apparatus.

That is, as shown in FIG. 84, a synchronous-type endoscope apparatus 4001a, which includes a light-source apparatus 4004a for supplying white light; an electronic endoscope 4003a including a color chip 4100 on the front face of the image-capturing surface of the CCD 4002; and a video processor 4007a, which performs signal processing of an image-capturing signal from the electronic endoscope 4003a, can also apply the present embodiment.

In the light-source apparatus 4004a, white light from the xenon lamp 4011 passes through the heat cutting filter 4012, the quantity of light is controlled by the diaphragm device 4013, and the white light is outputted to the incident surface of the light guide 4015, which is arranged inside the electronic endoscope 4003a. A narrowband interference filter 4014a, which converts the white light to narrowband light of discrete spectral characteristics as shown in FIG. 73, is removably provided in the optical path.

In the electronic endoscope 4003a, an image of body cavity tissue 4051 is captured by the CCD 4002 through the color chip 4100.

In the video processor 4007a, image data from the A/D converter 4024 is separated into a luminance signal Y and color difference signals Cr, Cb by the Y/C separation circuit 4101, converted to RGB signals by the RGB matrix circuit 4102, and outputted to the white balance circuit 4025. The remaining configuration and operations are the same as the endoscope apparatus of FIG. 70.

Then, in the white balance circuit 4025, as shown in FIG. 85, white balance is achieved for each signal of the RGB signals from the RGB matrix circuit 4102. The white balance acquisition method at this time is the same as for the present embodiment.

Further, as shown in FIG. 86, the configuration is such that a scope ID storage unit 4110, which stores a scope ID including various scope information to include an ordinary-light correction value, is provided in the electronic endoscope 4003, and by outputting the ordinary-light correction value in the scope ID to the white balance circuit 4025, as shown in FIG. 87, the ordinary light correction storage unit 4082 in the white balance circuit 4025 reads out a narrowband-light correction value from the LUT 4083 using the ordinary-light correction value, and stores the value in the narrowband-light correction value computation unit 4085.

Furthermore, as shown in FIG. 88, a correction coefficient k, which is based on the ordinary-light correction value in the scope ID outputted to the white balance circuit 4025, can be stored in the LUT 4083, a narrowband-light correction value can be computed by the narrowband-light correction value computation unit 4085 using he above-mentioned equation:

narrowband-light correction value=$k$×ordinary-light correction value and the narrowband-light correction value may be stored in the narrowband-light correction value storage unit 4084. Furthermore, k is a constant.

Furthermore, in the endoscope of FIG. 86, the explanation gives as an example a surface-sequential-type endoscope, but the present invention is not limited to this, and a synchronous type is also applicable.

The present invention is not restricted to the embodiments described hereinabove, and various modifications and changes are possible within a scope that does not alter the gist of the present invention.

What is claimed is:

1. An endoscope apparatus, comprising:
    an illumination light supplying unit for supplying illumination light;
    an endoscope including an image-capturing unit for irradiating the illumination light onto an object, and capturing an image of the object by returning light;
    a two-band restricting unit for restricting the illumination light to a narrowband light of two non-overlapping band regions, and irradiating the narrowband light onto the object; and
    a signal processing unit for generating a first band region image data and a second band region image data in accordance with the narrowband light of two band regions, which is restricted and irradiated by the two-band restricting unit, and for generating, from the first band region image data and the second band region image data, three-channel color image data which is displayed on a displaying unit.

2. The endoscope apparatus according to claim 1, wherein at least one of the narrowband light via the two-band restricting unit is visible light.

3. The endoscope apparatus according to claim 1, wherein the two-band restricting unit restricts the illumination light to narrowband light of two non-overlapping band regions, which are a green wavelength band and a blue wavelength band.

4. The endoscope apparatus according to claim 3, wherein the two-band restricting unit restricts the illumination light to narrowband light of two non-overlapping band regions, in which the spectral product of the narrowband light of the green wavelength band is suppressed to be smaller than the spectral product of the narrowband light of the blue wavelength band.

5. The endoscope apparatus according to claim 4, wherein the two-band restricting unit chronologically irradiates narrowband light of the two non-overlapping band regions onto the object.

6. The endoscope apparatus according to claim 4, wherein the image-capturing unit comprises a wavelength band separating unit on the image-capturing surface.

7. The endoscope apparatus according to claim 1, wherein the two-band restricting unit restricts the illumination light to narrowband light of two non-overlapping band regions within the green wavelength band.

8. The endoscope apparatus according to claim 1, wherein the two-band restricting unit restricts the illumination light to narrowband light of two non-overlapping band regions within the blue wavelength band.

9. The endoscope apparatus according to claim 1, wherein the two-band restricting unit chronologically irradiates narrowband light of the two non-overlapping band regions onto the object.

10. The endoscope apparatus according to claim 1, wherein the image-capturing unit includes a wavelength band separating unit on the image-capturing surface.

11. The endoscope apparatus according to claim 1, wherein a ratio of color signal components, which are images captured via at least a plurality of wavelength bands, is changed at ordinary-light observation via a broadband illumination light and at narrowband-light observation via a narrowband illumination light, and a light modulation reference signal which adjusts the quantity of light of the illumination light is generated.

12. The endoscope apparatus according to claim 11, wherein the broadband illumination light and the narrowband illumination light are synchronous-type illumination lights which simultaneously illuminate illumination light of respective pluralities of wavelength bands, and the light modulation reference signal is generated at narrowband-light observation such that a ratio of color signals captured on the short wavelength side is greater than a ratio of color signals captured on the long wavelength side.

13. The endoscope apparatus according to claim 11, wherein the broadband illumination light and the narrowband illumination light are surface-sequential-type illumination lights which sequentially illuminate illumination light of respective pluralities of wavelength bands, and the light modulation reference signal is generated at narrowband-light observation such that a ratio of color signals captured on the short wavelength side is greater than a ratio of color signals captured on the long wavelength side.

14. The endoscope apparatus according to claim 11, wherein a value, which constitutes a target when adjusting the quantity of light of the illumination light using the light modulation reference signal, is switched at the ordinary-light observation and at the narrowband-light observation.

15. The endoscope apparatus according to claim 11, wherein the light modulation reference signal is generated at narrowband-light observation using G and B color signals which correspond to green (G) and blue (B) wavelength bands.

16. The endoscope apparatus according to claim 11, wherein the light modulation reference signal is generated using a gain control amplifier.

17. The endoscope apparatus according to claim 11, wherein the light modulation reference signal is generated using a plurality of multipliers.

18. The endoscope apparatus according to claim 1, comprising:
a color separating unit for separating output signals from the image-capturing unit into a luminance signal and a color difference signal; and
a processing characteristic changing unit for changing a processing characteristic relative to a signal which has undergone color separation by the color separating unit in accordance with switching in signal processing to the narrowband light from the illumination light.

19. The endoscope apparatus according to claim 18, comprising a band restricting unit for carrying out band restriction for the color difference signal separated by the color separating unit, wherein when switching is carried out from illumination light of the visible region to illumination light of a narrowband, the processing characteristic changing unit changes a characteristic of a pass band by the band restricting unit to broadband.

20. The endoscope apparatus according to claim 18, comprising a converting unit for converting from the luminance signal and color difference signal separated by the color separating unit to three primary color signals, wherein when switching is carried out from illumination light of the visible region to illumination light of a narrowband, the processing characteristic changing unit changes a conversion coefficient which determines a conversion characteristic by the converting unit.

21. The endoscope apparatus according to claim 20, wherein the converting unit converts the luminance signal and color difference signal to three primary color signals which have practically no mixed colors.

22. The endoscope apparatus according to claim 20, further comprising a second converting unit for converting the three primary color signals to a luminance signal and a color difference signal, wherein when switching from illumination light of the visible region to narrowband illumination light, the second converting unit changes conversion characteristics so as to increase the weighting of a short wavelength color signal in the three primary color signals.

23. The endoscope apparatus according to claim 18, further comprising a modulated-light signal generating unit for controlling the quantity of light of illumination light, and a gain controlling unit for variably controlling the level of the video signal, wherein the operation of the modulated-light signal generating unit is given priority over the operation of the gain controlling unit.

24. The endoscope apparatus according to claim 18, comprising a converting unit for converting the luminance signal and color difference signal separated by the color separating unit to a second luminance signal and a second color difference signal, wherein when switching from illumination light of the visible region to narrowband illumination light, the converting unit changes conversion characteristics so as to increase the weighting of a short wavelength color signal.

25. The endoscope apparatus according to claim 18, wherein when switching from illumination light of the visible region to narrowband illumination light, a γ characteristic is changed.

26. The endoscope apparatus according to claim 18, wherein when switching from illumination light of the visible region to narrowband illumination light, a highlighting unit changes a highlighting characteristic.

27. An endoscope apparatus which comprises:
an illumination light supplying unit for supplying illumination light;
an endoscope including an image-capturing unit for irradiating the illumination light onto an object, and capturing an image of the object by returning light; and
a signal processing unit for performing signal processing on an image-capturing signal from the image-capturing unit; wherein the endoscope apparatus further comprising: a two-band restricting unit for restricting the illumination light to narrowband light of two non-overlapping band regions, and irradiating the narrowband light onto the object; and a multi-band filter including at least two of: (i) a red element; (ii) a green element; and (iii) a blue element, the multi-band filter being configured to filter the illumination light into light of at least two overlapping band regions; wherein the illumination light is controlled by a selected one of the two-band restricting unit and the multi-band filter.

28. The endoscope apparatus according to claim 27, wherein the two-band restricting unit restricts the illumination light to narrowband light of two non-overlapping band regions, which are a green wavelength band and a blue wavelength band.

29. The endoscope apparatus according to claim 28, wherein the two-band restricting unit restricts the illumination light to narrowband light of two non-overlapping band regions, in which the spectral product of the narrowband light of the green wavelength band is suppressed to be smaller than the spectral product of the narrowband light of the blue wavelength band.

30. The endoscope apparatus according to claim 29, wherein the two-band restricting unit chronologically irradiates narrowband light of the two non-overlapping band regions onto the object.

31. The endoscope apparatus according to claim 29, wherein the image-capturing unit comprises a wavelength band separating unit on the image-capturing surface.

32. The endoscope apparatus according to claim 27, wherein the two-band restricting unit restricts the illumination light to narrowband light of two non-overlapping band regions within the green wavelength band.

33. The endoscope apparatus according to claim 27, wherein the two-band restricting unit restricts the illumination light to narrowband light of two non-overlapping band regions within the blue wavelength band.

34. The endoscope apparatus according to claim 27, wherein the two-band restricting unit chronologically irradiates narrowband light of the two non-overlapping band regions onto the object.

35. The endoscope apparatus according to claim 27, wherein the image-capturing unit includes a wavelength band separating unit on the image-capturing surface.

36. The endoscope apparatus according to claim 27, wherein the signal processing unit generates first band region image data and second band region image data by narrowband light of two non-overlapping band regions, which is restricted and irradiated by the two-band restricting unit, and generates from the first band region image data and the second band region image data three-channel color image data which is outputted to a displaying unit.

37. The endoscope apparatus according to claim 36, wherein the three-channel color image data is R image data, G image data and B image data outputted to the displaying unit.

38. The endoscope apparatus according to claim 36, wherein:
the first band region image data is image data based on an image-capturing signal capturing an image via the narrowband light of the long wavelength band side of the narrowband light of the two non-overlapping band regions restricted and irradiated by the two-band restricting unit;
the second band region image data is image data based on an image-capturing signal capturing an image via the narrowband light of the short wavelength band side of the narrowband light of the two non-overlapping band regions restricted and irradiated by the two-band restricting unit; and
the signal processing unit generates the R image data by the first band region image data, performs a prescribed weighting computation for the second band region image data, and generates the G image data and the B image data.

39. The endoscope apparatus according to claim 27, wherein the illumination light includes a visible light region.

40. The endoscope apparatus according to claim 27, wherein a ratio of color signal components, which are images captured via at least a plurality of wavelength bands, is changed at ordinary-light observation via a broadband illumination light and at narrowband-light observation via a narrowband illumination light, and a light modulation reference signal which adjusts the quantity of light of the illumination light is generated.

41. The endoscope apparatus according to claim 40, wherein the broadband illumination light and the narrowband illumination light are synchronous-type illumination lights which simultaneously illuminate illumination light of respective pluralities of wavelength bands, and the light modulation reference signal is generated at narrowband-light observation such that a ratio of color signals captured on the short wavelength side is greater than a ratio of color signals captured on the long wavelength side.

42. The endoscope apparatus according to claim 40, wherein the broadband illumination light and the narrowband illumination light are surface-sequential-type illumination lights which sequentially illuminate illumination light of respective pluralities of wavelength bands, and the light modulation reference signal is generated at narrowband-light observation such that a ratio of color signals captured on the short wavelength side is greater than a ratio of color signals captured on the long wavelength side.

43. The endoscope apparatus according to claim 40, wherein a value, which constitutes a target when adjusting the quantity of light of the illumination light using the light modulation reference signal, is switched at the ordinary-light observation and at the narrowband-light observation.

44. The endoscope apparatus according to claim 40, wherein the light modulation reference signal is generated at narrowband-light observation using G and B color signals which correspond to green (G) and blue (B) wavelength bands.

45. The endoscope apparatus according to claim 40, wherein the light modulation reference signal is generated using a gain control amplifier.

46. The endoscope apparatus according to claim 40, wherein the light modulation reference signal is generated using a plurality of multipliers.

47. The endoscope apparatus according to claim 27, comprising:
- a color separating unit for separating output signals from the image-capturing unit into a luminance signal and a color difference signal; and
- a processing characteristic changing unit for changing a processing characteristic relative to a signal which has undergone color separation by the color separating unit in accordance with switching in signal processing to the narrowband light from the illumination light.

48. The endoscope apparatus according to claim 47, comprising a band restricting unit for carrying out band restriction for the color difference signal separated by the color separating unit, wherein when switching is carried out from illumination light of the visible region to illumination light of a narrowband, the processing characteristic changing unit changes a characteristic of a pass band by the band restricting unit to broadband.

49. The endoscope apparatus according to claim 47, comprising a converting unit for converting from the luminance signal and color difference signal separated by the color separating unit to three primary color signals, wherein when switching is carried out from illumination light of the visible region to illumination light of a narrowband, the processing characteristic changing unit changes a conversion coefficient which determines a conversion characteristic by the converting unit.

50. The endoscope apparatus according to claim 49, wherein the converting unit converts the luminance signal and color difference signal to three primary color signals which have practically no mixed colors.

51. The endoscope apparatus according to claim 49, further comprising a second converting unit for converting the three primary color signals to a luminance signal and a color difference signal, wherein when switching from illumination light of the visible region to narrowband illumination light, the second converting unit changes conversion characteristics so as to increase the weighting of a short wavelength color signal in the three primary color signals.

52. The endoscope apparatus according to claim 47, further comprising a modulated-light signal generating unit for controlling the quantity of light of illumination light, and a gain controlling unit for variably controlling the level of the video signal, wherein the operation of the modulated-light signal generating unit is given priority over the operation of the gain controlling unit.

53. The endoscope apparatus according to claim 47, comprising a converting unit for converting the luminance signal and color difference signal separated by the color separating unit to a second luminance signal and a second color difference signal, wherein when switching from illumination light of the visible region to narrowband illumination light, the converting unit changes conversion characteristics so as to increase the weighting of a short wavelength color signal.

54. The endoscope apparatus according to claim 47, wherein when switching from illumination light of the visible region to narrowband illumination light, a γ characteristic is changed.

55. The endoscope apparatus according to claim 47, wherein when switching from illumination light of the visible region to narrowband illumination light, a highlighting unit changes a highlighting characteristic.

* * * * *